(12) United States Patent
James et al.

(10) Patent No.: US 7,794,732 B2
(45) Date of Patent: Sep. 14, 2010

(54) ANTHRAX COMPOSITIONS AND METHODS OF USE AND PRODUCTION

(75) Inventors: Judith A. James, Edmond, OK (US); Darise Farris, Edmond, OK (US); Sherry Crowe, Midwest City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 236 days.

(21) Appl. No.: 11/748,268

(22) Filed: May 14, 2007

(65) Prior Publication Data

US 2010/0172926 A1 Jul. 8, 2010

Related U.S. Application Data

(60) Provisional application No. 60/799,819, filed on May 12, 2006.

(51) Int. Cl.
  *A61K 39/07* (2006.01)
(52) U.S. Cl. ............ 424/246.1; 424/185.1; 424/190.1; 424/192.1; 435/7.1; 435/7.32; 530/300; 530/350
(58) Field of Classification Search ............... None
  See application file for complete search history.

(56) References Cited

U.S. PATENT DOCUMENTS

| | | | |
|---|---|---|---|
| 5,800,821 A | 9/1998 | Acheson et al. | |
| 5,840,312 A | 11/1998 | Mock et al. | |
| 5,951,976 A | 9/1999 | Segal | |
| 6,224,870 B1 | 5/2001 | Segal | |
| 6,331,415 B1 | 12/2001 | Cabilly et al. | |
| 6,348,450 B1 | 2/2002 | Tang et al. | |
| 6,403,080 B1 | 6/2002 | Segal | |
| 6,479,258 B1 | 11/2002 | Short | |
| 6,541,011 B2 | 4/2003 | Punnonen et al. | |
| 6,569,435 B1 | 5/2003 | Punnonen et al. | |
| 6,632,436 B2 | 10/2003 | Segal | |
| 6,689,757 B1 | 2/2004 | Craig | |
| 6,713,279 B1 | 3/2004 | Short | |
| 6,716,823 B1 | 4/2004 | Tang et al. | |
| 6,770,479 B1 * | 8/2004 | Lee et al. .................... | 435/456 |
| 6,805,857 B2 | 10/2004 | Shah | |
| 6,927,068 B2 | 8/2005 | Simonson et al. | |
| 6,979,449 B1 | 12/2005 | Mock | |
| 7,018,835 B2 | 3/2006 | Hone | |
| 2001/0031264 A1 | 10/2001 | Segal | |
| 2002/0034512 A1 | 3/2002 | Ivins et al. | |
| 2002/0039588 A1 | 4/2002 | Collier et al. | |
| 2002/0048590 A1 | 4/2002 | Klimpel et al. | |
| 2002/0051791 A1 | 5/2002 | Galloway et al. | |
| 2002/0082386 A1 | 6/2002 | Mangold et al. | |
| 2002/0131974 A1 | 9/2002 | Segal | |
| 2002/0142002 A1 | 10/2002 | Galloway et al. | |
| 2002/0197272 A1 | 12/2002 | Galloway et al. | |
| 2002/0198162 A1 | 12/2002 | Punnonen et al. | |
| 2003/0003109 A1 | 1/2003 | Galloway et al. | |
| 2003/0036181 A1 | 2/2003 | Okkels et al. | |
| 2003/0078192 A1 | 4/2003 | Winter et al. | |
| 2003/0093040 A1 | 5/2003 | Mikszta et al. | |
| 2003/0108556 A1 | 6/2003 | Mekalanos et al. | |
| 2003/0118591 A1 | 6/2003 | Levy | |
| 2003/0125278 A1 | 7/2003 | Tang et al. | |
| 2003/0133942 A1 | 7/2003 | Segal | |
| 2003/0138459 A1 | 7/2003 | Wang | |
| 2003/0143636 A1 | 7/2003 | Simonson et al. | |
| 2003/0144193 A1 | 7/2003 | Rottman et al. | |
| 2003/0198651 A1 | 10/2003 | Klimpel et al. | |
| 2003/0198995 A1 | 10/2003 | Sabbadini et al. | |
| 2003/0198996 A1 | 10/2003 | Surber et al. | |
| 2003/0199005 A1 | 10/2003 | Sabbadini et al. | |
| 2003/0199088 A1 | 10/2003 | Sabbadini et al. | |
| 2003/0199089 A1 | 10/2003 | Surber et al. | |
| 2003/0202937 A1 | 10/2003 | Sabbadini et al. | |
| 2003/0202989 A1 | 10/2003 | Collier et al. | |
| 2003/0202783 A1 | 11/2003 | Cho | |

(Continued)

FOREIGN PATENT DOCUMENTS

WO    WO2005068493 A1 * 1/2004

(Continued)

OTHER PUBLICATIONS

Greenspan et al (Nature Biotechnology 7: 936-937, 1999).*

(Continued)

*Primary Examiner*—Jennifer E Graser
(74) *Attorney, Agent, or Firm*—Kilpatrick Stockton LLP; Jamie L. Greene

(57) ABSTRACT

Compositions and methods effective for eliciting an immune response for preventing or reducing infection or improving clinical outcomes caused by *Bacillus anthracis* are provided. The compositions include a naturally occurring or synthetic protein, peptide, or protein fragment containing all or an active portion of an antigenic epitope associated with anthrax toxin proteins optionally combined with a pharmaceutically acceptable carrier. The preferred antigenic epitopes correspond to immunogenic regions of protective antigen, lethal factor or edema factor, either individually or in combination. In addition, methods and compositions containing antibodies for reducing the effects of anthrax toxins are described. The methods involve administering to a human or animal the compositions described herein in a dosage sufficient to elicit an immune response or treat the anthrax infection.

15 Claims, 23 Drawing Sheets

U.S. PATENT DOCUMENTS

| | | |
|---|---|---|
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219752 A1 | 11/2003 | Short |
| 2003/0224444 A1 | 12/2003 | Sabbadini |
| 2003/0226155 A1 | 12/2003 | Sadeghi et al. |
| 2003/0228637 A1 | 12/2003 | Wang |
| 2003/0235594 A1 | 12/2003 | Humphreys et al. |
| 2003/0235818 A1 | 12/2003 | Katritch et al. |
| 2004/0001849 A1 | 1/2004 | Punnonen et al. |
| 2004/0005700 A1 | 1/2004 | Surber et al. |
| 2004/0009178 A1 | 1/2004 | Bowdish et al. |
| 2004/0009182 A1 | 1/2004 | Myers et al. |
| 2004/0009936 A1 | 1/2004 | Tang et al. |
| 2004/0009937 A1 | 1/2004 | Chen et al. |
| 2004/0009945 A1 | 1/2004 | Lee et al. |
| 2004/0013688 A1 | 1/2004 | Wise et al. |
| 2004/0014707 A1 | 1/2004 | Cirino et al. |
| 2004/0014715 A1 | 1/2004 | Ostroff |
| 2004/0018193 A1 | 1/2004 | Alibek et al. |
| 2004/0023897 A1 | 2/2004 | Caplan |
| 2004/0076638 A1 | 4/2004 | Shiloach et al. |
| 2004/0077842 A1 | 4/2004 | Himawan |
| 2004/0082530 A1 | 4/2004 | Schmaljohn et al. |
| 2004/0091503 A1 | 5/2004 | Segal et al. |
| 2004/0109871 A1 | 6/2004 | Pascual |
| 2004/0122217 A1 | 6/2004 | Segal et al. |
| 2004/0132678 A1 | 7/2004 | Hone |
| 2004/0146524 A1 | 7/2004 | Lyons et al. |
| 2004/0146549 A1 | 7/2004 | Ben-Sasson et al. |
| 2004/0147719 A1 | 7/2004 | Cornelis |
| 2004/0157330 A1 | 8/2004 | Sheridan et al. |
| 2004/0166120 A1 | 8/2004 | Thomas et al. |
| 2004/0171121 A1 | 9/2004 | Leppla et al. |
| 2004/0171565 A1 | 9/2004 | Hone |
| 2004/0180055 A1 | 9/2004 | Shah |
| 2004/0180389 A1 | 9/2004 | Segal et al. |
| 2004/0185064 A9 | 9/2004 | Wang |
| 2004/0197343 A1 | 10/2004 | Dubensky, Jr. et al. |
| 2004/0203084 A1 | 10/2004 | Levinson |
| 2004/0234521 A1 | 11/2004 | Himawan |
| 2004/0235075 A1 | 11/2004 | Cullum et al. |
| 2004/0235136 A1 | 11/2004 | Singh et al. |
| 2004/0253634 A1 | 12/2004 | Wang |
| 2004/0258699 A1 | 12/2004 | Bowdish et al. |
| 2004/0258702 A1 | 12/2004 | Blonder et al. |
| 2005/0002969 A1 | 1/2005 | Martyn |
| 2005/0031625 A1 | 2/2005 | Mohamed et al. |
| 2005/0031630 A1 | 2/2005 | Pizzo et al. |
| 2005/0036951 A1 | 2/2005 | Henderson |
| 2005/0054038 A1 | 3/2005 | Bhatnagar et al. |
| 2005/0058702 A1 | 3/2005 | Ben-Sasson et al. |
| 2005/0063986 A1 | 3/2005 | Bhatnagar et al. |
| 2005/0106647 A1 | 5/2005 | Harvey et al. |
| 2005/0112145 A1 | 5/2005 | Hudson et al. |
| 2005/0123550 A1 | 6/2005 | Laurent et al. |
| 2005/0136103 A1 | 6/2005 | Ben-Sasson et al. |
| 2005/0142151 A1 | 6/2005 | Nikolich et al. |
| 2005/0147590 A1 | 7/2005 | Sabbadini et al. |
| 2005/0148529 A1 | 7/2005 | Schmaljohn et al. |
| 2005/0202460 A1 | 9/2005 | Leighton et al. |
| 2005/0220807 A1 | 10/2005 | Lu et al. |
| 2005/0226892 A1 | 10/2005 | Rao |
| 2005/0249742 A1 | 11/2005 | Ruprecht et al. |
| 2005/0260736 A1 | 11/2005 | Georgiou et al. |
| 2005/0267294 A1 | 12/2005 | Harvey et al. |
| 2005/0271675 A1 | 12/2005 | Schneerson et al. |
| 2005/0271689 A1 | 12/2005 | Huang et al. |
| 2005/0276756 A1 | 12/2005 | Hoo et al. |
| 2005/0281830 A1 | 12/2005 | Morrow et al. |
| 2005/0287149 A1 | 12/2005 | Keler et al. |
| 2005/0287167 A1 | 12/2005 | zur Megede et al. |
| 2006/0002947 A1 | 1/2006 | Humphreys et al. |
| 2006/0013800 A1 | 1/2006 | Le Buanec et al. |
| 2006/0019380 A1 | 1/2006 | Crystal et al. |
| 2006/0045888 A1 | 3/2006 | Punnonen et al. |
| 2006/0069052 A1 | 3/2006 | Hone |

FOREIGN PATENT DOCUMENTS

| | | | |
|---|---|---|---|
| WO | WO-2007/131363 A | 11/2007 | |

OTHER PUBLICATIONS

Chothia et al (The EMBO Journal, 1986, 5/4:823-26).*

Friedlander, A.M. et al.; "Anthrax vaccines"; Curr Top Microbiol Immunol. 2002; 271:33-60.

Greenfield, R.A. et al.; "Bacterial pathogens as biological weapons and agents of bioterrorism"; Am. J. Med. Sci. Jun. 2002; 323(6):299-315.

Guarner, Jeannette et al.; "Pathology and Pathogenesis of Bioterrorism-Related Inhalational Anthrax; American Journal of Pathology"; vol. 163, No. 2, Aug. 2003; pp. 701-709.

Keller, Margaret A. et al.; "Passive Immunity in Prevention and Treatment of Infectious Diseases"; Clinical Microbiology Reviews, Oct. 2000, pp. 602-614.

Little, S.F. et al.; "Structure-function analysis of *Bacillus anthracis* edema factor by using monoclonal antibodies"; Biochem Biophys Res Commun. Mar. 15, 1994; 199(2):678-82.

Little, S.F. et al.; "Characterization of lethal factor binding and cell receptor binding domains of protective antigen of *Bacillus anthracis* using monoclonal antibodies"; Microbiology, Mar. 1996; 142 (*Pt 3): 707-15.

Little, S.F. et al.; "Passive Protection by Polyclonal Antibodies against *Bacillus anthracis* Infection in Guinea Pigs"; Infection and Immunity, Dec. 1997, pp. 5171-5175.

Little, Stephen F. et al.; "Production and Characterization of Monoclonal Antibodies to the Protective Antigen Component of *Bacillus anthracis* Toxin"; Infection and Immunity, Jul. 1988, pp. 1807-1813.

Mohamed, Nehal et al.; "Enhancement of Anthrax Lethal Toxin Cytotoxicity: a Subset of Monoclonal Antibodies against Protectivbe Antigen Increases Lethal Toxin-Mediated Killing of Murine Macrophages"; Infect. Immun.; 2004;72:3276-3283.

Mourez, M.; "Anthrax toxins"; Rev Physiol Biochem Pharmacol.; 2004; 152:135-64. Epub Jul. 27, 2004.

Pannifer, Andrew D.; "Crystal structure of the anthrax lethal factor"; Nature, vol. 414; Nov. 8, 2001; www.nature.com. pp. 229-233.

Price, Brian M. et al.; "Protection against Anthrax Lethal Toxin Challenge by Genetic Immunization with a Plasmid Encoding the Lethal Factor Protein"; Infection and Immunity, Jul. 2001, pp. 4509-4515.

Quinn, Conrad P. et al.; "Immune Responses to *Bacillus anthracis* Protective Antigen in Patients with Bioterrorism-Related Cutaneous or Inhalation Anthrax"; Journal of Infectious Diseases 2004: 190; 1228-36.

Singh, Yogendra et al.; "The Carboxyl-terminal End of Protective Antigen Is Required for Receptor Binding and Anthrax Toxin Activity"; The Journal of Biological Chemistry; vol. 266, No. 23, Issue of Aug. 15, pp. 15493-15497.

Welkos, Susan et al.; "The role of antibodies to *Bacillus anthracis* and anthrax toxin components in inhibiting the early stages of infection by anthrax spores"; Microbiology (2001), 17, 1677-1685.

Partial International Search Report for PCT/US2007/011608 dated Mar. 31, 2008.

Gerdon et al., "Epitope Mapping of the Protective Antigen of *B. anthracis* by Using Nanoclusters Presenting Conformational Peptide Epitopes", *Angewandte* Chemie, vol. 45, No. 4, Jan. 16, 2006, pp. 594-598.

Gubbins, et al., "Production and Characterization of Neutralizing Monoclonal Antibodies that Recognize an Epitope in Domain 2 of *Bacillus anthracis* Protective Antigen", FEMS Immunology and Medical Microbiology; vol. 47, No. 3, Aug. 2006, 436-443.

Laffly, et al., "Selection of a Macaque Fab with Framework Regions Like Those in Humans, High Affinity, and Ability to Neutralize the Protective Antigen (PA) of *Bacillus anthracis* by Binding to the Segment of PA between Residues 686 and 694", Antimicrobial Agents and Chemotherapy American Society for Microbiology, Washington; vol. 49, No. 8, Aug. 2005, pp. 3414-3420.

Sawada-Hirai, et al., "Human Anti-Anthrax Protective Antigen Neutralizing Monoclonal Antibodies Derived from Donors Vaccinated with Anthrax Vaccine Absorbed", Journal of Immune Based Therapies and Vaccines, Biomed Central LTD; vol. 2, No. 1, May 12, 2004, p. 5.

Wild, et al., "Human Antibodies from Immunized Donors are Protective Against Anthrax Toxin in Vivo", Bio/Technology, Nature Publishing Co.; vol. 12, No. 11, Oct. 12, 2003, pp. 1305-1306.

Zhang, et al., "The 2beta2-2beta3 Loop of Anthrax Protective Antigen Contains a Dominant Neutralizing Epitope", Biochemical and Biophysical Research Communications, vol. 341, No. 4, Mar. 24, 2006, pp. 1169-1170.

* cited by examiner

Adapted from Collier and Young. Annu Rev Cell Dev Biol, 2003

- Inhibition of PMN phagocytic capacity
- Edema (local)
- Lethal to mice (systemic)

- Macrophage death
- Dendritic cell death
- Systemic effects
- Lethal to mice

Fig. 2

*Prime:* d0 (100μg recombinant Ag in CFA)
*Boost:* (50μg in IFA)  d10    d24    d38
*Bleed:* -3d    d14    d28    d42 // d108/119

Solid phase epitope mapping using pooled sera (10mers overlapping by 8 aa)

Challenge: 3X A/J LD$_{50}$ (300μg PA +125μg LF) lethal toxin on day 109/120

Fig. 4

*Prime:* d0 (100μg recombinant Ag in CFA)
*Boost:* (50μg in IFA)  d10    d24    d38
*Bleed:* -3d    d14    d28    d42 // d108/119
         -3  0    5    10   Days 15   20   25   30    110

Challenge: 3X A/J $LD_{50}$ (300μg PA +125μg LF ) lethal toxin on day 109/120

Survival:    9/10    7/8    1/7 p= 0.009 p =0.004

*Upper numbers and colored boxes correspond to figure at right

**Numbers in parentheses correspond to sequential order of composite sequences as listed in Table 1

LF crystal structure showing a subset of 27 LF epitopes

*Upper numbers and colored boxes correspond to figure at right

**Numbers in parentheses correspond to No. on Structure as listed in Table 4

PA crystal structure showing a subset of 25 mouse PA epitopes

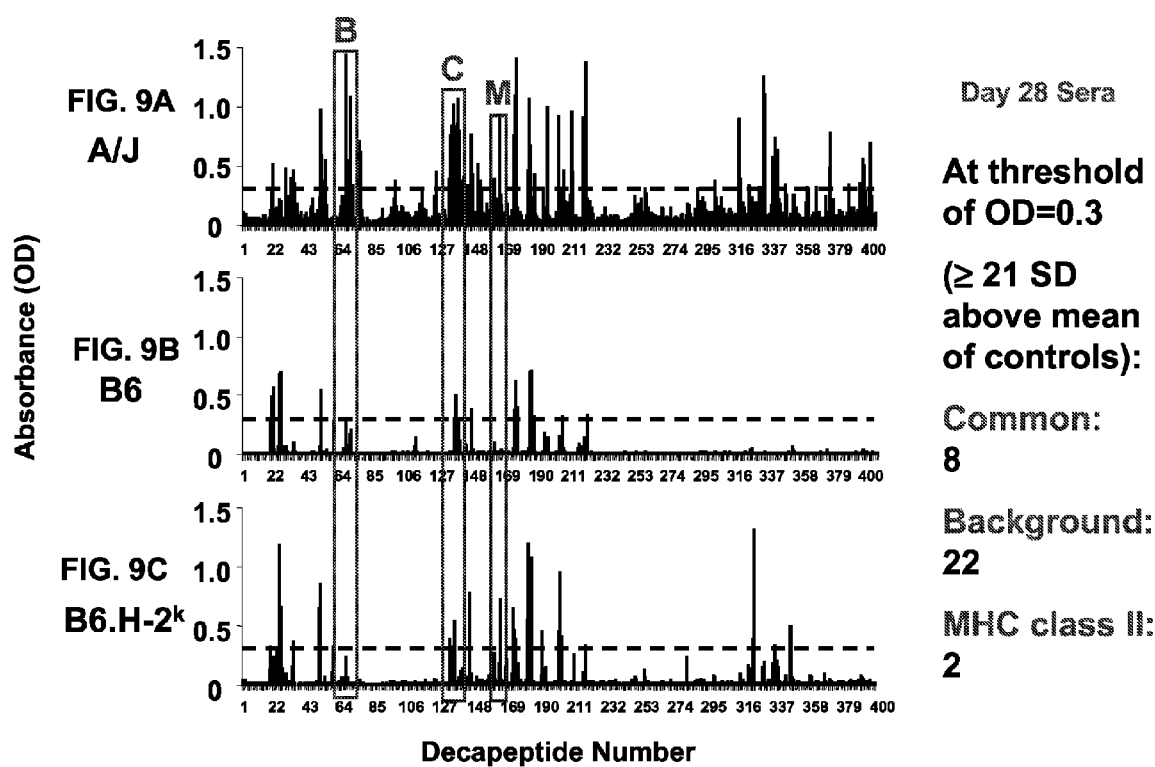

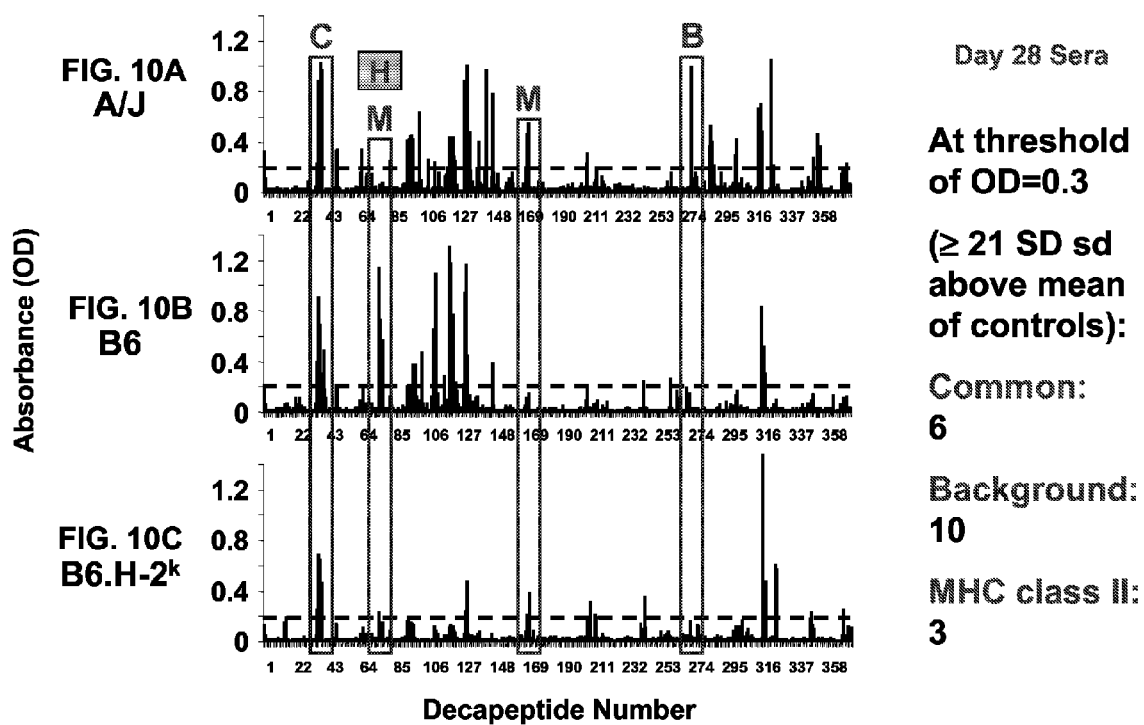

|  | 10,000 | 1,000 | 100 | 10 | 1 |
|---|---|---|---|---|---|
| Age | 26 ± 2.6 | 35 ± 8.2 | 33 ± 9.7 | 34 ± 8.6 | 38 ± 4.2 |
| Gender:<br>Female<br>Male | 1 (14%)<br>6 (86%) | 16 (30%)<br>38 (70%) | 7 (21%)<br>26 (79%) | 1 (8%)<br>12 (92%) | 4 (57%)<br>3 (43%) |
| Race:<br>Asian<br>African Am.<br>Caucasian<br>Other | 0<br>0<br>6 (86%)<br>1 (14%) | 4 (8%)<br>12 (22%)<br>32 (59%)<br>6 (11%) | 1 (3%)<br>10 (30%)<br>19 (58%)<br>3 (9%) | 0<br>2 (15%)<br>10 (77%)<br>1 (8%) | 1 (14%)<br>3 (43%)<br>3 (43%)<br>0 |
| Number of Vaccinations | 5.4 ± 1.1 | 5.7 ± 1.2 | 4.6 ± 1.3 | 3.9 ± 1.5 | 4.7 ± 1.7 |
| Years post Vaccination | 1.0 ± 0.4 | 2.2 ± 0.6 | 2.6 ± 1.4 | 3.4 ± 1.5 | 4.1 ± 2.9 |
| Total | 7 | 54 | 33 | 13 | 7 |

FIG. 12A
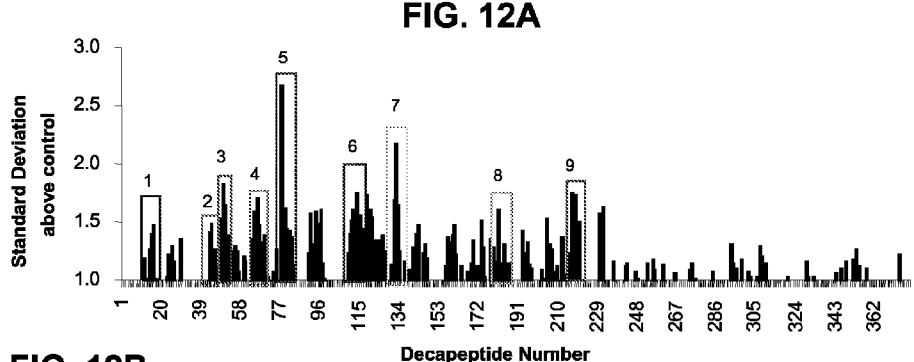
FIG. 12B
FIG. 12C
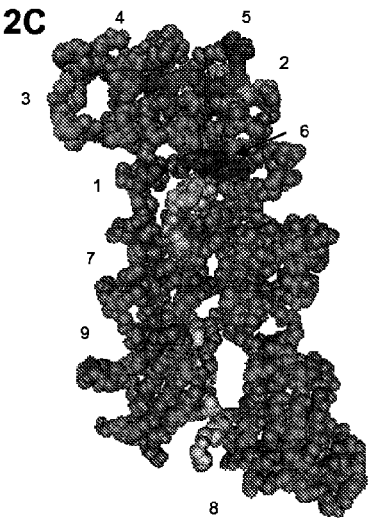
| # | % Pos (N=29) | Function |
|---|---|---|
| 1 | 41 | PA20 |
| 2 | 31 | PA20 |
| 3 | 48 | PA20 |
| 4 | 37 | PA20 |
| 5 | 44 | PA20 |
| 6 | 41 | Ligand Binding |
| 7 | 37 | Ligand Binding (Mutant Inhibitory) |
| 8 | 34 | Translocation |
| 9 | 34 | Translocation |
Epitope = > 2SD above control and > 30% positive

Fig. 13

| Epitope Number | Pin Number | Sequence | AA (ours) | AA (collier) | % Positive | Domain | Notes |
|---|---|---|---|---|---|---|---|
| 1 | 14-16 | IQAEVKQENRLLNE (SEQ ID NO: 187) | 24-40 | 1-10 | 41.38 | PA 20 | first 3 AA not on Collier |
| 2 | 43-44 | ENQTFQSAIWSG (SEQ ID NO: 188) | 85-96 | 56-67 | 31.04 | PA 20 | |
| 3 | 49-50 | FIKVKKSDEYTF (SEQ ID NO: 189) | 97-106 | 68-77 | 48.28 | PA 20 | |
| 4 | 64-66 | NKASNKIRLEKG (SEQ ID NO: 190) | 127-140 | 98-111 | 37.93 | PA 20 | |
| 5 | 77-78 | NPTEKGLDFKLY (SEQ ID NO: 191) | 153-164 | 124-135 | 44.83 | PA 20 | B6 mice |
| 6 | 111-112 | YTVDVKNKRT (SEQ ID NO: 192) | 221-231 | 191-202 | 41.38 | LIGAND/ OLIGO | |
| 7 | 132-133 | SDFEKVTGRIDK (SEQ ID NO: 193) | 263-274 | 234-245 | 37.93 | LIGAND | Mouse; T240 mutants |
| 8 | 180-181 | STVAIDHSLSLA (SEQ ID NO: 194) | 359-370 | 330-341 | 34.48 | TRANSLOCATION | |
| 9 | 218-219 | APNNYYPSKNLA (SEQ ID NO: 195) | 435-446 | 406-417 | 34.48 | TRANSLOCATION | |

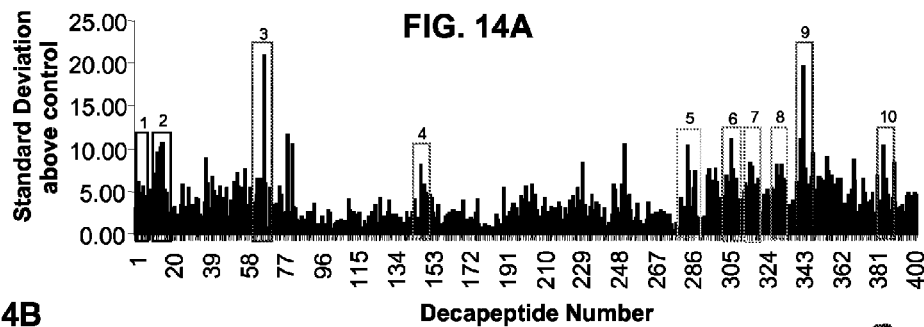
FIG. 14A
FIG. 14B
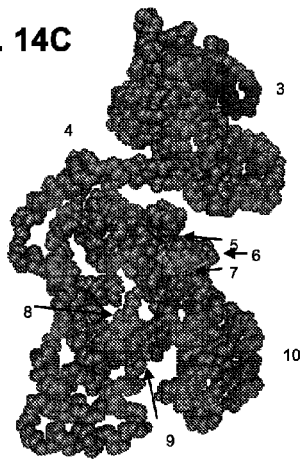
FIG. 14C
| # | % Pos (N=9) | Function |
|---|---|---|
| 1 | 78 | Leader |
| 2 | 56 | Leader |
| 3 | 56 | PA Binding |
| 4 | 67 | PA Binding |
| 5 | 78 | ADP Ribosyltransferase |
| 6 | 78 | ADP Ribosyltransferase |
| 7 | 56 | Zinc Metalloprotease |
| 8 | 67 | Zinc Metalloprotease |
| 9 | 89 | Zinc Metalloprotease |
| 10 | 67 | Zinc Metalloprotease |
Epitope = > 2SD above control and > 50% positive

Fig. 15

| Epitope Number | Pin Number | Sequence | AA (ours) | AA (collier) | % Positive | Domain | Notes |
|---|---|---|---|---|---|---|---|
| 1 | 3-6 | KEFIKVISMSCLVTAI (SEQ ID 177) | 5-20 | | 78 | | LEADER |
| 2 | 13-14 | PVFIPLVQGAGG (SEQ ID NO: 178) | 25-36 | | 56 | | LEADER |
| 3 | 66-68 | SEDKKKIKDIYGKD (SEQ ID: 179) | 131-144 | 98-111 | 56 | PA BINDING | MOUSE |
| 4 | 146-147 | ELKDQRMLARYE (SEQ ID NO: 180) | 291-302 | 258-269 | 67 | PA BINDING | |
| 5 | 294-296 | KIDTKIQEAQLNIN (SEQ ID NO: 181) | 587-600 | 554-567 | 78 | ADP RIBO | |
| 6 | 298-300 | AQLNINQEWNKALG (SEQ ID NO: 182) | 595-608 | 562-575 | 78 | ADPRIBO | |
| 7 | 310-312 | NVHNRYASNIVESA (SEQ ID NO:183) | 619-632 | 586-599 | 56 | ZINC METALLO | |
| 8 | 333-334 | TDITLPNIAEQY (SEQ ID NO: 184) | 665-676 | 632-643 | 67 | ZINC METALLO | |
| 9 | 339-343 | THQDEIYEQVHSKGLYVP (SEQ ID NO:185) | 677-694 | 644-661 | 67 | ZINC METALLO | MOUSE |
| 10 | 389-393 | MHSTDHAERLKVQKNAPK (SEQ ID NO: 186) | 777-794 | 744-761 | 67 | ZINC METALLO | |

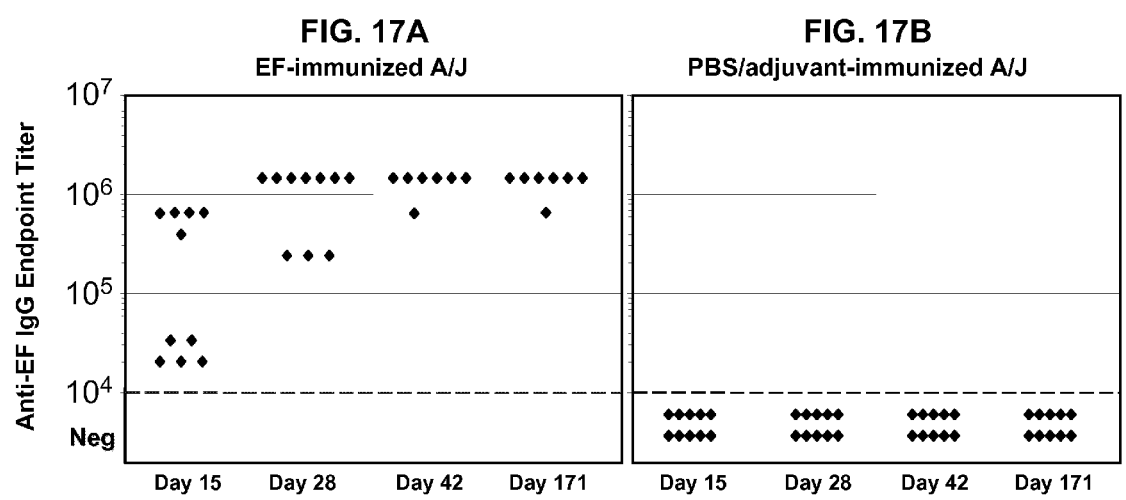

FIG. 18A LD$_{50}$ ETx in A/J mice (administered 2.5:1.0 PA:EF)

FIG. 18B 4X LD$_{50}$ ETx Challenge

FIG. 19A

Absorbance (OD$_{405}$) vs Decapeptide Number

Regions labeled: IB (1, 2), B (3, 4), H/B (5), H (6, 7-9)

Day 15

Day 28

Adjuvant Alone Day 28

FIG. 19B

Mutants reduce binding to PA

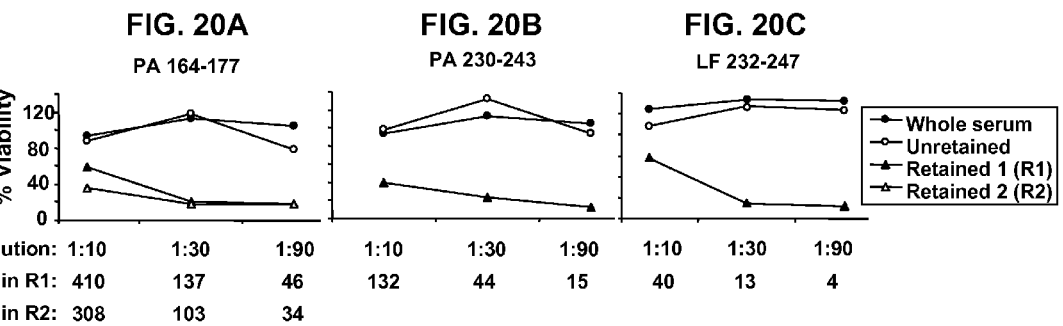

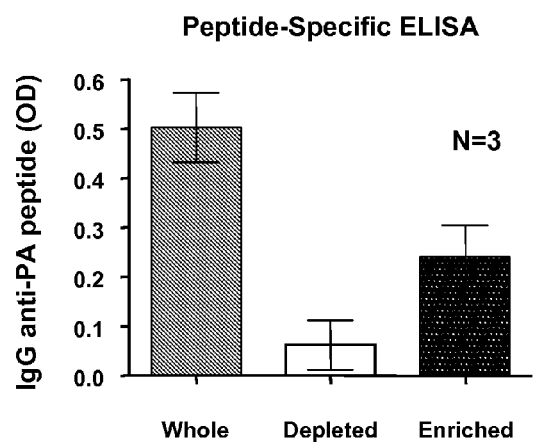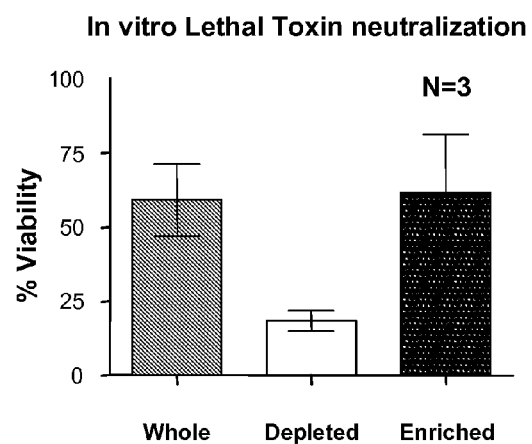
FIG. 21A Peptide-Specific ELISA
FIG. 21B In vitro Lethal Toxin neutralization Furin Cleavage Site Ligand Binding Site Receptor Binding Site

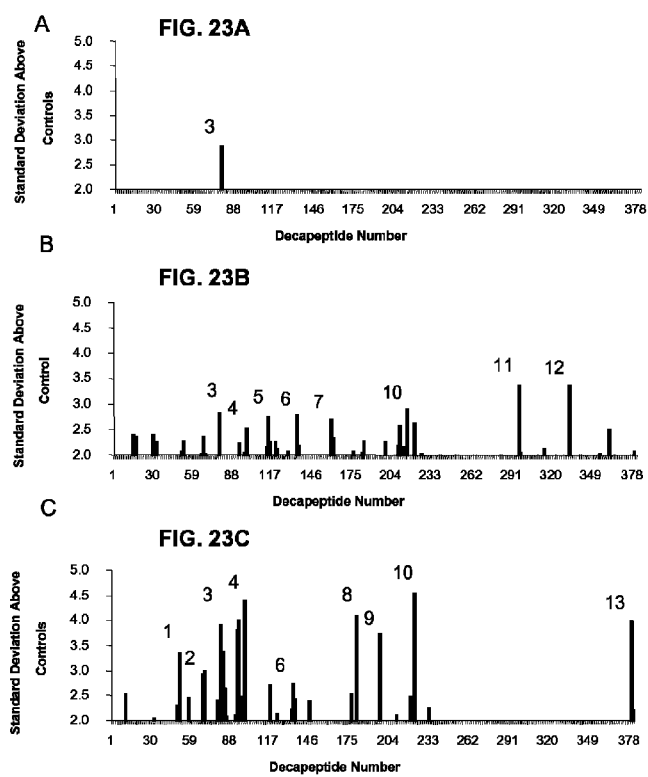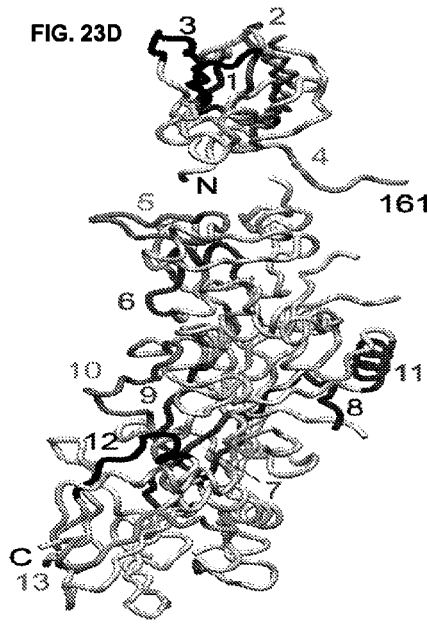

ANTHRAX COMPOSITIONS AND METHODS OF USE AND PRODUCTION

CLAIM OF PRIORITY AND CROSS-REFERENCE TO RELATED APPLICATIONS

This application claims priority to U.S. Provisional Patent Application No. 60/799,819, filed May 12, 2006 and is incorporated herein by reference.

TECHNICAL FIELD

The present invention relates to the field of immunology and more particularly relates to methods and compositions for treating, preventing or reducing anthrax infection in humans or animals.

BACKGROUND OF THE INVENTION

Anthrax is a disease caused by the sporulating bacteria *Bacillus anthracis*. Humans working with animal products are at risk for contracting anthrax, particularly individuals such as veterinarians, laboratory technicians, ranchers and employees working with the skin or hair of animals. Areas such as Iran, Turkey, Iraq, Pakistan, and sub-Saharan Africa are hyperendemic for anthrax, although the organism can be found in most areas of the world. General worldwide populations are vulnerable to *B. anthracis* infection as a consequence of acts of bioterror, whereas military troops are vulnerable to infection as a consequence of acts of bioterror and/or war.

Anthrax manifests disease in three different ways: inhalation anthrax disease, gastrointestinal anthrax disease, and cutaneous anthrax disease. Inhalation anthrax disease is caused by inhaling spores. Gastrointestinal anthrax is caused by ingesting spores in contaminated meat, and cutaneous anthrax disease occurs when spores contact an open wound. Untreated inhalation or gastrointestinal anthrax has a case fatality rate of essentially 100 percent while cutaneous anthrax has a case fatality rate of up to 25 percent.

For persons infected with anthrax, treatment success is limited by several factors, such as the increased incidence of antibiotic resistance, the overwhelming septic responses, which can occur before antibiotics could be effective, and treatment delays based upon decreased suspicion and poor methods of early detection. that all can lessen the chance of survival. It is known that early treatment of anthrax with antibiotics is essential to reduce mortality, although not completely effective with inhalation infections. Delays in treatment profoundly decrease survival rates. Early treatment, however, is difficult because initial symptoms of the infection resemble common, non-fatal infections. For example, the inhalation of anthrax spores may initially present symptoms resembling those of the common cold. In addition, symptoms of anthrax infection, depending on how the bacterium is contracted, may take seven to sixty days to appear. Moreover, even prompt, effective antibiotic treatment does not ameliorate the effects of circulating toxins, which can remain in the blood at high levels and continue to mediate their pathogenic effects.

The pathogenicity of *Bacillus anthracis* is expressed in two ways: a toxic effect made evident by the appearance of edema, and a so-called lethal toxic effect that may lead to the death of the subject infected. These effects are attributed to the presence of toxins produced by a combination of three proteins that represent the toxin system: protective antigen (PA), lethal factor (LF) and edema factor (EF). In humans and other mammals, toxins increase in the body even during early stages of infection when the host appears asymptomatic. This explains why delays in treatment can be fatal. Thus, there is not only a critical need for improved anthrax intervention therapies, including treatments that interfere with the deleterious actions of the toxins, but also a critical need for point-of-care, rapid, and extremely sensitive diagnostic tests to establish the presence of anthrax early in the infection.

Passive immunization, an effort to neutralize toxins with antibodies, usually polyclonal antibodies, has been used as a therapeutic intervention for a variety of bacterial infections (Keller and Stiehm, 2000). A major limitation of using polyclonal antisera in patients is the possibility of "serum sickness" due to a patient's immune response to proteins derived from a different species. In addition, higher affinity antibodies are more effective for toxin neutralization, but there is no general way to enhance intentionally the affinity of polyclonal sera or even monoclonal antibodies derived from hybridomas. In addition, traditional approaches using pooled donor intravenous immunoglobulins (IVIG) is not effective as normal donors do not have effective humoral immunity against *Bacillus anthracis*.

Although vaccines against *Bacillus anthracis* are currently available, they are not optimal. Even the most recent commercially available vaccines require multiple primary injections, yearly boosters, and fail to provide proven long-term effectiveness against inhalation attacks and adverse events. In addition, currently available vaccines exhibit severe adverse effects.

The mechanism for anthrax toxicity is as follows. The 83 kDa form of protective antigen (PA83) is secreted from rapidly growing *Bacillus anthracis* cells and binds to a specific host cell surface receptor, such as TEM8 or CMG2. (H. M. Scobie and J. A. Young, *Curr. Opin. Micro.* 8, 106-112 (2005)). Subsequent cleavage by membrane-bound furin, and/or a furin-like protease, possibly PACE4, releases an amino terminal 20 kDa fragment, resulting in receptor-bound PA63. PA63 subunits then oligomerize into heptameric rings, which in turn create binding sites for the lethal factor and edema factor components of *Bacillus anthracis* toxins. Endocytosis of the receptor/toxin complex into acidic endosomes elicits a conformational change in PA63, whereby the A subunits (LF or EF) of the toxin are released into the endosome. Lysosomal acidification and subsequent receptor release facilitate irreversible membrane insertion of the oligomeric PA63 pore. The pore permits transport of LF and/or EF into the cytoplasm where they elicit their respective toxicities.

EF is a calcium/calmodulin-dependent adenylate cyclase that is toxic to most cell types and causes local inflammation and edema, but is not usually lethal. Edema toxin, composed of protective antigen and edema factor is been recently shown to cause tissue lesion and death in a mouse model (see "*Bacillus anthracis* edema toxin causes extensive tissue lesions and rapid lethality in mice" by Firoved, A. M., G. F. Miller, M. Moayeri, R. Kakkar, Y. Shen, J. F. Wiggins, E. M. McNally, W. J. Tang, and S. H. Leppla. *Am J Pathol* 167:1309-1320 (2005)).

LF is a cell-type specific metalloprotease that cleaves MAP-kinase-kinases and several peptide hormones. Lethal toxin, formed by the combination of protective antigen and lethal factor is a zinc dependent protease that results in lysis of macrophages. Lethal factor is the major virulence factor associated with anthrax toxicity and is thought to be responsible for systemic shock and death. Neither of the toxin A subunits are pathogenic in the absence of cytoplasmic delivery by PA or mechanical means (See, "Macrophages are sensitive to anthrax lethal toxin through an acid-dependent process" by A. M. Friedlander *J. Biol. Chem.* 261, 7123 (1986)).

The crystal structures of PA83 and heptameric PA63 have been resolved (See, e.g., "Crystal-structure of the anthrax toxin protective antigen" by C. Petosa et al., *Nature*. 385, 833 (1997)). These structural data support the experimental data (See, e.g., "Characterization of lethal factor-binding and cell-receptor binding domains of protective antigen of *Bacillus anthracis* using monoclonal-antibodies" by S. F. Little et al., *Microbiology-UK*. 142, 707 (1996) and "The carboxyl-terminal end of protective antigen is required for receptor-binding and anthrax toxin activity" by Y. Singh et al., *J. Biol. Chem.* 266,15493 (1991)) that indicate that domain 4, the carboxy-terminus of PA63, is responsible for receptor-mediated uptake of the toxin complex.

*Bacillus anthracis* has been used for over sixty years as a biological weapon and is a likely agent for a large-scale attack based upon the relative ease of obtaining and growing the bacterium, as well as the stability of the spores. Weaponized anthrax was first developed in 1941 by the British government, which tested the release of anthrax spores on an island near Scotland (Mourez, M. *Rev Physiol Biochem Pharmacol* 152:135-164 (2004) and Greenfield, R. A et al. *Am J Med Sci* 323:299-315 (2002)). While no individuals were infected during this test, the island remained a biohazard for forty-five years until seawater and formaldehyde was used to sterilize the soil. Since that time, however, there have been accidental and deliberate releases of militarized anthrax resulting in human infections and deaths. An accidental release of anthrax from a USSR military facility in 1979 caused 68 deaths and resulted in infection of cattle up to 31 miles away. And in 2001, the deliberate spread of anthrax through infected letters in the US resulted in 22 cases of anthrax (11 cutaneous and 11 inhalation), with five deaths (see Guarner, J. et al. *Am J Pathol* 163:701-709 (2003) and Quinn, C. P. et al. *J Infect Dis* 190: 1228-1236 (2004)). These incidents highlight the need for a safe, effective vaccine that provides protection from an aerosolized release of *Bacillus anthracis* spores and potential directed immunotherapeutics for early intervention.

The current US vaccine (anthrax vaccine absorbed, AVA) is an alhydrogel absorbed cell-free filtrate of the attenuated V770-NP1-R strain, a non-encapsulated bovine isolate. This vaccination is administered at 0, 2, 4 weeks and again at 6, 12, and 18 months with yearly boosters recommended. The primary data on this vaccine has been obtained from animal studies and indicates that, while AVA does not protect mice from lethal challenge with fully virulent strains of *B. anthracis*, vaccinated mice are protected against challenge with nonencapsulated strains. These models have also demonstrated that passive transfer of antibodies against the major toxin proteins (PA, LF, and EF) can provide protection against challenge with attenuated strains (see Little, S. F. et al. *Infect Immun* 65:5171-5175 (1997); Little, S. F. et al. *Infect Immun* 56:1807-1813 (1988); Price, B. M et al. *Infect Immun* 69:4509-4515 (2001) and Welkos, S., et al. *Microbiology* 147:1677-1685 (2001)). Antibodies to PA, LF, and EF have also been detected in serum samples of individuals diagnosed with clinical anthrax, but vaccination results in primarily anti-protective antigen antibodies. However, several studies using mice vaccinated with mutant strains of *Bacillus anthracis* have shown significant contributions of LF and EF to protection (see Mohamed, N. et al. *Infect Immun* 72:3276-3283 (2004) and Little, S. F. et al. *Biochem Biophys Res Commun* 199:676-682 (1994)). Thus enhancing the levels of antibodies against these proteins might enhance protection.

Accordingly, because the current vaccine is not optimal, new and improved preventative compositions and methods are necessary.

What are needed are methods and compositions that can prevent, inhibit and diminish the symptoms of *Bacillus anthracis* infection. The compositions should be able to overcome the activity of anthrax toxins, namely protective antigen, lethal factor and edema factor. Preferably the compositions should be able to induce an immune response in an animal or human. Also needed are compositions that can be used to produce neutralizing antibodies directed to components of the anthrax toxins, such as lethal factor and edema factor. Furthermore, what are needed are methods and compositions that can be used for immunotherapy, specifically directed to *Bacillus anthracis* infection. Finally, the methods and compositions for preventing, inhibiting and diminishing the symptoms of *Bacillus anthracis* infection should preferably be non-toxic and produce few side effects.

SUMMARY OF THE INVENTION

Methods and compositions for treating, preventing, inhibiting and diminishing the symptoms of *Bacillus anthracis* infection are provided. The compositions described herein uniquely overcome the activity of anthrax toxins, namely protective antigen (PA), lethal factor (LF) and edema factor (EF). More particularly, the compositions include immunogenic compositions containing peptides, or epitopes corresponding to antigenic regions of *Bacillus anthracis*, or active fragments thereof, optionally combined with delivery vehicles or carrier polypeptide(s), including PA. In certain embodiments, the compositions include multiple epitopes corresponding to one or more antigenic regions associated with anthrax toxins. In a further embodiment, the antigenic regions associated with anthrax toxins are peptides or peptide fragments derived from PA, LF or EF that elicit an immunogenic response when administered to an animal or human. In another embodiment, the composition contains multiple peptides or fragments thereof, derived from PA, LF and/or EF that elicit an immune response when administered to an animal or human. The multiple peptides can be separate or combined, such as in a fusion protein. Though not wishing to be bound by the following theory, the compositions described herein may elicit a humoral immune response that results in prevention or reduction of *Bacillus anthracis* toxicity and infection.

The compositions provided herein contain an immunogenic anthrax peptide having a molecular weight less than 20 kDa and are therefore smaller than previously described antigenic domains contemplated for use in anthrax vaccines. The peptide is preferably 40 amino acids in length or less. The peptide is optionally coupled to a carrier, such as but not limited to, a protective antigen protein. Preferred peptides for PA are set forth in Tables 4 and 6. Preferred peptides for LF are set forth in Tables 1-3 and 5. Preferred peptides for EF are set forth in Table 7.

Preferably, the compositions described herein are useful in a method for inducing an immune response to anthrax, such as for treating, protecting against or vaccinating a human or animal against *Bacillus anthracis* the causative agent associated with anthrax.

Certain embodiments of the compositions described herein further contain delivery or carrier vehicles such as liposomes or vesicles having epitopes, epitope fragments, synthetic peptides or conservatively modified peptide fragments presented on their external surfaces. In an alternative embodiment, a desired epitope or immunogenic peptide fragment thereof, may be partially or totally encapsulated with a carrier such as a liposome. In another alternative embodiment, the epitopes or immunogenic fragment thereof or peptide may be transported to desired sites by delivery mechanisms employing the use of colloidal metals such as colloidal gold. The above described compositions are useful as vaccines to improve immunity against certain anthrax toxins, which otherwise would not be effectively targeted by the immune system.

The compositions are further useful in therapeutic regimens for reducing the debilitating effects of anthrax. Though not wishing to be bound by the following theory, it is thought that the resulting circulating antibodies bind anthrax toxins and thereby prevent the dissemination of Bacillus anthracis infection, reduce existing infection, or diminish the effects of infection.

The compositions also include isolated and recombinant antibodies specific for Bacillus anthracis antigenic epitopes. Isolated antibodies are produced by and purified from humans or animals with strong primed immune responses and injected into humans or animals with weak, non-functional or non-primed immune systems in need of such circulating antibodies. The antibodies are either produced by administering one or more of the peptides described herein to an animal and then collecting, purifying and modifying the antibodies as needed or by affinity purifying protective, anti-peptide responses from animals immunized with proteins/protein fragments/peptides, vaccinated individuals or survivors of anthrax infection. These affinity purified antibodies can be sequenced and produced recombinantly for use as immunotherapeutics. The antibodies may be monoclonal or polyclonal antibodies. The antibodies are immunoreactive with a peptide of an anthrax protein having a molecular weight less than 20 kDa, preferably 40 amino acids in length or less, that induces an immune response to anthrax when administered to an animal. Thus, anthrax infection is reduced or inhibited either by active immunization of an individual using compositions containing unique epitopes or peptides associated with Bacillus anthracis toxins, or by passive immunization via administering an antibody or a group of antibodies specific for Bacillus anthracis toxins. The antibody may be modified to reduce adverse effects when administered to a patient. Humanized antibodies are ideal for this use.

Alternatively, the antibodies or peptides are used as reagents in a method, such as an immunoassay. The antibody or peptide reagent is combined with a sample from a potentially infected animal or human, and the formation of an antibody-antigen complex is detected. The immunoassay is useful for detecting anthrax infection in an animal or human, either by detecting circulating antibodies or by detecting anthrax proteins. Alternatively, the immunoassay is useful for detecting specific protective immunity to anthrax infection in an animal or human. If predetermined anti-anthrax antibody titers are detected, then the animal should be protected against anthrax challenge, and subsequent vaccinations or boosting may be unnecessary.

Accordingly, it is an object of the present invention to provide methods and compositions for preventing and reducing the effects of infection caused by Bacillus anthracis.

It is another object of the present invention to provide methods and compositions for preventing, reducing and treating the occurrence or spread of anthrax.

It is a further object of the present invention to provide methods and compositions for preventing and reducing the effects of infection caused by Bacillus anthracis in a human or animal having such an infection by eliciting an active humoral and/or cellular response in the host.

It is yet another object of the present invention to provide methods and compositions for vaccinating a human or animal against Bacillus anthracis infection.

It is yet another object of the present invention to provide methods and compositions for passively immunizing a human or animal against Bacillus anthracis infection.

Another object of the present invention is to provide compositions containing unique epitopes associated with Bacillus anthracis toxins that are antigenic and elicit an immune response against Bacillus anthracis in humans or animals.

Another object of the present invention is to provide compositions containing unique epitopes associated with Bacillus anthracis toxins that are antigenic and elicit an immune response against Bacillus anthracis in humans or animals wherein the toxin is protective antigen, lethal factor, or edema factor, individually or in combination.

Yet another object of the present invention is to provide Bacillus anthracis epitopes or peptide fragments modified with antigenic moieties to increase an individual's response to Bacillus anthracis and methods of use thereof.

Another object of the present invention is to provide antibodies useful for passively immunizing a human or animal against anthrax.

These and other objects, features and advantages of the present invention will become apparent after a review of the following detailed description of the disclosed embodiment and the appended claims.

The compositions and method described herein may be understood more readily by reference to the following detailed description of specific embodiments included herein. Although the present invention has been described with reference to specific details of certain embodiments thereof, it is not intended that such details should be regarded as limitations upon the scope of the invention.

BRIEF DESCRIPTION OF THE FIGURES

FIG. 2 is a flow chart providing study details for generation of anti-LF and anti-PA antisera containing neutralizing antibodies in mice.

FIG. 4 is a flow chart providing study design for lethal toxin challenge.

FIGS. 9A-C provide data of lethal factor epitopes in A/J, B6 and B6.H2$^k$ mice.

FIGS. 10A-C provide data of protective antigen epitopes in A/J, B6 and B6.H2$^k$ mice.

FIGS. 12A-C provide data of sequential human B cell protective antigen antibodies.

FIG. 13 provides a table of human protective antigen humoral epitopes.

FIG. 14 provides FIGS. 14A-C provide data of sequential human B cell lethal factor humoral epitopes.

FIG. 15 provides a table of human lethal factor humoral epitopes.

FIGS. 17A and B provide results of anti-EF IgG antibody titers in immunized A/J mice.

FIGS. 18A and B provide results of lethal edema toxin challenge in EF-immunized A/J mice.

FIGS. 19 A and B provide data of sequential mouse B cell epitopes of EF.

FIGS. 20A-C provide data showing that peptide-binding antibodies purified from PA- and LF-immunized mice can neutralize the action of lethal toxin in vitro.

FIGS. 21A and B provide graphs showing IgG anti-PA peptide concentration and percent viability.

FIGS. 23A-D provide data showing that some peptide-binding antibodies from human AVA vaccines can neutralize the action of lethal toxin in vitro.

DETAILED DESCRIPTION OF THE PRESENT INVENTION

Figure 1:
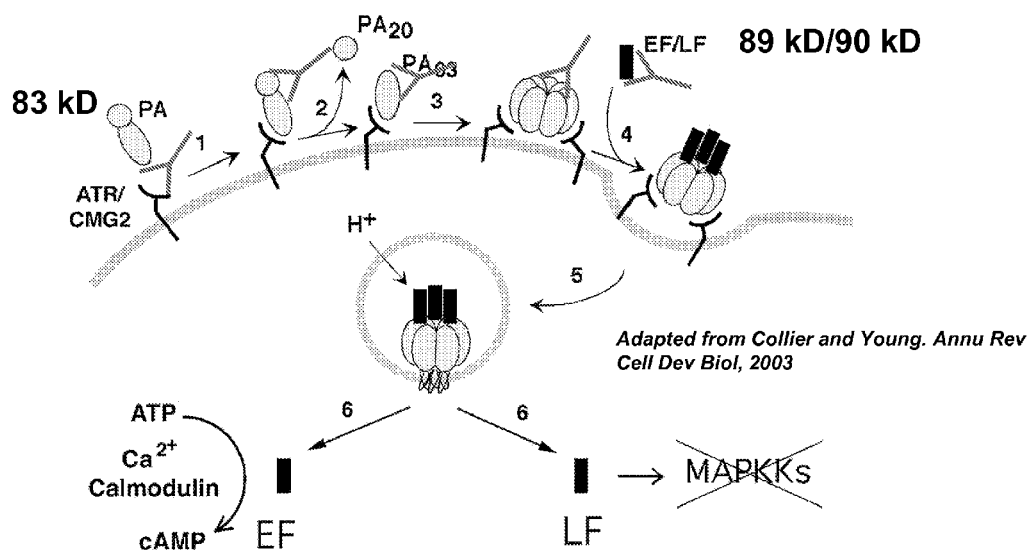
FIG. 1 provides a schematic representation of binding and processing of Bacillus anthracis virulence factors.

Immunogenic anthrax peptide compositions and methods for inducing an immune response to anthrax in a human or animal are described herein. Anti-anthrax antibodies, methods of making the antibodies, and methods for treating anthrax infection using the antibodies are also described. In addition, reagents and assays for the detection of anthrax infection are described.

The anthrax peptides provided herein are immunogenic and have a molecular weight less than 20 kDa. The peptides are portions or fragments of the immunologically important anthrax proteins known as protective antigen (PA) protein, lethal factor (LF) protein, and edema factor (EF) protein, or combinations thereof. Preferably, the amino acid sequence of each anthrax peptide is less than 40 amino acids. More preferably, the amino acid sequence is greater than six amino acids and less than 40 amino acids. Alternatively, the amino acid sequence is greater than six amino acids and less than 20 amino acids in length. In a preferred embodiment, the amino acid sequence of the anthrax peptide has a length between 12 and 18 amino acids. Alternatively, the preferred length is 8 to 10 amino acids in length. In one embodiment, the consecutive amino acid sequence of the anthrax peptide is 12 amino acids in length. Selective and representative anthrax peptide amino acid sequences are provided herein.

The antibodies provided herein are immunoreactive with anthrax proteins, particularly PA, LF or EF and are prepared by administering the anthrax peptides described herein to an animal and collecting or purifying a biological fluid from the animal containing antibodies specific for the anthrax peptides. The antibodies are administered to an animal, such as a human patient infected with anthrax, as an immunotherapy to treat the disease.

The anthrax peptides and antibodies described herein are also useful as reagents in immunoassays for the detection or diagnosis of anthrax infection.

Nucleic acid sequences that encode the anthrax peptides described herein are also contemplated within the scope of the invention. These nucleic acid sequences are useful for production of the anthrax peptides. The nucleic acid sequences are also useful as a DNA vaccine and can be inserted into a vector to transfect animals or humans to introduce the antigenic epitope or peptide into the system, thereby causing the body to mount an immune response to the immunogenic peptide.

DEFINITIONS

The terms "a", "an" and "the" as used herein are defined to mean one or more and include the plural unless the context is inappropriate.

The terms "antibody" or "antibodies" as used herein include monoclonal antibodies, polyclonal, chimeric, single chain, bispecific, simianized, and humanized antibodies as well as Fab fragments, including the products of an Fab immunoglobulin expression library.

The term "antigen" refers to an entity or fragment thereof which can induce an immune response in a animal. The term includes immunogens and regions responsible for antigenicity or antigenic determinants.

As employed herein, the phrase "biological activity" refers to the functionality, reactivity, and specificity of compounds that are derived from biological systems or those compounds that are reactive to them, or other compounds that mimic the functionality, reactivity, and specificity of these compounds. Examples of suitable biologically active compounds include enzymes, antibodies, antigens and proteins.

The phrases "biologically pure" or "isolated" refer to material substantially or essentially free from components that normally accompany it as found in its native state. Thus, the peptides described herein do not contain materials normally associated with their in situ environment. Typically, the isolated, antiproliferative peptides described herein are at least about 80% pure, usually at least about 90% pure, and preferably at least about 95% pure as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

Preferably, the epitopes and peptides of the present invention are relatively short in length (i.e., less than about 40 amino acids). Such short amino acid sequences can be synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the antigenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the immunogenic peptide and then to cause the peptide to re-fold into the preferred conformation. Methods of reducing and denaturing proteins and inducing re-folding are well known to those of skill in the art.

The term "bodily fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions.

The term "carrier" as used herein means a structure in which a immunogen or a immunogenic peptide fragment of Bacillus anthracis toxin can be incorporated into or associated with, thereby presenting or exposing the immunogen or part of the immunogenic peptide to the immune system of a human or animal and rendering the immunogenic composition antigenic for Bacillus anthracis. The term "carrier" further comprises methods of delivery wherein immunogenic peptides or peptide fragment compositions may be transported to desired sites by delivery mechanisms.

In addition, the term "carrier" further includes vaccine delivery mechanisms known to those skilled in the art including, but not limited to, keyhole limpet hemocyanin (KLH), bovine serum albumin (BSA), tetanus toxoid, and polypeptides derived from B. anthracis, including protective antigen (PA), particularly recombinant PA, and other adjuvants. It is also to be understood that the antigenic epitope compositions provided herein can further include adjuvants, preservatives, diluents, emulsifiers, stabilizers, and other components that are known and used in vaccines. Any adjuvant system known in the art can be used in the compositions described herein. Such adjuvants include, but are not limited to, Freund's incomplete adjuvant, Freund's complete adjuvant, polydispersed β-(1,4) linked acetylated mannan, polyoxyethylene-polyoxypropylene copolymer adjuvants, modified lipid adjuvants, saponin derivative adjuvants, large polymeric anions such as dextran sulfate, and inorganic gels such as alum, aluminum hydroxide, or aluminum phosphate.

Carrier proteins, or carriers, that can be used in the antigenic peptide compositions provided herein include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; polymers of D- and/or L-amino acids; tetanus toxoid, and polypeptides derived from B. anthracis itself, particularly recombinant PA. The carrier is conjugated or otherwise covalently or non-covalently bound to the anthrax peptide.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, deletions or modifications that would substantially alter the biological activity of that peptide.

As used herein, the term "edema factor" or "EF" refers to wild-type full-length edema factor of Bacillus anthracis (See SEQ ID NO:3 and Genbank accession number: AAA79215; Robertson D L, Tippetts M T, Leppla S H. Gene. 1988 Dec. 20; 73(2):363-71).

The term "effective amount" refers to the amount of epitope or immunogenic peptide which, when administered to a human or animal, elicits an immune response, prevents, reduces or lessens Bacillus anthracis infection, causes a reduction in reactivity or inhibits the spread and proliferation of Bacillus anthracis disease. The effective amount is readily determined by one of skill in the art following routine procedures.

For example, immunogenic epitope compositions may be administered intramuscularly, parenterally, subcutaneously, via inhalation as an aerosol or orally in a range of approximately 1.0 µg to 5.0 mg per patient, though this range is not intended to be limiting. The actual amount of epitope or immunogenic peptide composition required to elicit an immune response will vary for each individual patient depending on the immunogenicity of the epitope administered and on the immune response of the individual. Consequently, the specific amount administered to an individual will be determined by routine experimentation and based upon the training and experience of one skilled in the art.

The term "epitope" as used herein means a part of a macromolecule recognized by the immune system such as a three-dimensional structural feature that binds to an antibody. Alternatively, the term "epitope" refers to a linear epitope determined by an amino acid sequence.

Also as used herein, the term "immunogenic" refers to substances that elicit or enhance the production of antibodies, T-cells and other reactive immune cells directed against Bacillus anthracis and contribute to an immune response in a human or animal. An immune response occurs when an animal or individual produces sufficient antibodies, T-cells and other reactive immune cells against compositions of the present invention to prevent, lessen or alleviate the effect of Bacillus anthracis infection.

As used herein, the term "lethal factor" or "LF" refers to wild-type full-length lethal factor of Bacillus anthracis (See SEQ ID NO:2 and Genbank accession number: AAM26117; Read T D, Salzberg S L, Pop M, Shumway M, Umayam L, Jiang L, Holtzapple E, Busch J D, Smith K L, Schupp J M, Solomon D, Keim P, Fraser C M. Science. 2002 Jun. 14; 296(5575):2028-33)).

As used herein, the term "protective antigen" or "PA" refers to the wild-type full-length protective antigen of Bacillus anthracis (See SEQ ID NO:1 and Genbank accession number: AAA22637; Welkos S L, Lowe J R, Eden-McCutchan F, Vodkin M, Leppla S H, Schmidt J J. Gene. 1988 Sep. 30; 69(2):287-300)).

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" refers to an amino acid (D or L) or an amino acid mimetic incorporated in an oligopeptide by an amide bond or amide bond mimetic. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than 5%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V); and;
6) Phenylalanine (F), Tyrosine (Y), Tryptophan (W).

Anthrax Peptide Compositions

The anthrax peptides provided herein are immunogenic portions or fragments of PA, LF, or EF *Bacillus anthracis* toxin proteins, and the peptides have a molecular weight less than 20 kDa. Each peptide contains at least one epitope of an anthrax toxin protein as described in more detail below. Preferably, the amino acid sequence of each anthrax peptide is less than 40 amino acids. In one embodiment, the amino acid sequence of the anthrax peptide is greater than six amino acids and less than 40 amino acids or 20 amino acids in length. In a preferred embodiment, the amino acid sequence of the anthrax peptide is greater than six amino acids and less than 20 amino acids in length. Most preferably, the amino acid sequence of the anthrax peptide has a length between 12 and 18 amino acids. Ideally, the anthrax peptide has a sequence between eight and 10 amino acids. Alternatively, the anthrax peptide is 12 amino acids in length.

Combinations of anthrax peptides from the same or different anthrax toxin proteins, fusion proteins containing the anthrax peptides, anthrax peptides coupled to a carrier, and conservatively modified peptides are also included within the scope of the peptides described herein. In addition, the peptides may be naturally occurring, recombinant, modified or synthetic.

Depending on their intended use, the peptides are attached to or admixed with adjuvants, excipients, preservatives, delivery vehicles, other antigenic moieties and the like to produce an immunogenic composition such as an anthrax vaccine composition. The anthrax peptides can also be modified so as to increase their antigenicity. Examples of antigenic moieties and adjuvants include, but are not limited to, lipophilic muramyl dipeptide derivatives, nonionic block polymers, aluminum hydroxide or aluminum phosphate adjuvant, and mixtures thereof.

As mentioned above, each peptide contains at least one epitope of an anthrax toxin protein. An epitope is that part of a macromolecule that is recognized by the immune system, specifically by antibodies, B cells, or T cells. An epitope is a single antigenic site on a protein against which an antibody reacts. Although usually epitopes are thought to be derived from non-self proteins, sequences derived from the host that can be recognized are also classified as epitopes. Most B cell epitopes can be thought of as three-dimensional surface features of an antigen molecule; these features fit precisely and thus bind to antibodies. The part of an antibody that recognizes the epitope is called a paratope. Sequential epitopes can be recognized by antibodies and can either be found on the surface of the molecule or partially on the surface of the molecule. The methodology used herein constructs sequential epitopes, which are synthesized in extremely high concentrations/densities on the solid phase surfaces. This approach allows the detection of antibodies which bind to a sequential sequence, and at times, even identifies two regions of binding which come together on the surface of the molecule leading to one functional epitope.

As used herein, an epitope is defined as containing a region of immunogenicity associated with at least one of the following: protective antigen, lethal factor or edema factor. In one embodiment, the epitope contains a range of consecutive amino acids that are immunogenic to protective antigen, lethal factor or edema factor. Preferably, the composition described herein contains one or more epitopes from each of these three *Bacillus anthracis* toxin proteins. More preferably, the composition contains one or more epitopes from each domain of each toxin protein, PA, LF and EF, of the *Bacillus anthracis* toxin system.

The immunogenic peptides provided herein are peptides, portions or fragments of full-length anthrax proteins. Full-length recombinant protective antigen, lethal factor and edema factor proteins are produced using a recombinant vector such as standard bacterial or Baculoviral gene expression systems. Full-length proteins can be cleaved into individual domains or digested using various methods. In addition, the amino acid sequences and domains of full length protective antigen, lethal factor and edema factor are well known in the art (see also SEQ ID NO: 1-3 and Genbank Accession Numbers AA22637, AAM26117, and AA79215, respectively). In a preferred embodiment, the composition contains one or more immunogenic peptides from each of these *Bacillus anthracis* toxin proteins.

In a preferred embodiment, the composition contains one or more immunogenic peptides from each *Bacillus anthracis* toxin protein.

In one embodiment, the peptides in the anthrax peptide composition are preferably epitopes (a) 1-9 PA (Table 6) (SEQ ID NOS: 187-195); 1-10 LF (Table 5) (SEQ ID NOS: 177-186) and 1-13 EF (Table 7) (SEQ ID NOS: 196-208) and fragments thereof for human (see FIGS. 12-15) and (b) 1-27 LF (Table 1) (SEQ ID NOS: 92-116, 47, 68); 1-28 LF (Table 2) (SEQ ID NOS: 139-151, 94-95, 97-104, 108-110, 113-114); 1-27 LF (Table 3) (SEQ ID NOS: 92-116, 47, 68); 1-25 PA (Table 4) (SEQ ID NOS: 152-176); 1-17 EF (Table 8) (SEQ ID NOS: 209-225) and 1-9 EF (Table 9) (SEQ ID NOS: 249-257) and fragments thereof for mouse. (see FIGS. 6A, 7A and 19A).

In another embodiment, the peptides are those of Tables 1-9. Preferred anthrax peptides from protective antigen include the peptide sequences of Tables 4 and 6-7.

Preferred anthrax peptides from lethal factor include the peptide sequences of Tables 1-3 and 5.

Preferred anthrax peptides from edema factor include the peptide sequences of Tables 8-10.

Preferred anthrax peptides from protective antigen and lethal factor include the peptide sequences referred to in FIGS. 13 and 15, respectively.

Highly preferred anthrax peptides are set forth in the Tables as described below:

Table 1: Mouse Summary Lethal Factor

Table 1 discloses immunogenic decapeptides and corresponding composite immunogenic peptides for mouse lethal factor. A total of 392 reactive amino acids were identified out of 810 amino acids that comprise LF. A peptide was considered reactive if the peptide was observed to have reactivity greater than or equal to 0.3 as determined by a normalized OD measurement. An extended epitope, consisting of adjacent overlapping peptides was required to contain at least one peptide demonstrating an OD of 0.4 or greater. A single reactive peptide that did not demonstrate an adjacent reactive peptide was not considered to constitute an epitope unless the OD exceeded 1.0. In total, 27 epitopes of lethal factor in the immunized murine system were identified based on this classification.

TABLE 1

| Sequence | Pin # | Composite Sequence | Length | No. on Structure |
|---|---|---|---|---|
| GAGGHGDVGM (SEQ ID NO: 4) | 17 | GAGGHGDVGMHVKEKE (SEQ ID NO: 92) | 16 | |
| GGHGDVGMHV (SEQ ID NO: 5) | 18 | | | |
| HGDVGMHVKE (SEQ ID NO: 6) | 19 | | | |
| DVGMHVKEKE (SEQ ID NO: 7) | 20 | | | |
| KEKNKDENKR (SEQ ID NO: 8) | 24 | KEKNKDENKRKD (SEQ ID NO: 93) | 12 | |
| KNKDENKRKD (SEQ ID NO: 9) | 25 | | | |
| RNKTQEEHLK (SEQ ID NO: 10) | 31 | RNKTQEEHLKEIMKHI (SEQ ID NO: 94) | 16 | |
| KTQEEHLKEI (SEQ ID NO: 11) | 32 | | | |
| QEEHLKEIMK (SEQ ID NO: 12) | 33 | | | |
| EHLKEIMKHI (SEQ ID NO: 13) | 34 | | | |
| EKVPSDVLEM (SEQ ID NO: 14) | 49 | EKVPSDVLEMYKAIGGKI (SEQ ID NO: 95) | 18 | 1 |
| VPSDVLEMYK (SEQ ID NO: 15) | 50 | | | |
| SDVLEMYKAI (SEQ ID NO: 16) | 51 | | | |
| VLEMYKAIGG (SEQ ID NO: 17) | 52 | | | |
| EMYKAIGGKI (SEQ ID NO: 18) | 53 | | | |
| SEDKKKIKDI (SEQ ID NO: 19) | 66 | SEDKKKIKDIYGKDALLHEH (SEQ ID NO: 96) | 20 | 2 |
| DKKKIKDIYG (SEQ ID NO: 20) | 67 | | | |
| KKIKDIYGKD (SEQ ID NO: 21) | 68 | | | |
| IKDIYGKDAL (SEQ ID NO: 22) | 69 | | | |
| DIYGKDALLH (SEQ ID NO: 23) | 70 | | | |
| YGKDALLHEH (SEQ ID NO: 24) | 71 | | | |
| LHEHYVYAKE (SEQ ID NO: 25) | 74 | LHEHYVYAKEGY (SEQ ID NO: 97) | 12 | |
| EHYVYAKEGY (SEQ ID NO: 26) | 75 | | | |
| SNEVQEVFAK (SEQ ID NO: 27) | 122 | SNEVQEVFAKAF (SEQ ID NO: 98) | 12 | |
| EVQEVFAKAF (SEQ ID NO: 28) | 123 | | | |
| QHRDVLQLYA (SEQ ID NO: 29) | 131 | QHRDVLQLYAPEAFNYMDKFNEQEINLSLEELKD (SEQ ID NO: 99) | 34 | 3 |
| RDVLQLYAPE (SEQ ID NO: 30) | 132 | | | |
| VLQLYAPEAF (SEQ ID NO: 31) | 133 | | | |

TABLE 1-continued

| Sequence | Pin # | Composite Sequence | Length | No. on Structure |
|---|---|---|---|---|
| QLYAPEAFNY (SEQ ID NO: 32) | 134 | | | |
| YAPEAFNYMD (SEQ ID NO: 33) | 135 | | | |
| PEAFNYMDKF (SEQ ID NO: 34) | 136 | | | |
| AFNYMDKFNE (SEQ ID NO: 35) | 137 | SPLIT INTO 26 AND 16 | | |
| NYMDKFNEQE (SEQ ID NO: 36) | 138 | | | |
| MDKFNEQEIN (SEQ ID NO: 37) | 139 | | | |
| KFNEQEINLS (SEQ ID NO: 38) | 140 | | | |
| NEQEINLSLE (SEQ ID NO: 39) | 141 | | | |
| QEINLSLEEL (SEQ ID NO: 40) | 142 | | | |
| INLSLEELKD (SEQ ID NO: 41) | 143 | | | |
| LEELKDQRML (SEQ ID NO: 42) | 145 | LEELKDQRMLAR (SEQ ID NO: 100) | 12 | |
| ELKDQRMLAR (SEQ ID NO: 43) | 146 | | | |
| MLARYEKWEK (SEQ ID NO: 44) | 149 | MLARYEKWEKIKQH (SEQ ID NO: 101) | 14 | |
| ARYEKWEKIK (SEQ ID NO: 45) | 150 | | | |
| YEKWEKIKQH (SEQ ID NO: 46) | 151 | | | |
| LLKKLQIPIE (SEQ ID NO: 47) | 163 | LLKKLQIPIE (SEQ ID NO: 47) | 10 | 4 |
| SLSQEEKELL (SEQ ID NO: 48) | 172 | SLSQEEKELLKRIQ (SEQ ID NO: 102) | 14 | 5 |
| SQEEKELLKR (SEQ ID NO: 49) | 173 | | | |
| EEKELLKRIQ (SEQ ID NO: 50) | 174 | | | |
| DFLSTEEKEF (SEQ ID NO: 51) | 181 | DFLSTEEKEFLKKLQIDI (SEQ ID NO: 103) | 18 | 6 |
| LSTEEKEFLK (SEQ ID NO: 52) | 182 | | | |
| TEEKEFLKKL (SEQ ID NO: 53) | 183 | | | |
| EKEFLKKLQI (SEQ ID NO: 54) | 184 | | | |
| EFLKKLQIDI (SEQ ID NO: 55) | 185 | | | |
| SLSEEEKELL (SEQ ID NO: 56) | 191 | SLSEEEKELLNRIQ (SEQ ID NO: 104) | 14 | 7 |
| SEEEKELLNR (SEQ ID NO: 57) | 192 | | | |
| EEKELLNRIQ (SEQ ID NO: 58) | 193 | | | |
| LSEKEKEFLK (SEQ ID NO: 59) | 201 | LSEKEKEFLKKLKLDI (SEQ ID NO: 105) | 16 | 8 |
| EKEKEFLKKL (SEQ ID NO: 60) | 202 | | | |
| EKEFLKKLKL (SEQ ID NO: 61) | 203 | | | |
| EFLKKLKLDI (SEQ ID NO: 62) | 204 | | | |
| QPYDINQRLQ (SEQ ID NO: 63) | 209 | QPYDINQRLQDT (SEQ ID NO: 106) | 12 | 9 |
| YDINQRLQDT (SEQ ID NO: 64) | 210 | | | |
| LIDSPSINLD (SEQ ID NO: 65) | 216 | LIDSPSINLDVRKQ (SEQ ID NO: 107) | 14 | 10 |
| DSPSINLDVR (SEQ ID NO: 66) | 217 | | | |
| PSINLDVRKQ (SEQ ID NO: 67) | 218 | | | |
| NRGIFNEFKK (SEQ ID NO: 68) | 249 | NRGIFNEFKK (SEQ ID NO: 68) | 10 | |
| KYSISSNYMI (SEQ ID NO: 69) | 255 | KYSISSNYMIVD (SEQ ID NO: 108) | 12 | |

TABLE 1-continued

| Sequence | Pin # | Composite Sequence | Length | No. on Structure |
|---|---|---|---|---|
| SISSNYMIVD (SEQ ID NO: 70) | 256 | | | |
| LIKKVTNYLV (SEQ ID NO: 71) | 324 | LIKKVTNYLVDG (SEQ ID NO: 109) | 12 | |
| KKVTNYLVDG (SEQ ID NO: 72) | 325 | | | |
| LVDGNGRFVF (SEQ ID NO: 73) | 328 | LVDGNGRFVFTDITLP (SEQ ID NO: 110) | 16 | 11 |
| DGNGRFVFTD (SEQ ID NO: 74) | 329 | | | |
| NGRFVFTDIT (SEQ ID NO: 75) | 330 | | | |
| RFVFTDITLP (SEQ ID NO: 76) | 331 | | | |
| QYTHQDEIYE (SEQ ID NO: 77) | 338 | QYTHQDEIYEQV (SEQ ID NO: 111) | 12 | 12 |
| THQDEIYEQV (SEQ ID NO: 78) | 339 | | | |
| VPESRSILLH (SEQ ID NO: 79) | 347 | VPESRSILLHGP (SEQ ID NO: 112) | 12 | |
| ESRSILLHGP (SEQ ID NO: 80) | 348 | | | |
| DSEGFIHEFG (SEQ ID NO: 81) | 357 | DSEGFIHEFGHAVD (SEQ ID NO: 113) | 14 | |
| EGFIHEFGHA (SEQ ID NO: 82) | 358 | | | |
| FIHEFGHAVD (SEQ ID NO: 83) | 359 | | | |
| NSKKFIDIFK (SEQ ID NO: 84) | 372 | NSKKFIDIFKEE (SEQ ID NO: 114) | 12 | |
| KKFIDIFKEE (SEQ ID NO: 85) | 373 | | | |
| DHAERLKVQK (SEQ ID NO: 86) | 391 | DHAERLKVQKNAPKTF (SEQ ID NO: 115) | 16 | |
| AERLKVQKNA (SEQ ID NO: 87) | 392 | | | |
| RLKVQKNAPK (SEQ ID NO: 88) | 393 | | | |
| KVQKNAPKTF (SEQ ID NO: 89) | 394 | | | |
| PKTFQFINDQ (SEQ ID NO: 90) | 397 | PKTFQFINDQIK (SEQ ID NO: 116) | 12 | |
| TFQFINDQIK (SEQ ID NO: 91) | 398 | | | |

Table 2: Extended Mouse Summary Lethal Factor

Table 2 discloses immunogenic decapeptides and corresponding composite immunogenic peptides for mouse lethal factor wherein; the peptides and composite sequences were considered reactive if the peptide reactivity was greater than 0.2 as determined by optical density measurement. Each extended epitope (denoted as composite sequence) was required to contain at least one decapeptide demonstrating an optical density (O.D.) of greater than or equal to 0.4. In this instance, 440 reactive amino acid were identified out of a total of 810 amino acids comprising LF. In total, 28 epitopes were identified based on this classification.

TABLE 2

| Sequence | Pin # | Composite Sequence | Length |
|---|---|---|---|
| VQGAGGHGDV (SEQ ID NO: 117) | 16 | VQGAGGHGDVGMHVKEKE (SEQ ID NO: 139) | 18 |
| GAGGHGDVGM (SEQ ID NO: 4) | 17 | | |
| GGHGDVGMHV (SEQ ID NO: 5) | 18 | | |
| HGDVGMHVKE (SEQ ID NO: 6) | 19 | | |
| DVGMHVKEKE (SEQ ID NO: 7) | 20 | | |
| KEKEKNKDEN (SEQ ID NO: 118) | 23 | KEKEKNKDENKRKD (SEQ ID NO: 140) | 14 |
| KEKNKDENKR (SEQ ID NO: 8) | 24 | | |

TABLE 2-continued

| Sequence | Pin # | Composite Sequence | Length |
|---|---|---|---|
| KNKDENKRKD (SEQ ID NO: 9) | 25 | | |
| KRKDEERNKT (SEQ ID NO: 119) | 28 | KRKDEERNKTQE (SEQ ID NO: 141) | 12 |
| KDEERNKTQE (SEQ ID NO: 120) | 29 | | |
| RNKTQEEHLK (SEQ ID NO: 10) | 31 | RNKTQEEHLKEIMKHI (SEQ ID NO: 94) | 16 |
| KTQEEHLKEI (SEQ ID NO: 11) | 32 | | |
| QEEHLKEIMK (SEQ ID NO: 12) | 33 | | |
| EHLKEIMKHI (SEQ ID NO: 13) | 34 | | |
| EKVPSDVLEM (SEQ ID NO: 14) | 49 | EKVPSDVLEMYKAIGGKI (SEQ ID NO: 95) | 18 |
| VPSDVLEMYK (SEQ ID NO: 15) | 50 | | |
| SDVLEMYKAI (SEQ ID NO: 16) | 51 | | |
| VLEMYKAIGG (SEQ ID NO: 17) | 52 | | |
| EMYKAIGGKI (SEQ ID NO: 18) | 53 | | |
| ISLEALSEDK (SEQ ID NO: 121) | 63 | ISLEALSEDKKKIKDIYGKDALLHEH (SEQ ID NO: 142) | 26 |
| LEALSEDKKK (SEQ ID NO: 122) | 64 | | |
| ALSEDKKKIK (SEQ ID NO: 123) | 65 | | |
| SEDKKKIKDI (SEQ ID NO: 19) | 66 | | |
| DKKKIKDIYG (SEQ ID NO: 20) | 67 | | |
| KKIKDIYGKD (SEQ ID NO: 21) | 68 | | |
| IKDIYGKDAL (SEQ ID NO: 22) | 69 | | |
| DIYGKDALLH (SEQ ID NO: 23) | 70 | | |
| YGKDALLHEH (SEQ ID NO: 24) | 71 | | |
| LHEHYVYAKE (SEQ ID NO: 25) | 74 | LHEHYVYAKEGY (SEQ ID NO: 97) | 12 |
| EHYVYAKEGY (SEQ ID NO: 26) | 75 | | |
| DFSVEFLEQN (SEQ ID NO: 124) | 117 | not included | |
| SNEVQEVFAK (SEQ ID NO: 27) | 122 | SNEVQEVFAKAF (SEQ ID NO: 98) | 12 |
| EVQEVFAKAF (SEQ ID NO: 28) | 123 | | |
| QHRDVLQLYA (SEQ ID NO: 29) | 131 | QHRDVLQLYAPEAFNYMDKFNEQEINLSLEELKD (SEQ ID NO: 99) | 34 |
| RDVLQLYAPE (SEQ ID NO: 30) | 132 | | |
| VLQLYAPEAF (SEQ ID NO: 31) | 133 | | |
| QLYAPEAFNY (SEQ ID NO: 32) | 134 | | |
| YAPEAFNYMD (SEQ ID NO: 33) | 135 | | |
| PEAFNYMDKF (SEQ ID NO: 34) | 136 | | |
| AFNYMDKFNE (SEQ ID NO: 35) | 137 | SPLIT INTO 26 AND 16 | |
| NYMDKFNEQE (SEQ ID NO: 36) | 138 | | |
| MOKENEQEIN (SEQ ID NO: 37) | 139 | | |
| KFNEQEINLS (SEQ ID NO: 38) | 140 | | |
| NEQEINLSLE (SEQ ID NO: 39) | 141 | | |
| QEINLSLEEL (SEQ ID NO: 40) | 142 | | |

TABLE 2-continued

| Sequence | Pin # | Composite Sequence | Length |
|---|---|---|---|
| INLSLEELKD (SEQ ID NO: 41) | 143 | | |
| LEELKDQRML (SEQ ID NO: 42) | 145 | LEELKDQRMLAR (SEQ ID NO: 100) | 12 |
| ELKDQRMLAR (SEQ ID NO: 43) | 146 | | |
| MLARYEKWEK (SEQ ID NO: 44) | 149 | MLARYEKWEKIKQH (SEQ ID NO: 101) | 14 |
| ARYEKWEKIK (SEQ ID NO: 45) | 150 | | |
| YEKWEKIKQH (SEQ ID NO: 46) | 151 | | |
| SEEGRGLLKK (SEQ ID NO: 274) | 160 | not included | |
| LLKKLQIPIE (SEQ ID NO: 47) | 163 | LLKKLQIPIEPK (SEQ ID NO: 144) | 12 |
| KKLQIPIEPK (SEQ ID NO: 125) | 164 | | |
| SLSQEEKELL (SEQ ID NO: 48) | 172 | SLSQEEKELLKRIQ (SEQ ID NO: 102) | 14 |
| SQEEKELLKR (SEQ ID NO: 49) | 173 | | |
| EEKELLKRIQ (SEQ ID NO: 50) | 174 | | |
| DFLSTEEKEF (SEQ ID NO: 51) | 181 | DFLSTEEKEFLKKLQIDI (SEQ ID NO: 103) | 18 |
| LSTEEKEFLK (SEQ ID NO: 52) | 182 | | |
| TEEKEFLKKL (SEQ ID NO: 53) | 183 | | |
| EKEFLKKLQI (SEQ ID NO: 54) | 184 | | |
| EFLKKLQIDI (SEQ ID NO: 55) | 185 | | |
| SLSEEEKELL (SEQ ID NO: 56) | 191 | SLSEEEKELLNRIQ (SEQ ID NO: 104) | 14 |
| SEEEKELLNR (SEQ ID NO: 57) | 192 | | |
| EEKELLNRIQ (SEQ ID NO: 58) | 193 | | |
| LSEKEKEFLK (SEQ ID NO: 59) | 201 | LSEKEKEFLKKLKLDIQP (SEQ ID NO: 143) | 18 |
| EKEKEFLKKL (SEQ ID NO: 60) | 202 | | |
| EKEFLKKLKL (SEQ ID NO: 61) | 203 | | |
| EFLKKLKLDI (SEQ ID NO: 62) | 204 | | |
| LKKLKLDIQP (SEQ ID NO: 126) | 205 | | |
| DIQPYDINQR (SEQ ID NO: 127) | 208 | DIQPYDINQRLQDTGG (SEQ ID NO: 145) | 16 |
| QPYDINQRLQ (SEQ ID NO: 63) | 209 | | |
| YDINQRLQDT (SEQ ID NO: 64) | 210 | | |
| INQRLQDTGG (SEQ ID NO: 128) | 211 | | |
| LIDSPSINLD (SEQ ID NO: 65) | 216 | LIDSPSINLDVRKQYKRD (SEQ ID NO: 146) | 18 |
| DSPSINLDVR (SEQ ID NO: 66) | 217 | | |
| PSINLDVRKQ (SEQ ID NO: 67) | 218 | | |
| INLDVRKQYK (SEQ ID NO: 129) | 219 | | |
| LDVRKQYKRD (SEQ ID NO: 130) | 220 | | |
| NRGIFNEFKK (SEQ ID NO: 68) | 249 | NRGIFNEFKKNF (SEQ ID NO: 147) | 12 |
| GIFNEFKKNF (SEQ ID NO: 131) | 250 | | |
| KYSISSNYMI (SEQ ID NO: 69) | 255 | KYSISSNYMIVD (SEQ ID NO: 108) | 12 |
| SISSNYMIVD (SEQ ID NO: 70) | 256 | | |

TABLE 2-continued

| Sequence | Pin # | Composite Sequence | Length |
|---|---|---|---|
| LIKKVTNYLV (SEQ ID NO: 71) | 324 | LIKKVTNYLVDG (SEQ ID NO: 109) | 12 |
| KKVTNYLVDG (SEQ ID NO: 72) | 325 | | |
| LVDGNGRFVF (SEQ ID NO: 73) | 328 | LVDGNGRFVFTDITLP (SEQ ID NO: 110) | 16 |
| DGNGRFVFTD (SEQ ID NO: 74) | 329 | | |
| NGRFVFTDIT (SEQ ID NO: 75) | 330 | | |
| RFVFTDITLP (SEQ ID NO: 76) | 331 | | |
| NIAEQYTHQD (SEQ ID NO: 132) | 336 | not included | |
| QYTHQDEIYE (SEQ ID NO: 77) | 338 | QYTHQDEIYEQVHSKG (SEQ ID NO: 148) | 16 |
| THQDEIYEQV (SEQ ID NO: 78) | 339 | | |
| QDEIYEQVHS (SEQ ID NO: 133) | 340 | | |
| EIYEQVHSKG (SEQ ID NO: 134) | 341 | | |
| VPESRSILLH (SEQ ID NO: 79) | 347 | VPESRSILLHGPSKGV (SEQ ID NO: 149) | 16 |
| ESRSILLHGP (SEQ ID NO: 80) | 348 | | |
| RSILLHGPSK (SEQ ID NO: 135) | 349 | | |
| ILLHGPSKGV (SEQ ID NO: 136) | 350 | | |
| DSEGFIHEFG (SEQ ID NO: 81) | 357 | DSEGFIHEFGHAVD (SEQ ID NO: 113) | 14 |
| EGFIHEFGHA (SEQ ID NO: 82) | 358 | | |
| FIHEFGHAVD (SEQ ID NO: 83) | 359 | | |
| NSKKFIDIFK (SEQ ID NO: 84) | 372 | NSKKFIDIFKEE (SEQ ID NO: 114) | 12 |
| KKFIDIFKEE (SEQ ID NO: 85) | 373 | | |
| DHAERLKVQK (SEQ ID NO: 86) | 391 | DHAERLKVQKNAPKTFQF (SEQ ID NO: 150) | 18 |
| AERLKVQKNA (SEQ ID NO: 87) | 392 | | |
| RLKVQKNAPK (SEQ ID NO: 88) | 393 | | |
| KVQKNAPKTF (SEQ ID NO: 89) | 394 | | |
| QKNAPKTFQF (SEQ ID NO: 137) | 395 | | |
| PKTFQFINDQ (SEQ ID NO: 90) | 397 | PKTFQFINDQIKFI (SEQ ID NO: 151) | 14 |
| TFQFINDQIK (SEQ ID NO: 91) | 398 | | |
| QFINDQIKFI (SEQ ID NO: 138) | 399 | | |

Table 3: Additional Mouse Lethal Factor Data

Table 3 discloses immunogenic decapeptides and corresponding composite immunogenic peptides for mouse lethal factor. A total of 392 reactive amino acids were identified out of 810 amino acids that comprise LF. A peptide was considered reactive if the peptide was observed to have reactivity greater than or equal to 0.2 as determined by a normalized OD measurement. An extended epitope, consisting of adjacent overlapping peptides was required to contain at least one peptide demonstrating an OD of 0.4 or greater. A single reactive peptide that did not demonstrate an adjacent reactive peptide was not considered to constitute an epitope unless the OD exceeded 1.0. In total, 27 epitopes of lethal factor in the immunized murine system were identified based on this classification.

TABLE 3

| Epitope number | Pin # | Sequence |
|---|---|---|
| 1 | 17-20 | GAGGHGDVGMHVKEKE (SEQ ID NO: 92) |
| 2 | 24-25 | KEKNKDENKRKD (SEQ ID NO: 93) |
| 3 | 31-34 | RNKTQEEHLKEIMKHI (SEQ ID NO: 94) |
| 4 | 49-53 | EKVPSDVLEMYKAIGGKI (SEQ ID NO: 95) |
| 5 | 66-71 | SEDKKKIKDIYGKDALLHEH (SEQ ID NO: 96) |

TABLE 3-continued

| Epitope number | Pin # | Sequence |
|---|---|---|
| 6 | 74-75 | LHEHYVYAKEGY (SEQ ID NO: 97) |
| 7 | 122-123 | SNEVQEVFAKAF (SEQ ID NO: 98) |
| 8 | 131-143 | QHRDVLQLYAPEAFNYMDKFNEQEINLSLEELKD (SEQ ID NO: 99) |
| 9 | 145-146 | LEELKDQRMLAR (SEQ ID NO: 100) |
| 10 | 149-151 | MLARYEKWEKIKQH (SEQ ID NO: 101) |
| 11 | 163 | LLKKLQIPIE (SEQ ID NO: 47) |
| 12 | 172-174 | SLSQEEKELLKRIQ (SEQ ID NO: 102) |
| 13 | 181-185 | DFLSTEEKEFLKKLQIDI (SEQ ID NO: 103) |
| 14 | 191-193 | SLSEEEKELLNRIQ (SEQ ID NO: 104) |
| 15 | 201-204 | LSEKEKEFLKKLKLDI (SEQ ID NO: 105) |
| 16 | 209-210 | QPYDINQRLQDT (SEQ ID NO: 106) |
| 17 | 216-218 | LIDSPSINLDVRKQ (SEQ ID NO: 107) |
| 18 | 249 | NRGIFNEFKK (SEQ ID NO: 68) |
| 19 | 255-256 | KYSISSNYMIVD (SEQ ID NO: 108) |
| 20 | 324-325 | LIKKVTNYLVDG (SEQ ID NO: 109) |
| 21 | 328-331 | LVDGNGRFVFTDITLP (SEQ ID NO: 110) |
| 22 | 338-339 | QYTHQDEIYEQV (SEQ ID NO: 111) |
| 23 | 347-348 | VPESRSILLHGP (SEQ ID NO: 112) |
| 24 | 357-359 | DSEGFIHEFGHAVD (SEQ ID NO: 113) |
| 25 | 372-373 | NSKKFIDIFKEE (SEQ ID NO: 114) |
| 26 | 391-394 | DHAERLKVQKNAPKTF (SEQ ID NO: 115) |
| 27 | 397-398 | PKTFQFINDQIK (SEQ ID NO: 116) |

Table 4: Mouse PA Compiled

Table 4 discloses immunogenic decapeptides and corresponding epitopes for mouse protective antigen wherein the peptides and composite sequences were considered reactive if the peptide reactivity was greater than 0.2 as determined by optical density measurement and containing at least one decapeptide with reactivity of 0.4 or greater. In this instance, 25 epitopes were identified based on this classification.

TABLE 4

| No. on Structure | Epitope Number | Pin Number | Sequence |
|---|---|---|---|
| 1 | 1 | 27-30 | FSDLNFQAPMVVTSST (SEQ ID NO: 152) |
| | 2 | 34-39 | STTGDLSIPSSELENIPSEN (SEQ ID NO: 153) |
| | 3 | 75-77 | YQRENPTEKGLDFK (SEQ ID NO: 154) |
| | 4 | 82-85 | LYWTDSQNKKEVISSD (SEQ ID NO: 155) |
| 2 | 5 | 93-99 | LKQKSSNSRKKRSTSAGPTVPD (SEQ ID NO: 156) |
| | 6 | 101-102 | GPTVPDRDNDGI (SEQ ID NO: 157) |
| | 7 | 110-111 | EGYTVDVKNKRT (SEQ ID NO: 158) |
| | 8 | 119-124 | SNIHEKKGLTKYKSSPEKWS (SEQ ID NO: 159) |
| 3 | 9 | 129-135 | TASDPYSDFEKVTGRIDKNVSP (SEQ ID NO: 160) |
| | 10 | 139 | SPEARHPLVA (SEQ ID NO: 161) |
| | 11 | 143-144 | VAAYPIVHVDME (SEQ ID NO: 162) |
| 4 | 12 | 147-151 | VDMENIILSKNEDQSTQN (SEQ ID NO: 163) |
| 5 | 13 | 168-172 | NAEVHASFFDIGGSVSAG (SEQ ID NO: 164) |
| | 14 | 199 | NTGTAPIYNV (SEQ ID NO: 165) |
| | 15 | 213-215 | AKENQLSQILAPNN (SEQ ID NO: 166) |
| | 16 | 276 | TLKEALKIAF (SEQ ID NO: 167) |
| 6 | 17 | 287-290 | GKDITEFDFNFDQQTS (SEQ ID NO: 168) |
| | 18 | 295 | QNIKNQLAEL (SEQ ID NO: 169) |
| | 19 | 304-305 | LDKIKLNAKMNI (SEQ ID NO: 170) |
| | 20 | 312-314 | KRFHYDRNNIAVGA (SEQ ID NO: 171) |
| 7 | 21 | 317-323 | AVGADESVVKEAHREVINSSTE (SEQ ID NO: 172) |
| 8 | 22 | 327 | TEGLLLNIDK (SEQ ID NO: 173) |
| | 23 | 329-331 | LLNIDKDIRKILSG (SEQ ID NO: 174) |
| | 24 | 357-359 | KLPLYISNPNYKVN (SEQ ID NO: 175) |
| | 25 | 366-377 | TKENTIINPSEN (SEQ ID NO: 176) |

Table 5. Human Lethal Factor Compiled

Table 5 discloses immunogenic decapeptides and corresponding epitopes for human lethal factor wherein the peptides and composite sequences were considered reactive if the response was greater than the average plus 2 standard deviations above controls and more than 50% of the individuals were positive for a given region. In this instance, 10 epitopes were identified based on this classification.

TABLE 5

| Epitope Number | Pin Number | Sequence |
|---|---|---|
| 1 | 3-6 | KEFIKVISMSCLVTAI (SEQ ID NO: 177) |
| 2 | 13-14 | PVFIPLVQGAGG (SEQ ID NO: 178) |
| 3 | 66-68 | SEDKKKIKDIYGKD (SEQ ID NO: 179) |
| 4 | 146-147 | ELKDQRMLARYE (SEQ ID NO: 180) |
| 5 | 294-296 | KIDTKIQEAQLNIN (SEQ ID NO: 181) |
| 6 | 298-300 | AQLNINQEWNKALG (SEQ ID NO: 182) |
| 7 | 310-312 | NVHNRYASNIVESA (SEQ ID NO: 183) |
| 8 | 333-334 | TDITLPNIAEQY (SEQ ID NO: 184) |
| 9 | 339-343 | THQDEIYEQVHSKGLYVP (SEQ ID NO: 185) |
| 10 | 389-393 | MHSTDHAERLKVQKNAPK (SEQ ID NO: 186) |

Table 6. Protective Antigen Human Epitopes Newly Identified

Table 6 discloses immunogenic decapeptides and corresponding epitopes for human protective antigen wherein the peptides and composite sequences were considered reactive if the peptide response was greater than the average plus 1.5 standard deviations above controls and more than 30% of the individuals were positive for a given region In this instance, nine epitopes were identified based on this classification.

TABLE 6

| Epitope Number | Pin Number | Sequence |
|---|---|---|
| 1 | 14-16 | IQAEVKQENRLLNE (SEQ ID NO: 187) |
| 2 | 43-44 | ENQTFQSAIWSG (SEQ ID NO: 188) |
| 3 | 49-50 | FIKVKKSDEYTF (SEQ ID NO: 189) |
| 4 | 64-66 | NKASNKIRLEKG (SEQ ID NO: 190) |
| 5 | 77-78 | NPTEKGLDFKLY (SEQ ID NO: 191) |
| 6 | 111-112 | YTVDVKNKRT (SEQ ID NO: 192) |
| 7 | 132-133 | SDFEKVTGRIDK (SEQ ID NO: 193) |
| 8 | 180-181 | STVAIDHSLSLA (SEQ ID NO: 194) |
| 9 | 218-219 | APNNYYPSKNLA (SEQ ID NO: 195) |

Table 7. Epitopes within the Protective Antigen Protein as Recognized by AVA Vaccinated Individual Sera and Stratified by Neutralization.

Table 7 discloses immunogenic decapeptides and corresponding humoral epitopes for human protective antigen when individuals were stratified based upon ability of sera to inhibit macrophage killing in an in vitro protection assay. Epitopes were considered reactive if the peptide response was greater than the average plus 2 standard deviations above controls and more than 30% of the individuals were positive for a given response. Using this methodology, we were able to identify 1 unique epitope within the low responders, 7 unique epitopes within the medium responders, and 5 unique epitopes within the high responders for a total of 13 epitopes.

TABLE 7

| Epitope No.[a] | A.A. No.[b] | Sequence | Domain | Function |
|---|---|---|---|---|
| 1 | 95-106 | SGFIKVKKSDEY (SEQ ID NO: 196) | I | PA20 |
| 2 | 131-144 | NSNKIRLEKGRLYQ (SEQ ID NO: 197) | I | PA20 |
| 3 | 153-172 | NPTEKGLDFKLYWTDSQNKK (SEQ ID NO: 198) | I | PA20 |
| 4 | 181-200 | QLPELKQKSSNSRKKRSTSA (SEQ ID NO: 199) | I/I' | Furin Cleavage |
| 5 | 221-234 | YTVDVKINKRTFLSP (SEQ ID NO: 200) | I' | Ligand binding |
| 6 | 261-275 | PYSDFEKVTGRIDKNV (SEQ ID NO: 201) | I' | Ligand binding |
| 7 | 313-326 | SETRTISKNTSTSR (SEQ ID NO: 202) | II | Translocation |
| 8 | 3450362 | IGGSVSAGFSNSNSSTVA (SEQ ID NO: 203) | II | Translocation |
| 9 | 389-398 | LNANIRYVNT (SEQ ID NO: 204) | II | Translocation |
| 10 | 435-448 | APNNYYPSKNLAPI (SEQ ID NO: 205) | II | Translocation |
| 11 | 585-596 | QQTSQNIKNQLA (SEQ ID NO: 206) | III | Heptamerization |
| 12 | 657-666 | LLNIDKDIRK (SEQ ID NO: 207) | IV | Receptor binding |
| 13 | 753-762 | ILIFSKKGYE (SEQ ID NO: 208) | IV | Receptor binding |

[a]Epitope number as defined in FIG. 23A
[b]Pubmed accession number AAA 22637

Table 8. Edema Factor Human Compiled

Table 8 discloses immunogenic decapeptides and corresponding epitopes for human edema factor wherein the peptides and composite sequences were considered reactive if the peptide response was greater than the average plus 2 standard deviations above controls and more than 60% of the individuals were positive for a given region. In this instance, 17 epitopes were identified based on this classification.

TABLE 8

| Epitope Number | Pin Number | Sequence |
|---|---|---|
| 1 | 3-4 | KFIPNKFSIISF (SEQ ID NO: 209) |
| 2 | 70-71 | SRFVFEKKRETP (SEQ ID NO: 210) |
| 3 | 192-193 | GNLENKKSITEH (SEQ ID NO: 211) |
| 4 | 200-201 | GKIPLKLDHLRI (SEQ ID NO: 212) |
| 5 | 208-209 | ENGIIKGKKEI (SEQ ID NO: 213) |
| 6 | 233-237 | VLGEKFNWRNIEVMAKNV (SEQ ID NO: 214) |
| 7 | 239-243 | VMAKNVEGVLKPLTADYD (SEQ ID NO: 215) |
| 8 | 252-255 | TEIKKQIPTKRMDKVV (SEQ ID NO: 216) |
| 9 | 261-264 | PNSLEKQKGVTNLLIK (SEQ ID NO: 217) |
| 10 | 266-267 | TNLLIKYGIERK (SEQ ID NO: 218) |

TABLE 8-continued

| Epitope Number | Pin Number | Sequence |
|---|---|---|
| 11 | 274-280 | KTLSNWQKQMLDRLNEAVKYT (SEQ ID NO: 219) |
| 12 | 333-335 | FIKNLSSIRRSSNV (SEQ ID NO: 220) |
| 13 | 358 | FSQEKKRKIS (SEQ ID NO: 221) |
| 14 | 373-376 | APEYKNYFQYLKERIT (SEQ ID NO: 222) |
| 15 | 381-383 | NQVQLLTHQKSNI (SEQ ID NO: 223) |
| 16 | 385-386 | HQKSNIEFKLLY (SEQ ID NO: 224) |
| 17 | 394-395 | ENETDNFEVFQK (SEQ ID NO: 225) |

Table 9. Mouse Summary Edema Factor

Table 9 discloses immunogenic decapeptides and corresponding composite immunogenic peptides for mouse Edema Factor wherein the peptides and composite sequences were considered reactive if the peptide reactivity was greater than 0.16 as determined by optical density measurement. Each extended epitope (denoted as composite sequence was required to contain at least one decapeptide demonstrating an optical density (O.D.) of greater than or equal to 0.3. In this instance, 118 reactive amino acids were identified out of a total of 800 amino acids comprising EF. In total, 9 epitopes were identified based on this classification.

TABLE 9

| Sequence | Pin # | Composite Sequence | Length | Epitope Number |
|---|---|---|---|---|
| knsmnsrgek (SEQ ID NO: 226) | 63 | KNSMNSRGEKVPFASRFV (SEQ ID NO: 249) | 18 | 1 |
| smnsrgekvp (SEQ ID NO: 227) | 64 | | | |
| nsrgekvpfa (SEQ ID NO: 228) | 65 | | | |
| rgekvpfasr (SEQ ID NO: 229) | 66 | | | |
| ekvpfasrfv (SEQ ID NO: 230) | 67 | | | |
| Yainseqske (SEQ ID NO: 231) | 80 | YAINSEQSKEVY (SEQ ID NO: 250) | 12 | 2 |
| Inseqskevy (SEQ ID NO: 232) | 81 | | | |
| Ssdllfsqkf (SEQ ID NO: 233) | 103 | SSDLLFSQKFKE (SEQ ID NO: 251) | 12 | 3 |
| Dllfsqkfke (SEQ ID NO: 234) | 104 | | | |
| Lelyapdmfe (SEQ ID NO: 235) | 129 | LELYAPDMFEYM (SEQ ID NO: 252) | 12 | 4 |
| Lyapdmfeym (SEQ ID NO: 236) | 130 | | | |
| Egeigkiplk (SEQ ID NO: 237) | 198 | EGEIGKIPLKLD (SEQ ID NO: 253) | 12 | 5 |

TABLE 9-continued

| Sequence | Pin # | Composite Sequence | Length | Epitope Number |
|---|---|---|---|---|
| Eigkiplkld (SEQ ID NO: 238) | 199 | | | |
| Dydlfalaps (SEQ ID NO: 239) | 246 | DYDLFALAPSLT (SEQ ID NO: 254) | 12 | 6 |
| Dlfalapsit (SEQ ID NO: 240) | 247 | | | |
| Nwqkqmldrl (SEQ ID NO: 241) | 276 | NWQKQMLDRLNEAV (SEQ ID NO: 255) | 14 | 7 |
| Qkqmldrlne (SEQ ID NO: 242) | 277 | | | |
| Qmldrlneav (SEQ ID NO: 243) | 278 | | | |
| Neavkytgyt (SEQ ID NO: 244) | 281 | NEAVKYTGYTGG (SEQ ID NO: 256) | 12 | 8 |
| Avkytgytgg (SEQ ID NO: 245) | 282 | | | |
| Qdneefpekd (SEQ ID NO: 246) | 291 | QDNEEFPEKDNEIF (SEQ ID NO: 257) | 14 | 9 |
| Neefpekdne (SEQ ID NO: 247) | 292 | | | |
| Efpekdneif (SEQ ID NO: 248) | 293 | | | |

Table 10: Additional Mouse Edema Factor Data

Table 10 discloses immunogenic decapeptides and corresponding epitopes for mouse edema factor wherein the peptides and composite sequences were considered reactive if the peptide reactivity was greater than 0.16 as determined by optical density measurement and containing at least one decapeptide with reactivity of 0.3 or greater. In this instance, 9 epitopes were identified based on this classification.

TABLE 10

| Epitope Number on structure | Pin Numbers | Amino acid # AAA79215 | AA Sequence |
|---|---|---|---|
| 1 | 63-67 | 125-142 | KNSMNSRGEKVPFASRFV (SEQ ID NO: 249) |
| 2 | 80-81 | 159-170 | YAINSEQSKEVY (SEQ ID NO: 250) |
| 3 | 103-104 | 205-216 | SSDLLFSQKFKE (SEQ ID NO: 251) |
| 4 | 129-130 | 257-268 | LELYAPDMFEYM (SEQ ID NO: 252) |
| 5 | 198-199 | 395-406 | EGEIGKIPLKLD (SEQ ID NO: 253) |
| 6 | 246-247 | 491-502 | DYDLFALAPSLT (SEQ ID NO: 254) |
| 7 | 276-278 | 551-564 | NWQKQMLDRLNEAV (SEQ ID NO: 255) |
| 8 | 281-282 | 561-572 | NEAVKYTGYTGG (SEQ ID NO: 256) |
| 9 | 291-293 | 581-594 | QDNEEFPEKDNEIF (SEQ ID NO: 257) |

Anthrax Peptide Formulations

One or more of the anthrax peptides can be prepared in a physiologically acceptable formulation, such as in a pharmaceutically acceptable carrier, using known techniques. For example, the peptide is combined with a pharmaceutically acceptable excipient to form a therapeutic composition.

Alternatively, the gene or nucleic acid sequence encoding the peptide may be delivered in a vector for continuous administration using gene therapy techniques. The compositions provided herein may be administered in the form of a solid, liquid or aerosol. Examples of solid compositions include pills, creams, and implantable dosage units. Pills may be administered orally. Therapeutic creams may be administered topically. Implantable dosage units may be administered locally, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal or parenteral (for example, intravenous, subcutaneous, or intramuscular) routes. In addition, the composition may be incorporated into a sustained release matrix or matrices such as biodegradable polymers, the polymers being implanted in the vicinity of where delivery is desired. The method includes administration of a single dose, administration of repeated doses at predetermined time intervals, and sustained administration for a predetermined period of time.

A sustained release matrix, as used herein, is a matrix made of materials, usually polymers that are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Alternatively, the immunogenic anthrax peptide can be inserted into a carrier, such as a membranous carrier, so as to present on the carrier surface immunogenic regions of protective antigen, lethal factor and/or edema factor. Protective antigen, lethal factor and edema factor are all immunogenic because they are recognized by the immune system as "non-self." However, inserting less than whole protective antigen, lethal factor and edema factor toxin onto the surface of liposomes may alter the presentation of the epitope to the immune system, and in some cases, may render the epitope less immunogenic.

Immunogenic liposomes may be made by reconstituting liposomes in the presence of purified or partially purified protective antigen, lethal factor and edema factor. Additionally, protective antigen, lethal factor and/or edema factor peptides may be reconstituted into liposomes. Liposomes that can be used in the compositions include those known to one skilled in the art. Any of the standard lipids useful for making liposomes may be used. Standard bilayer and multi-layer liposomes may be used to make compositions of the present invention.

The dosage of the composition will depend on the progression of infection, the particular composition used, and other clinical factors such as weight and condition of the patient, and the route of administration.

Anti-Anthrax Antibody Compositions

Anthrax peptides having the characteristics set forth above are used for the production of both monoclonal and polyclonal antibodies reactive with anthrax proteins. The compositions containing the immunogenic peptides produce monoclonal or polyclonal antibodies specifically immunoreactive with protective antigen, lethal factor and/or edema factor. Antibodies are made by methods well known to those of ordinary skill in the art.

The immunogenic anthrax peptide compositions and anti-LF, -EF and -PA antibodies are administered to a human or animal by any appropriate means, preferably by injection. For example, immunogenic peptides of protective antigen, lethal factor and edema factor are administered by subcutaneous or intramuscular injection. Whether internally produced or provided from external sources, the circulating anti-LF, -PA or -EF antibodies bind to appropriate receptors and reduce or inactivate *Bacillus anthracis*' ability to stimulate infection and disease.

The preferred antibody is a monoclonal antibody, due to its higher specificity for analyte. Monoclonal antibodies are generated by methods well known to those skilled in the art. The preferred method is a modified version of the method of Kearney, et al., *J. Immunol.* 123:1548-1558 (1979). Briefly, animals such as mice or rabbits are inoculated with the immunogen in adjuvant, and spleen cells are harvested and mixed with a myeloma cell line, such as P3X63Ag8,653. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce anti-anthrax monoclonal antibodies. Hybridomas producing antibodies are cloned, expanded and stored frozen for future production.

The anti-anthrax antibodies described herein are useful both as therapeutic compositions for the treatment of anthrax infection and as reagents in immunoassays for the detection or diagnosis of anthrax infection. The antibodies can be modified according to their designed use.

Anti-anthrax antibodies for use as a therapeutic treatment to be administered to an animal or human patient infected with anthrax may be modified so that the antibody is more easily tolerated and has fewer adverse side effect. For example, the antibodies may be modified to become hybrid, chimeric or altered antibodies as known to those skilled in the art and described in U.S. Pat. No. 6,331,415. Preferably, the antibodies are "humanized" in accordance with methods known to those skilled in the art. The humanized antibodies, such as humanized monoclonal antibodies, are produced from immunogenic sequences of patients that target key epitopes of protective antigen, lethal factor and/or edema factor. The immunogenic sequences can be used to prevent toxin formation in those individuals already infected with anthrax. These anti-anthrax antibodies are also administered to individuals to passively immunize them against *Bacillus anthracis* and thereby prevent the initiation of infection, reduce reactivity or inhibit the proliferation of *Bacillus anthracis*. When administered to individuals, the anti-LF, -EF and -PA antibodies bind to *Bacillus anthracis*, thereby reducing the effective circulating concentration of *Bacillus anthracis* toxins. Consequently, *Bacillus anthracis* toxin-dependent infection is prevented, reduced or inhibited.

If the antibody is intended for use as a reagent in an immunoassay for the detection of anthrax toxin, such as for the detection of anthrax infection in a patient, the antibody may be modified so that it can be directly or indirectly detection. For example, the antibody may be labeled directly with a detectable label for identification and quantitation of anthrax protein. Labels for use in immunoassays are generally known to those skilled in the art and include enzymes, radioisotopes, and fluorescent, luminescent and chromogenic substances including colored particles such as colloidal gold and latex beads.

Alternatively, the antibody may be labeled indirectly by reaction with labeled substances that have an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Diseases and Conditions to be Treated

The anthrax peptide compositions described herein are useful for treating, preventing, lessening or alleviating disease, symptoms and complications of *Bacillus anthracis* infection. The compositions described herein are particularly useful as a prophylactic against the causative agent of anthrax and are especially useful as a vaccine against *Bacillus anthracis*. The compositions are especially useful for treating or preventing *Bacillus anthracis* by producing neutralizing antibodies directed against the toxin components protective antigen, lethal factor and edema factor. The anti-anthrax antibody compositions described herein are useful for providing an immunotherapeutic agent for the treatment of anthrax infection.

Administration of the compositions provided herein to a human or animal infected with *Bacillus anthracis* is useful for reducing or alleviating the symptoms and immunogenic reaction of the infection.

Administration of the compositions provided herein to a human or animal at risk of being exposed to *Bacillus anthracis* is useful for preventing, reducing or alleviating the symptoms and immunogenic reaction of the infection. Compositions containing immunogenic peptides of protective antigen, lethal factor and/or edema factor are administered to a human or animal to induce immunity to *Bacillus anthracis*. The immunized human or animal develops circulating antibodies against *Bacillus anthracis* which bind to corresponding regions of protective antigen, lethal factor and edema factor, thereby reducing or inactivating its ability to stimulate *Bacillus anthracis* infection.

Antibodies and Immunoassay Detection Methods

Anthrax peptides, antibodies, methods, and kits for the detection of *Bacillus anthracis* proteins in a sample are provided. The anthrax peptides described above are useful for detecting anti-anthrax antibodies in a biological sample from a patient. In addition, the anthrax peptides are useful for the production of anti-anthrax antibodies for the detection of anthrax toxin in a biological sample.

As mentioned above, anti-anthrax monoclonal and polyclonal antibodies having sensitivity for PA, EF and LF toxins are produced by immunizing an animal with one or more of the anthrax peptides described herein, isolating antibodies that react with the epitopes, and collecting and purifying the antibodies from a biological fluid such as blood in accordance with methods well known to those skilled in the art.

Immunoassay methods containing the antibodies immunoreactive with the anthrax toxins are useful for the detection of anthrax in a sample such as an animal sample. Immunoassays employing such antibodies are capable of detecting low concentrations of protein in the sample. The antibodies are immunoreactive with one or more epitopes on the PA, EF and LF proteins and react minimally with other proteins that may be present in the sample, thus providing for an accurate determination of the presence of anthrax in a sample, such as a human possibly exposed to anthrax. The preferred antibodies are monoclonal antibodies, produced by hybridomas, due to their high specificity.

The antibodies are collectively assembled in a kit with conventional immunoassay reagents for detection of anthrax protein. The kit may optionally contain both monoclonal and polyclonal antibodies and a standard for the determination of the presence of anthrax protein in a sample. The kit containing these reagents provides for simple, rapid, on site detection of anthrax protein.

Immunoassays

A sensitive immunoassay employing antibodies as reagents, prepared using the anthrax peptides described above, is provided. The immunoassay is useful for detecting the presence or amount of anthrax toxin in a variety of samples, particularly human samples. The sample may be obtained from any source in which the anthrax proteins are accessible to the antibody. For example, the sample may be a biological fluid of an animal suspected of being infected with anthrax, such as a blood or serum sample. The immunoassay is therefore useful for diagnosis or prognosis of an anthrax infection.

An immunoassay employing the anthrax peptides described herein as reagents is also provided. The peptides are used as reagents to test for specific protective immunity to anthrax in biological samples taken from anthrax vaccinated individuals. The peptides bind to the antibodies in the biological sample. Results from this type of immunoassay provide information on the immune responsiveness of the vaccinated individual that can be used to decrease the number of boosters needed by that individual or can be used to identify individuals who require alternative protective procedures.

The reagents may be employed in any heterogeneous or homogeneous sandwich or competitive immunoassay for the detection of anthrax protein. Either the reagent is labeled with a detectable label or is coupled to a solid phase. Methods for coupling reagents to solid phases are well known to those skilled in the art. In accordance with the immunoassay method, the sample containing the analyte is reacted with the reagent for a sufficient amount of time under conditions that promote the binding of antibody to peptide. It will be understood by those skilled in the art that the immunoassay reagents and sample may be reacted in different combinations and orders. A physical means is employed to separate reagents bound to the solid phase from unbound reagents such as filtration of particles, decantation of reaction solutions from coated tubes or wells, magnetic separation, capillary action, and other means known to those skilled in the art. It will also be understood that a separate washing of the solid phase may be included in the method.

The concentration of anthrax protein, or anti-anthrax antibody, in the sample is determined either by comparing the intensity of the color produced by the sample to a color card or by using a reflectometer.

The resulting reaction mixture, or combination of reagent and sample, is prepared in a solution that optimizes antibody-analyte binding kinetics. An appropriate solution is an aqueous solution or buffer. The solution is preferably provided under conditions that will promote specific binding, minimize nonspecific binding, solubilize analyte, stabilize and preserve reagent reactivity, and may contain buffers, detergents, solvents, salts, chelators, proteins, polymers, carbohydrates, sugars, and other substances known to those skilled in the art.

The reaction mixture solution is reacted for a sufficient amount of time to allow the antibody to react and bind to the peptide to form an antibody-analyte complex. The shortest amount of reaction time that results in binding is desired to minimize the time required to complete the assay. An appropriate reaction time period for an immunochromatographic strip test is less than or equal to 20 minutes or between approximately one minute and 20 minutes. A reaction time of less than five minutes is preferred. Most preferably, the reaction time is less than three minutes. By optimizing the reagents, binding may be substantially completed as the reagents are combined.

The reaction is performed at any temperature at which the reagents do not degrade or become inactivated. A temperature between approximately 4° C. and 37° C. is preferred. The most preferred reaction temperature is ambient or room temperature (approximately 25° C.).

Immunoassay Kit

An immunoassay kit for the detection of anthrax protein in a sample contains one or more antibodies prepared using the epitopes described above.

The kit may additionally contain equipment for obtaining the sample, a vessel for containing the reagents, a timing means, a buffer for diluting the sample, and a colorimeter, reflectometer, or standard against which a color change may be measured.

In a preferred embodiment, the reagents, including the antibody are dry. Addition of aqueous sample to the strip results in solubilization of the dry reagent, causing it to react.

An alternative immunoassay kit would be useful for the detection of specific, protective anthrax epitope reactivity. After vaccination, individuals often need to be assessed to determine if protective immunity has been generated (or continues to be generated). This kit contains one or a mixture of the immunogenic peptides described herein coupled to a solid phase system. Dilutions of sera are incubated with these peptides and detection systems used to measure the presence and concentration of protective antibodies.

The compositions and methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Generation of Mouse Anti-Sera Containing Protective Antibodies to Anthrax Lethal Toxin and Protective Antigen FIG. 2 shows the study design used to immunize groups of A/J mice with recombinant PA, recombinant LF or with adjuvant alone. The initial immunization was conducted in the presence of Complete Freund's Adjuvant (CFA) on day 0 and boosters were given on days 10, 24 and 38.

Blood samples for antibody testing and epitope mapping were collected from individual mice four days after each boost and again before toxin challenge, which was conducted 70-80 days after the final boost.

Figure 3:
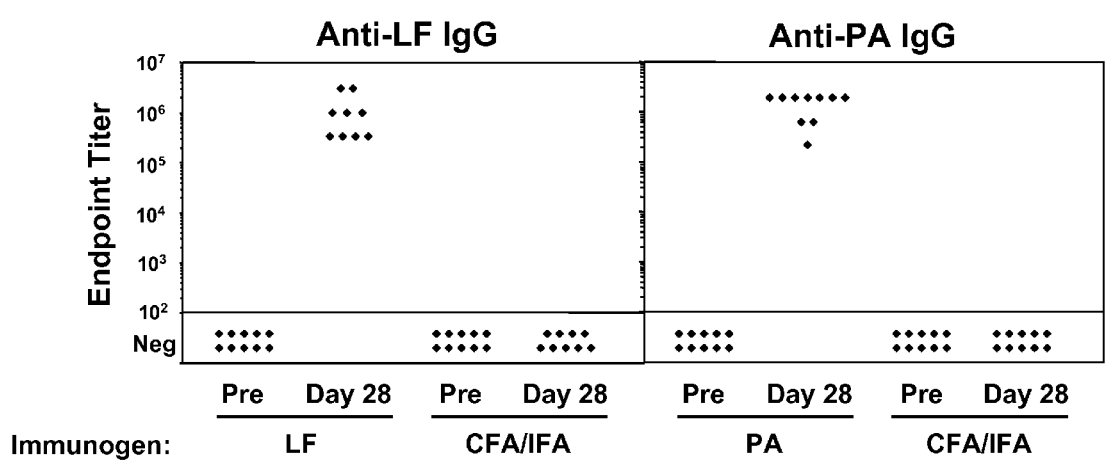
FIG. 3 is a graph of endpoint titer, providing results of anti-LF and anti-PA IgG antibody titers in immunized A/J mice.

FIG. 3 demonstrates verification that the immunized mice were producing robust antibody responses to the recombinant LF and PA immunogens. FIG. 3 shows IgG antibody titers to LF and PA as determined by ELISA using commercially available LF and PA preparations.

LF-immunized mice produced high titers of anti-LF antibodies at day 28, and PA-immunized mice similarly produced high titers of anti-PA antibodies at day 28, while mice immunized with adjuvant alone did not. Samples collected prior to immunization were also negative for these antibodies. The average ODs of 1/100 serum dilutions of each group of sera, also confirm this pattern.

Example 2

Lethal Toxin Challenge

Before conducting epitope mapping, the mice of Example 1 were studied to determine whether they had produced lethal toxin-neutralizing antibodies. To check this, the mice were challenged with a lethal dose of the anthrax lethal toxin, which is co-injected PA plus LF. The dose used was three times the LD50 dose as determined in 6 week old A/J mice (See FIG. 4).

Only one of seven mice in the control group survived the challenge.

In contrast nine of ten PA-immunized mice survived the challenged (p=0.009), and seven of eight LF-immunized mice (p=0.007) survived the challenge. These data suggested that the mice had produced toxin-neutralizing antibodies.

Example 3

Epitope Mapping

Figure 5:
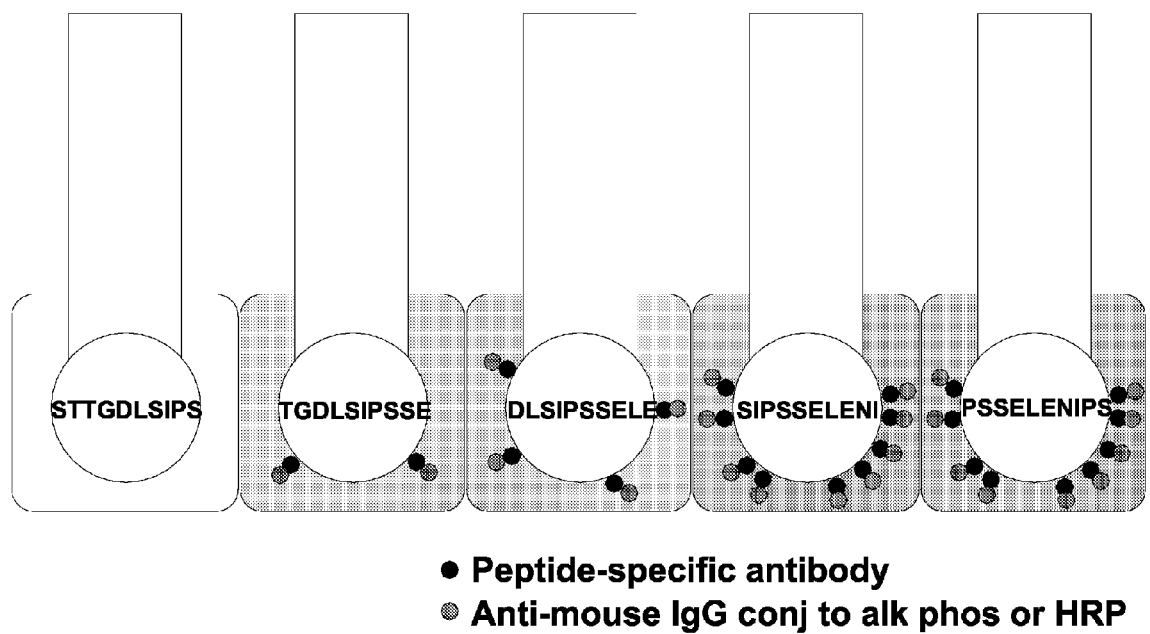
FIG. 5 provides a schematic representation of a solid phase ELISA technique for detection of antibodies specific for sequential overlapping peptide sequences.

To map anti-LF, anti-EF and anti-PA antibodies produced in immunized mice, sera was screened against a series of solid phase bound 10 mer peptides that overlap by eight amino acids (See FIG. 5). The overlapping decapeptides span the entire length of protective antigen (379 peptides), edema factor (396 peptides) and lethal factor (401 peptides).

The decapeptides were conveniently synthesized onto polyethylene rods in a 96-well format. In a modified ELISA technique, the pins were lowered into 96-well plates for various incubations and washed in between.

Each individual decapeptide for each *Bacillus anthracis* toxin component was tested for immunogenic activity. FIGS. 6 A and B demonstrates results obtained in mice for B cell epitopes of lethal factor.

Example 4

Epitope Mapping of Lethal Factor

Figure 6A:
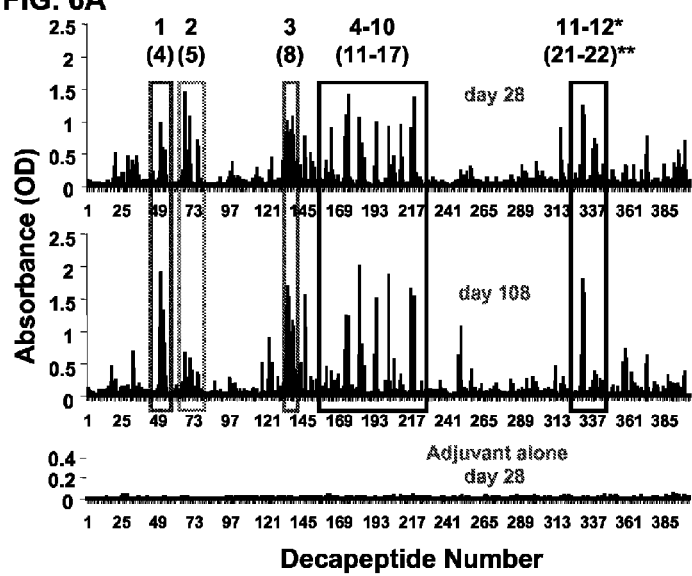
FIGS. 6A and B provide data of sequential mouse B cell epitopes of lethal factor.

FIGS. 6A and B demonstrate the mapping results of LF-immunized A/J mice from day 28 bleed to day 108 bleed. It was found that multiple epitopes exist throughout the molecule. Although some epitopes decreased in reactivity by day 108, certain regions of the lethal factor toxin remained elevated or changed in intensity by day 108. Mice immunized with adjuvant alone failed to significantly bind any of the decapeptides. Regions that spanned at least one decapeptide with an O.D. of 1.0 or above were considered epitopes. Subsets of these epitopes are highlighted in FIGS. 6A and B as examples.

Individual decapeptides observed to be immunogenic above a scale of 0.2 (O.D) were identified as immunogenic peptides. Each extended epitope (denoted as composite sequence) was required to contain at least one decapeptide demonstrating an O.D. of greater than or equal to 0.4.

Figure 6B:
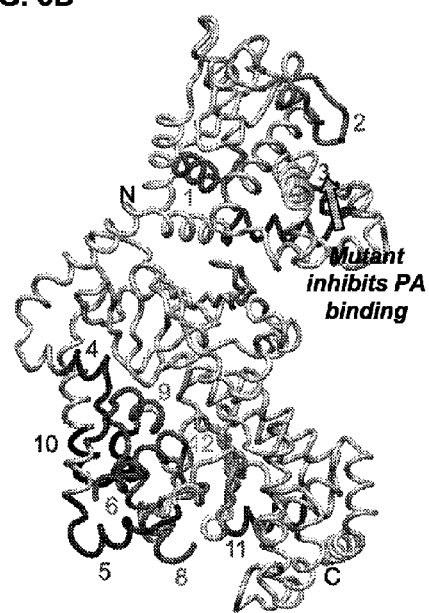

A subset of the epitopes highlighted as examples were superimposed onto the crystal structure of lethal factor in FIG. 6B.

The epitopes as superimposed onto the crystal structure of FIG. 6B and also identified in Table 1 correspond to the following amino acid locations of wild-type lethal factor (See SEQ ID NO:2).

1: EKVPSDVLEMYKAIGGKI (SEQ ID NO:95): corresponds to amino acids 94-114 of wild type lethal factor.

2: SEDKKKIKDIYGKDALLHEH (SEQ ID NO:96): corresponds to amino acids 131-150 of wild type lethal factor.

3:QHRDVLQLYAPEAFNYMDKFNEGEINLSLEELKD (SEQ ID NO:258): corresponds to amino acids 261-294 of wild type lethal factor.

4: LLKKLQIPIE (SEQ ID NO:47): corresponds to amino acids 325-334 of wild type lethal factor.

5: SLSQEEKELLKRIQ (SEQ ID NO:102): corresponds to amino acids 343-356 of wild type lethal factor.

6: DFLSTEEKEFLKKLQIDIRD (SEQ ID NO: 259): corresponds to amino acids 361-378 of wild type lethal factor.

7: SLSEEEKELLNRIQ (SEQ ID NO:104): corresponds to amino acids 381-394 of wild type lethal factor.

8: LSEKEKEFLKKLKLDI (SEQ ID NO:105): corresponds to amino acids 401-416 of wild type lethal factor.

9: GPYDINGRLQDT (SEQ ID NO: 260): corresponds to amino acids 417-428 of wild type lethal factor.

10: LIDSPSINLDVRKQ (SEQ ID NO:107): corresponds to amino acids 431-444 of wild type lethal factor.

11: LVDGNGRFVFTDITLP (SEQ ID NO:110): corresponds to amino acids 655-670 of wild type lethal factor.

12: GYTHQDEIYEGV (SEQ ID NO: 261): corresponds to amino acids 675-686 of wild type lethal factor.

Interestingly, the lethal factor epitopes tended to cluster in domain I, the PA binding domain and domain III, which has some residues that contact the MAP-kinase substrate. Two epitopes were also observed in domain IV of lethal factor, the catalytic domain.

Example 5

Epitope Mapping of Protective Antigen

Figure 7A:
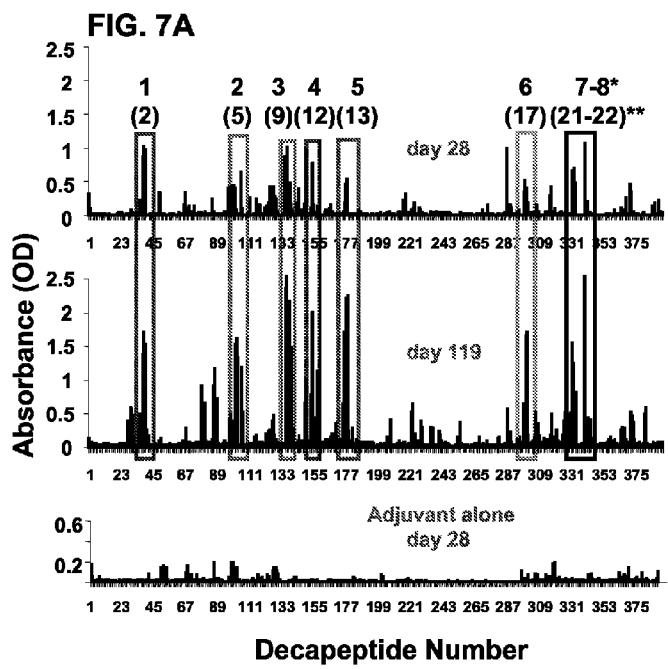
FIGS. 7A and B provide data of sequential mouse B cell epitopes of protective antigen.

FIGS. 7A and B demonstrate the mapping results of PA-immunized A/J mice from day 28 bleed to day 108 bleed. Again it was found that multiple epitopes exist throughout the molecule. PA harbored fewer epitopes than observed for LF, despite high antibody titers.

Regions that spanned at least one decapeptide with reactivity of 0.4 (O.D) or greater were considered epitopes. Eight prominent epitopes, a subset of the total identified epitopes, were overlaid onto the PA crystal structure as examples (See FIG. 7B). Interestingly one of the epitopes spans the furin cleavage site; whereas two of the epitopes occur in regions of PA that have been implicated in influencing binding to LF and EF.

Epitope 5 is not resolved in the crystal structure.

Also shown in FIG. 7A are several unmarked epitopes. In this example, individual decapeptides observed to be immunogenic above a scale of 0.2 and containing at least one decapeptide with reactivity of 0.4 or greater define immunogenic peptides.

Figure 7B:
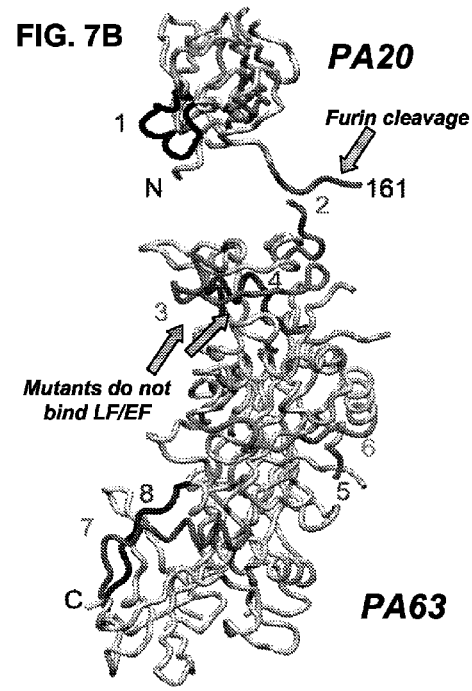

The epitopes as superimposed onto the crystal structure of FIG. 7B and also identified in Table 4 (No. on structure) correspond to the following amino acid locations of wild-type protective antigen (See SEQ ID NO:1).

1: STTGDLSIPSSELENIDSEN (SEQ ID NO: 262): corresponds to amino acids 67-86 of wild-type protective antigen.

2: LKQKSSNSRKKRSTSAGPTVPD (SEQ ID NO:156): corresponds to amino acids 185-206 of wild-type protective antigen.

3: TASDPYSDFEKVTGRIDKNVSP (SEQ ID NO: 160): corresponds to amino acids 257-278 of wild-type protective antigen.

4: VDMENIILSKNEDQSTQN (SEQ ID NO: 163): corresponds to amino acids 293-310 of wild-type protective antigen.

5: NAEVHASFEDIGGSVSAG (SEQ ID NO: 263): corresponds to amino acids 335-352 of wild-type protective antigen.

6: GKDITEFDFNFDQQTS (SEQ ID NO: 168): corresponds to amino acids 573-588 of wild-type protective antigen.

7: AVGADESVVKEAHREVINSSTE (SEQ ID NO: 172): corresponds to amino acids 633-654 of wild-type protective antigen.

8: TEGLLLNIDK (SEQ ID NO: 173): corresponds to amino acids 653-662 of wild-type protective antigen.

Example 6

Strain Background Versus MHC

Figure 8:
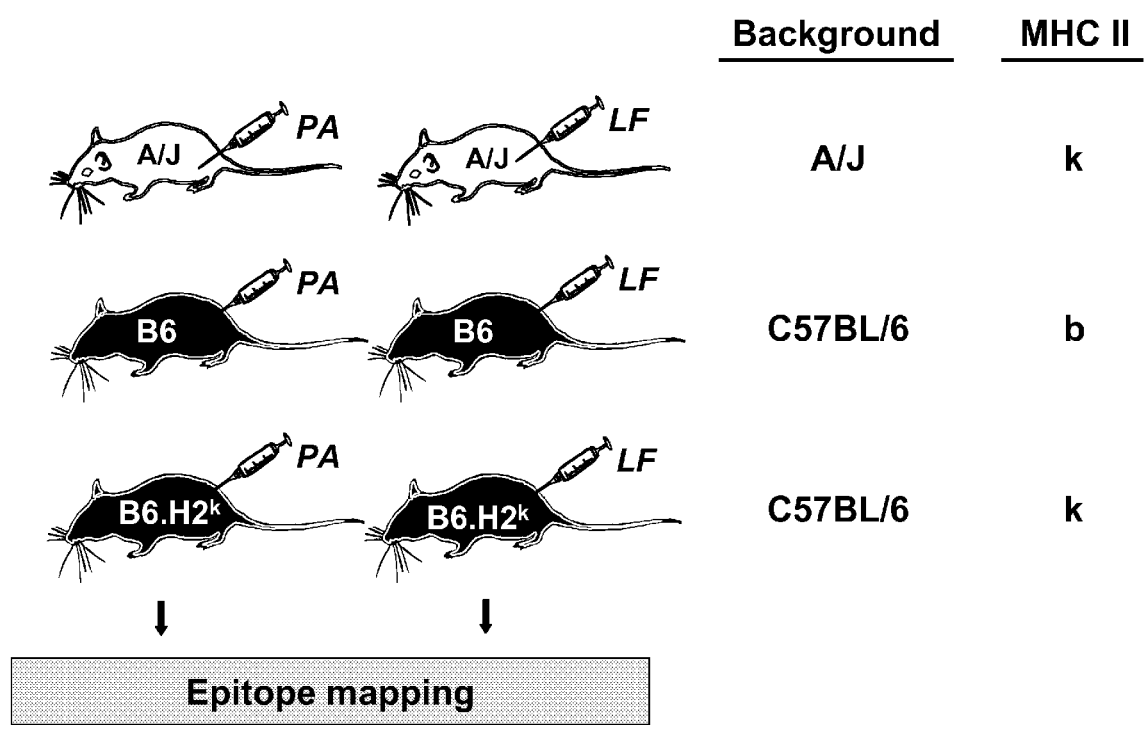
FIG. 8 provides a design study of strain background versus MHC in B cell epitope selection.

In order to broaden the number of identifiable B cell epitopes of PA and LF, epitopes were also mapped in immunized C57BL/6 mice (See FIG. 8).

In order to assess the relative importance of MHC class II haplotype versus genetic background in epitope selection, responses in C57BL/6 mice congenic for the MHC class II haplotype of A/J mice were also assessed (See FIG. 8).

FIGS. 9A-C show the mapping results after LF immunization in Day 28 bleeds.

Some epitopes were identified as common among the strains, denoted by the "C", while other epitopes depended upon the genetic background, denoted by the "B". In this case, the A/J background was important.

Interestingly, other epitopes were strongly influenced by MHC class II, and these epitopes are denoted by "M". In those instances, the "k" haplotype was required for this epitope.

In total, most epitopes were determined by non-MHC background genes, while several epitopes were common between the two strains.

MHC class II haplotype was found not to be an important determinant of B cell epitope selection.

FIGS. 10A-C show the mapping results after PA immunization in Day 28 bleeds.

Example 7

Evaluation of Antibodies to Protective Antigen in Vaccinated Humans

To begin examining the humoral immune response following anthrax vaccination, individuals who had received three or more doses of the anthrax vaccine absorbed (AVA) were recruited and peripheral blood was collected. A cohort of 114 vaccinated individuals as well as 26 unvaccinated controls were recruited into the study. The majority of the individuals, 61.4%, were Caucasian with 23.68% African American, 5.26% Asian, and 9.64% of other nationalities. The average age was 33.83 (±8.6), the average number of vaccinations was 5.12 (±1.47), and the average time since the last vaccination was 2.45 (±1.39) years.

Figures 11A, 11B, 11C, 11D:
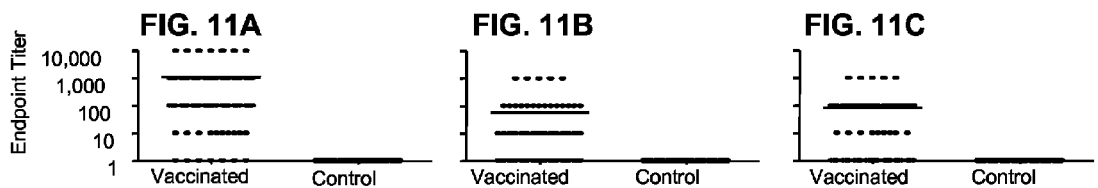
FIGS. 11A-D provide data on anti-Bacillus anthracis antibodies following AVA vaccination.

The sera from these individuals was used in a standard ELISA to detect the level of antibodies against protective antigen, lethal factor, and edema factor. An optical density greater than the average plus twice the standard deviation of the controls was considered positive. The vaccinated individuals had detectable anti-protective antigen antibodies (FIGS. 11A-D), while only a subset had detectable anti-lethal factor or anti-edema factor antibodies. Individuals with anti-protective antigen antibodies could be divided into four groups based upon antibody titer (1:10, 1:100, 1:1,000, and 1:10,000). Surprisingly, the level of antigen-specific antibodies did not correlate with age of the vaccinee nor the number of vaccinations (FIG. 11D). Additionally, the presence or absence of anti-lethal or edema factor antibodies did not correlate with the level of anti-protective antigen antibodies. However, a significant (p=0.0008) inverse correlation between the years post vaccination and the anti-PA titer was found. Thus, those individuals with the highest titer of anti-protective antigen antibodies were most recently vaccinated (1.0±0.4 years post vaccination, FIG. 11D).

Example 8

Evaluation of AVA Vaccinated Individual Sera for In Vitro Inhibition of Toxin Macrophage Kills Because antibodies that are potentially neutralizing are most interesting, this example focused on the epitopes identified in those individuals who were high responders (FIGS. 23A-D and Table 7) and antibodies in regions with high potential for toxin neutralization. The most prominent epitope identified in the high responders was an epitope, QLPELKQKSSNSRKKRSTSA (SEQ ID NO: 199), which was identified as the region containing the furin cleavage site. In fact, five out of six (or 83%) of the high responders had antibodies directed against this antigenic region based upon the solid phase peptide assay. In addition to this epitope within the furin cleavage site, the ability of two other epitopes to mediate protection was analyzed. The first of these was an epitope within the ligand binding region (PYSDFEKVT-GRIDKNV, SEQ ID NO: 201). The final epitope was identified using solid phase peptide assays on sera from mice immunized with protective antigen (described below) and is within the receptor binding domain of the protective antigen.

Figure 22A:
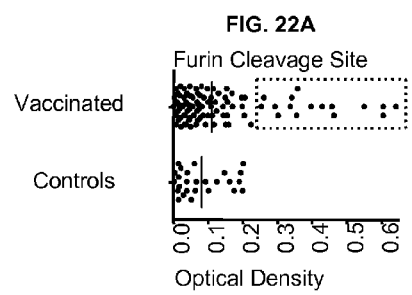
FIGS. 22A-G are graphs of data showing confirmation of peptide epitopes.
Figure 22B:
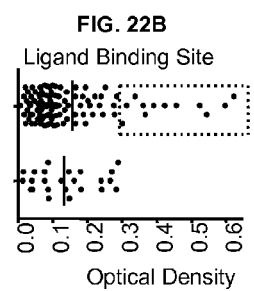
Figure 22C:
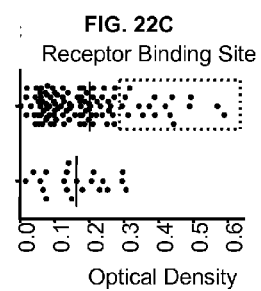
Figure 22D:
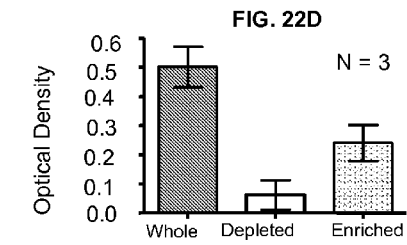
Figure 22E:
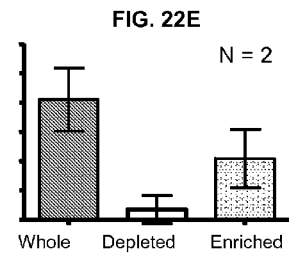
Figure 22F:
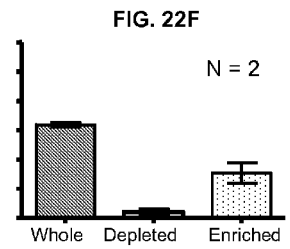
Figure 22G:
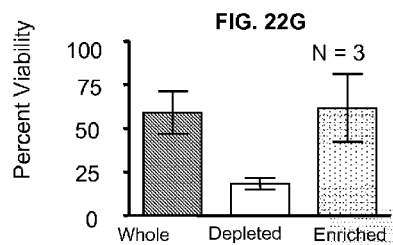

To test for antibodies directed at these three epitopes of interest, peptides covering these regions were synthesized and used in a peptide-specific ELISA. As shown in FIGS. 22 A-C, 16 individuals were identified with antibodies directed at the furin cleavage site epitope, 12 individuals with antibodies directed at the ligand binding site epitope, and 18 individuals with antibodies directed at the receptor binding site. Once these unique antigen regions had been identified and confirmed, the ability of antibodies to these epitopes to mediate protection was tested. Thus, peptide-specific antibodies were enriched using column absorption followed by peptide-specific ELISAs and toxin neutralization. As shown in FIGS. 22 D-F, in all cases it was possible to significantly enrich and deplete for antibodies specific for the corresponding peptide. These enriched and depleted samples were then used in a standard toxin neutralization assay to test the ability of these peptide-specific antibodies to mediate protection. As shown in FIG. 22G, antibodies directed against the epitope within the furin cleavage site were able to block toxin activity while antibodies directed at the other two epitopes were less capable. Thus, the furin peptide-specific antibodies generated following AVA vaccination are capable of neutralizing toxin activity.

Example 9

Specificity of Protective Antigen Antibodies

The fine specificity of the protective antigen antibody response was evaluated utilizing overlapping decapeptides synthesized on a solid phase support, as described above for Example 3. Briefly, sera from a vaccinated individual was incubated with overlapping decapeptides of PA, followed by incubation with a human IgG conjugate linked to HRP, and absorbance at 450 nm determined. As shown in FIG. 12, the fine specificity of the protective antigen antibody response following vaccination can be clearly observed. FIGS. 12A-C also present the most reactive epitopes (epitopes # 1-9) superimposed onto the crystal structure of PA (See FIG. 12C). The observation of regions associated with immunogenicity allows for the detection of epitopes and individual decapeptides that are immunogenic peptide fragments.

FIGS. 23A-D present the fine specificity of the response stratified by ability of the vaccinated individual sera to inhibit macrophase killing (surrogate in vitro model of neutralization). Additional and unique areas of humoral epitope specificity were determined by this method.

Example 10

Evaluation of Antibodies to Lethal Factor in Vaccinated Humans

As discussed above, for examination of humoral and cellular immunity following anthrax vaccination, sera from individuals who had received three or more doses of the anthrax vaccine absorbed (AVA), as well as unvaccinated controls matched by age, sex, and race, were analyzed. As seen in FIG. 11D, the majority of individuals tested had received the recommended six vaccinations, and the average time since the last vaccination was 2.33 (±1.9) years. The sera were tested by ELISA to detect the level of antibodies against lethal factor. An optical density greater than the average plus twice the standard deviation of the controls was considered positive.

All of the vaccinated individuals (n=29) had detectable anti-protective antigen antibodies (FIGS. 11A-C). However, only a subset of these vaccinated individuals had detectable antibodies to lethal factor (n=9) or edema factor (n=10).

The fine specificity of the lethal factor antibody response was evaluated utilizing overlapping decapeptides synthesized on a solid phase support, as described above for Example 3. Briefly, sera from a vaccinated individual was incubated with overlapping decapeptides of LF, followed by incubation with a human IgG conjugate linked to HRP, and absorbance at 450 nm determined. As shown in FIG. 14A, the fine specificity of the lethal factor antibody response following vaccination can be clearly observed. FIG. 14C also presents the most reactive epitopes (epitopes # 1-10) superimposed onto the crystal structure of LF. The observation of regions associated with immunogenicity allows for the detection of epitopes and individual decapeptides that are immunogenic peptide fragments.

Example 11

Figure 16:
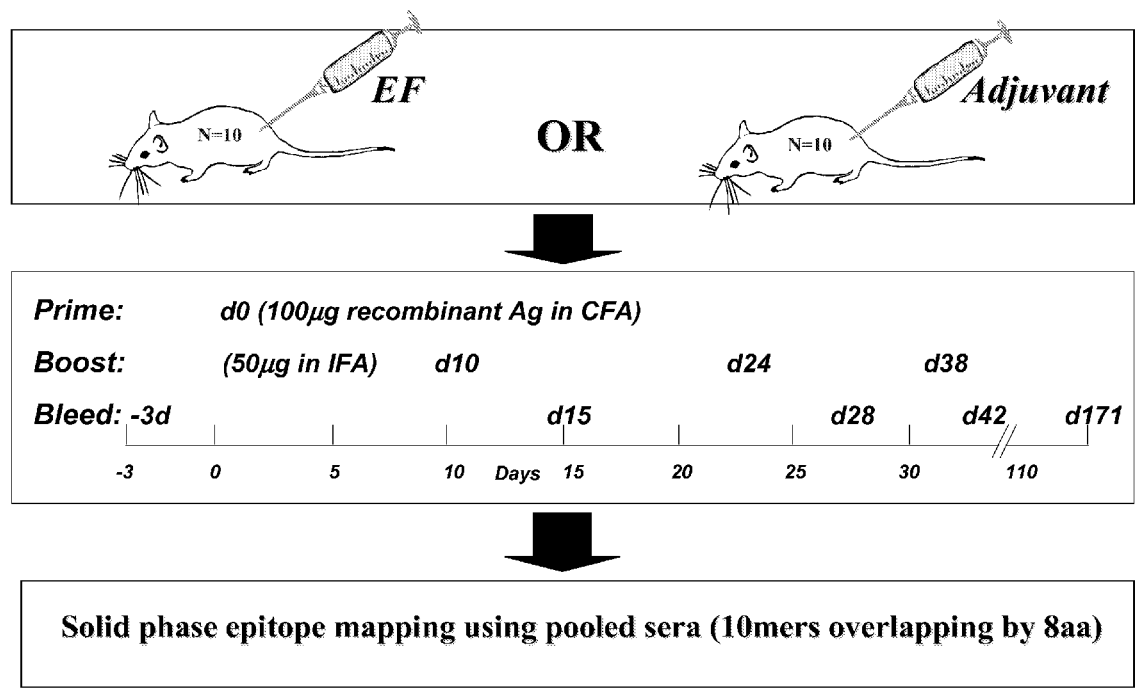
FIG. 16 a flow chart providing study details for generation of anti-Edema Factor (EF) antisera containing neutralizing antibodies in mice.

Generation of Anti-Sera Containing Protective Antibodies to Anthrax Edema Factor FIG. 16 shows the study design used to immunize groups of A/J mice with recombinant EF or with adjuvant alone. The initial immunization was conducted in the presence of CFA on day 0 and boosters were given on days 10, 24 and 38.

Blood samples for antibody testing and epitope mapping were collected from individual mice 4-5 days after each boost and again prior to edema toxin challenge, which was 129 days after the final boost.

FIGS. 17A and B demonstrate verification that the immunized mice were producing robust antibody responses to the recombinant EF. FIG. 17A shows IgG antibody titers to EF as determined by ELISA using a commercially available EF preparation.

All EF-immunized mice produced high titers of anti-EF antibodies at days 28, 42 and 171.

Example 12

Edema Toxin Challenge

The mice of Example 11 were studied to determine whether they had produced edema toxin-neutralizing antibodies. To check this, the LD50 of edema toxin was first determined in unimmunized six week old A/J mice (see FIG. 18A). The mice of Example 11 were then challenged with a lethal dose of the anthrax edema toxin, which is co-injected PA plus EF. The dose used was four times the LD50 dose determined in A/J mice.

Fifty percent of the EF-immunized mice survived the lethal edema toxin challenge, while 0% of the control mice that had been immunized with adjuvant alone survived the challenge (see FIG. 18B). These data suggested that the EF-immunized mice of Example 11 had produced edema toxin-neutralizing antibodies.

Example 13

Epitope Mapping of Edema Factor

FIGS. 19A and B demonstrate the mapping results of EF-immunized A/J mice from day 15 and day 28 bleeds. It was found that the response initiated with a single epitope on day 15 then expanded to include multiple epitopes by day 28. Mice immunized with adjuvant alone failed to significantly bind any of the decapeptides. Regions that spanned at least one decapeptide with an O.D. of 0.3 and above were considered epitopes. These epitopes are highlighted in FIG. 19B and superimposed onto the known EF crystal structure as examples from this particular mouse strain.

The epitopes, as superimposed onto the crystal structure of FIG. 19B, and also identified in Table 9, correspond to the following amino acid locations of wild-type edema factor (See SEQ ID NO:3).

1: KNSMNSRGEKVPFASRFV (SEQ ID NO: 249): corresponds to amino acids 125-142 of wild type edema factor.

2: YAINSEQSKEVY (SEQ ID NO: 250): corresponds to amino acids 159-170 of wild type edema factor.

3: SSDLLFSQKFKE (SEQ ID NO: 251): corresponds to amino acids 205-216 of wild type edema factor.

4. LELYAPDMFEYM (SEQ ID NO: 252): corresponds to amino acids 257-268 of wild type edema factor.

5. EGEIGKIPLKLD (SEQ ID NO: 253): corresponds to amino acids 395-406 of wild type edema factor.

6. DYDLFALAPSLT (SEQ ID NO: 254): corresponds to amino acids 491-502 of wild type edema factor.

7. NWQKQMLDRLNEAV (SEQ ID NO: 255): corresponds to amino acids 551-564 of wild type edema factor.

8. NEAVKYTGYTGG (SEQ ID NO: 256): corresponds to amino acids 561-572 of wild type edema factor.

9. QDNEEFPEKDNEIF (SEQ ID NO: 257): corresponds to amino acids 581-594 of wild type edema factor.

Example 14

Identification of Neutralizing Peptide Epitopes of PA and LF Using Murine Immune Serum Immune sera from LF- and PA-immunized A/J mice were subjected to affinity chromatography using multiple antigenic peptide columns constructed from the following epitopes which are also disclosed in FIGS. 6A and B and 7A and B, respectively, and Tables 1-4: PA 164-177, RKKRST-SAGPTVPD (SEQ ID NO: 264); PA 230-243, SDPYSD-FEKVTGRIDK (SEQ ID NO: 265); and LF 232-247, VLQ-LYAPEAFNYMDKF (SEQ ID NO: 266). The numbers here refer to amino acids in SEQ ID NO:1 for PA and SEQ ID NO:2 for LF. Individual column fractions were concentrated to the original serum volume and titrated into a standard Lethal Toxin-mediated macrophage cell death assay. As shown in FIGS. 20A-C, all three preparations of the thus-purified antibodies demonstrated a capacity for neutralizing the ability of Lethal Toxin to kill a mouse macrophage cell line, as indicated by increased % cell viability. The concentration of total IgG in each retained (i.e. peptide-binding) fraction was quantitated and is indicated in FIGS. 20A-C.

All scientific articles, publications, abstracts, patents and patent applications mentioned above are hereby incorporated by reference in their entirety.

While this invention has been described in specific detail with reference to the disclosed embodiments, it will be understood that many variations and modifications may be effected within the spirit and scope of the invention.

We claim:

1. A composition comprising an isolated immunogenic peptide consisting of 40 or less amino acids and comprising SEQ ID NO: 170.

2. The composition of claim 1, wherein the peptide is coupled to a carrier.

3. The composition of claim 2, wherein the carrier is a protective antigen protein.

4. The composition of claim 1, further comprising a second immunogenic peptide derived from *Bacillus anthracis*.

5. A composition comprising an immunogenic fusion protein of two or more immunogenic peptides, wherein at least one peptide of the two or more immunogenic peptides consists of 40 or less amino acids and comprises SEQ ID NO: 170.

6. The composition of claim 1, wherein the peptide consists of 20 amino acids or less.

7. A method of inducing an immune response comprising administering to an animal or a human an effective amount of the composition of claim 1.

8. A method of producing an antibody comprising administering to an animal or a human an effective amount of the composition of claim 1.

9. The method of claim 8, wherein the antibody is a monoclonal or polyclonal antibody.

10. A method of producing an antibody comprising administering to an animal or a human an effective amount of the composition of claim 5.

11. A method for detecting an antibody infection in an animal or a human comprising
  combining a sample from the animal or the human with an immunoreactive peptide, wherein the peptide consists of SEQ ID NO:170, and
  detecting a complex formed between the antibody in the sample and the immunoreactive peptide,
  wherein detection of a complex indicates anthrax infection in the animal.

12. A method for detecting specific protective immunity to anthrax infection in an animal or a human comprising
  combining a sample from the animal with an immunoreactive peptide, wherein the peptide has 40 or less amino acids and comprises SEQ ID NO:170 has, and
  detecting a complex formed between an antibody in the sample and the immunoreactive peptide,
  wherein detection of a predetermined amount of complex indicates specific protective immunity to anthrax infection in the animal.

13. The composition of claim 5, wherein the at least one peptide consists of 20 amino acids or less.

14. The composition of claim 1, wherein the peptide consists of between 12 and 18 amino acids.

15. The composition of claim 5, wherein the at least one peptide consists of between 12 and 18 amino acids.

* * * * *

```
                           SEQUENCE LISTING

<160> NUMBER OF SEQ ID NOS: 267

<210> SEQ ID NO 1
<211> LENGTH: 764
<212> TYPE: PRT
<213> ORGANISM: Bacillus anthracis

<400> SEQUENCE: 1

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Glu Thr Arg Thr Ile Ser Lys
305                 310                 315                 320
```

-continued

```
Asn Thr Ser Thr Ser Arg Thr His Thr Ser Glu Val His Gly Asn Ala
            325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
            355                 360                 365

Leu Ala Gly Glu Arg Thr Trp Ala Glu Thr Met Gly Leu Asn Thr Ala
            370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
            405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
            485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
            530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
            565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
            595                 600                 605

Lys Ile Lys Leu Asn Ala Lys Met Asn Ile Leu Ile Arg Asp Lys Arg
            610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
            645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
            675                 680                 685

Tyr Asp Met Leu Asn Ile Ser Ser Leu Arg Gln Asp Gly Lys Thr Phe
            690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
            725                 730                 735

Ile Asn Pro Ser Glu Asn Gly Asp Thr Ser Thr Asn Gly Ile Lys Lys
```

```
                    740                 745                 750
Ile Leu Ile Phe Ser Lys Lys Gly Tyr Glu Ile Gly
            755                 760

<210> SEQ ID NO 2
<211> LENGTH: 809
<212> TYPE: PRT
<213> ORGANISM: Bacillus anthracis

<400> SEQUENCE: 2

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Arg Asn Lys Thr
    50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ala Arg Tyr Glu Lys Trp
    290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Glu Lys Glu Leu Leu
            340                 345                 350
```

-continued

```
Lys Arg Ile Gln Ile Asp Ser Ser Asp Phe Leu Ser Thr Glu Glu Lys
            355                 360                 365
Glu Phe Leu Lys Lys Leu Gln Ile Asp Ile Arg Asp Ser Leu Ser Glu
    370                 375                 380
Glu Glu Lys Glu Leu Leu Asn Arg Ile Gln Val Asp Ser Ser Asn Pro
385                 390                 395                 400
Leu Ser Glu Lys Glu Lys Glu Phe Leu Lys Lys Leu Lys Leu Asp Ile
                405                 410                 415
Gln Pro Tyr Asp Ile Asn Gln Arg Leu Gln Asp Thr Gly Gly Leu Ile
            420                 425                 430
Asp Ser Pro Ser Ile Asn Leu Asp Val Arg Lys Gln Tyr Lys Arg Asp
            435                 440                 445
Ile Gln Asn Ile Asp Ala Leu Leu His Gln Ser Ile Gly Ser Thr Leu
        450                 455                 460
Tyr Asn Lys Ile Tyr Leu Tyr Glu Asn Met Asn Ile Asn Asn Leu Thr
465                 470                 475                 480
Ala Thr Leu Gly Ala Asp Leu Val Asp Ser Thr Asp Asn Thr Lys Ile
                485                 490                 495
Asn Arg Gly Ile Phe Asn Glu Phe Lys Lys Asn Phe Lys Tyr Ser Ile
            500                 505                 510
Ser Ser Asn Tyr Met Ile Val Asp Ile Asn Glu Arg Pro Ala Leu Asp
        515                 520                 525
Asn Glu Arg Leu Lys Trp Arg Ile Gln Leu Ser Pro Asp Thr Arg Ala
        530                 535                 540
Gly Tyr Leu Glu Asn Gly Lys Leu Ile Leu Gln Arg Asn Ile Gly Leu
545                 550                 555                 560
Glu Ile Lys Asp Val Gln Ile Ile Lys Gln Ser Glu Lys Glu Tyr Ile
                565                 570                 575
Arg Ile Asp Ala Lys Val Val Pro Lys Ser Lys Ile Asp Thr Lys Ile
            580                 585                 590
Gln Glu Ala Gln Leu Asn Ile Asn Gln Glu Trp Asn Lys Ala Leu Gly
        595                 600                 605
Leu Pro Lys Tyr Thr Lys Leu Ile Thr Phe Asn Val His Asn Arg Tyr
    610                 615                 620
Ala Ser Asn Ile Val Glu Ser Ala Tyr Leu Ile Leu Asn Glu Trp Lys
625                 630                 635                 640
Asn Asn Ile Gln Ser Asp Leu Ile Lys Lys Val Thr Asn Tyr Leu Val
                645                 650                 655
Asp Gly Asn Gly Arg Phe Val Phe Thr Asp Ile Thr Leu Pro Asn Ile
            660                 665                 670
Ala Glu Gln Tyr Thr His Gln Asp Glu Ile Tyr Glu Gln Val His Ser
        675                 680                 685
Lys Gly Leu Tyr Val Pro Glu Ser Arg Ser Ile Leu Leu His Gly Pro
    690                 695                 700
Ser Lys Gly Val Glu Leu Arg Asn Asp Ser Glu Gly Phe Ile His Glu
705                 710                 715                 720
Phe Gly His Ala Val Asp Asp Tyr Ala Gly Tyr Leu Leu Asp Lys Asn
                725                 730                 735
Gln Ser Asp Leu Val Thr Asn Ser Lys Lys Phe Ile Asp Ile Phe Lys
            740                 745                 750
Glu Glu Gly Ser Asn Leu Thr Ser Tyr Gly Arg Thr Asn Glu Ala Glu
        755                 760                 765
Phe Phe Ala Glu Ala Phe Arg Leu Met His Ser Thr Asp His Ala Glu
```

```
                    770                 775                 780
Arg Leu Lys Val Gln Lys Asn Ala Pro Lys Thr Phe Gln Phe Ile Asn
785                 790                 795                 800

Asp Gln Ile Lys Phe Ile Ile Asn Ser
                805

<210> SEQ ID NO 3
<211> LENGTH: 800
<212> TYPE: PRT
<213> ORGANISM: Bacillus anthracis

<400> SEQUENCE: 3

Met Thr Arg Asn Lys Phe Ile Pro Asn Lys Phe Ser Ile Ile Ser Phe
1               5                   10                  15

Ser Val Leu Leu Phe Ala Ile Ser Ser Ser Gln Ala Ile Glu Val Asn
                20                  25                  30

Ala Met Asn Glu His Tyr Thr Glu Ser Asp Ile Lys Arg Asn His Lys
            35                  40                  45

Thr Glu Lys Asn Lys Thr Glu Lys Glu Lys Phe Lys Asp Ser Ile Asn
50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
            100                 105                 110

Glu His Lys Glu Leu Gln Asp Leu Ser Glu Glu Lys Asn Ser Met
        115                 120                 125

Asn Ser Arg Gly Glu Lys Val Pro Phe Ala Ser Arg Phe Val Phe Glu
130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Ser Asp Ser Ser Asp Leu
        195                 200                 205

Leu Phe Ser Gln Lys Phe Lys Glu Lys Leu Glu Leu Asn Asn Lys Ser
210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
            260                 265                 270

Lys Gly Gly Phe Glu Lys Ile Ser Glu Ser Leu Lys Lys Glu Gly Val
        275                 280                 285

Glu Lys Asp Arg Ile Asp Val Leu Lys Gly Glu Lys Ala Leu Lys Ala
290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335
```

-continued

```
Asn Leu Ile Lys Ser Gly Val Ala Thr Lys Gly Leu Asn Glu His Gly
                340                 345                 350
Lys Ser Ser Asp Trp Gly Pro Val Ala Gly Tyr Ile Pro Phe Asp Gln
            355                 360                 365
Asp Leu Ser Lys Lys His Gly Gln Gln Leu Ala Val Glu Lys Gly Asn
        370                 375                 380
Leu Glu Asn Lys Lys Ser Ile Thr Glu His Glu Gly Glu Ile Gly Lys
385                 390                 395                 400
Ile Pro Leu Lys Leu Asp His Leu Arg Ile Glu Glu Leu Lys Glu Asn
                405                 410                 415
Gly Ile Ile Leu Lys Gly Lys Lys Glu Ile Asp Asn Gly Lys Lys Tyr
            420                 425                 430
Tyr Leu Leu Glu Ser Asn Asn Gln Val Tyr Glu Phe Arg Ile Ser Asp
        435                 440                 445
Glu Asn Asn Glu Val Gln Tyr Lys Thr Lys Glu Gly Lys Ile Thr Val
    450                 455                 460
Leu Gly Glu Lys Phe Asn Trp Arg Asn Ile Glu Val Met Ala Lys Asn
465                 470                 475                 480
Val Glu Gly Val Leu Lys Pro Leu Thr Ala Asp Tyr Asp Leu Phe Ala
                485                 490                 495
Leu Ala Pro Ser Leu Thr Glu Ile Lys Lys Gln Ile Pro Thr Lys Arg
            500                 505                 510
Met Asp Lys Val Val Asn Thr Pro Asn Ser Leu Glu Lys Gln Lys Gly
        515                 520                 525
Val Thr Asn Leu Leu Ile Lys Tyr Gly Ile Glu Arg Lys Pro Asp Ser
    530                 535                 540
Thr Lys Gly Thr Leu Ser Asn Trp Gln Lys Gln Met Leu Asp Arg Leu
545                 550                 555                 560
Asn Glu Ala Val Lys Tyr Thr Gly Tyr Thr Gly Gly Asp Val Val Asn
                565                 570                 575
His Gly Thr Glu Gln Asp Asn Glu Glu Phe Pro Glu Lys Asp Asn Glu
            580                 585                 590
Ile Phe Ile Ile Asn Pro Glu Gly Glu Phe Ile Leu Thr Lys Asn Trp
        595                 600                 605
Glu Met Thr Gly Arg Phe Ile Glu Lys Asn Ile Thr Gly Lys Asp Tyr
    610                 615                 620
Leu Tyr Tyr Phe Asn Arg Ser Tyr Asn Lys Ile Ala Pro Gly Asn Lys
625                 630                 635                 640
Ala Tyr Ile Glu Trp Thr Asp Pro Ile Thr Lys Ala Lys Ile Asn Thr
                645                 650                 655
Ile Pro Thr Ser Ala Glu Phe Ile Lys Asn Leu Ser Ser Ile Arg Arg
            660                 665                 670
Ser Ser Asn Val Gly Val Tyr Lys Asp Ser Gly Asp Lys Asp Glu Phe
        675                 680                 685
Ala Lys Lys Glu Ser Val Lys Lys Ile Ala Gly Tyr Leu Ser Asp Tyr
    690                 695                 700
Tyr Asn Ser Ala Asn His Ile Phe Ser Gln Glu Lys Lys Arg Lys Ile
705                 710                 715                 720
Ser Ile Phe Arg Gly Ile Gln Ala Tyr Asn Glu Ile Glu Asn Val Leu
                725                 730                 735
Lys Ser Lys Gln Ile Ala Pro Glu Tyr Lys Asn Tyr Phe Gln Tyr Leu
            740                 745                 750
Lys Glu Arg Ile Thr Asn Gln Val Gln Leu Leu Leu Thr His Gln Lys
```

```
                    755                 760                 765
Ser Asn Ile Glu Phe Lys Leu Leu Tyr Lys Gln Leu Asn Phe Thr Glu
        770                 775                 780

Asn Glu Thr Asp Asn Phe Glu Val Phe Gln Lys Ile Ile Asp Glu Lys
785                 790                 795                 800
```

<210> SEQ ID NO 4
<211> LENGTH: 10
<212> TYPE: PRT
<213> ORGANISM: Bacillus anthracis

<400> SEQUENCE: 4

```
Gly Ala Gly Gly His Gly Asp Val Gly Met
1               5                   10
```

<210> SEQ ID NO 5
<211> LENGTH: 10
<212> TYPE: PRT
<213> ORGANISM: Bacillus anthracis

<400> SEQUENCE: 5

```
Gly Gly His Gly Asp Val Gly Met His Val
1               5                   10
```

<210> SEQ ID NO 6
<211> LENGTH: 10
<212> TYPE: PRT
<213> ORGANISM: Bacillus anthracis

<400> SEQUENCE: 6

```
His Gly Asp Val Gly Met His Val Lys Glu
1               5                   10
```

<210> SEQ ID NO 7
<211> LENGTH: 10
<212> TYPE: PRT
<213> ORGANISM: Bacillus anthracis

<400> SEQUENCE: 7

```
Asp Val Gly Met His Val Lys Glu Lys Glu
1               5                   10
```

<210> SEQ ID NO 8
<211> LENGTH: 10
<212> TYPE: PRT
<213> ORGANISM: Bacillus anthracis

<400> SEQUENCE: 8

```
Lys Glu Lys Asn Lys Asp Glu Asn Lys Arg
1               5                   10
```

<210> SEQ ID NO 9
<211> LENGTH: 10
<212> TYPE: PRT
<213> ORGANISM: Bacillus anthracis

<400> SEQUENCE: 9

```
Lys Asn Lys Asp Glu Asn Lys Arg Lys Asp
1               5                   10
```

<210> SEQ ID NO 10
<211> LENGTH: 10
<212> TYPE: PRT
<213> ORGANISM: Bacillus anthracis -continued

```
<400> SEQUENCE: 10

Arg Asn Lys Thr Gln Glu Glu His Leu Lys
1               5                   10

<210> SEQ ID NO 11
<211> LENGTH: 10
<212> TYPE: PRT
<213> ORGANISM: Bacillus anthracis

<400> SEQUENCE: 11

Lys Thr Gln Glu Glu His Leu Lys Glu Ile
1               5                   10

<210> SEQ ID NO 12
<211> LENGTH: 10
<212> TYPE: PRT
<213> ORGANISM: Bacillus anthracis

<400> SEQUENCE: 12

Gln Glu Glu His Leu Lys Glu Ile Met Lys
1               5                   10

<210> SEQ ID NO 13
<211> LENGTH: 10
<212> TYPE: PRT
<213> ORGANISM: Bacillus anthracis

<400> SEQUENCE: 13

Glu His Leu Lys Glu Ile Met Lys His Ile
1               5                   10

<210> SEQ ID NO 14
<211> LENGTH: 10
<212> TYPE: PRT
<213> ORGANISM: Bacillus anthracis

<400> SEQUENCE: 14

Glu Lys Val Pro Ser Asp Val Leu Glu Met
1               5                   10

<210> SEQ ID NO 15
<211> LENGTH: 10
<212> TYPE: PRT
<213> ORGANISM: Bacillus anthracis

<400> SEQUENCE: 15

Val Pro Ser Asp Val Leu Glu Met Tyr Lys
1               5                   10

<210> SEQ ID NO 16
<211> LENGTH: 10
<212> TYPE: PRT
<213> ORGANISM: Bacillus anthracis

<400> SEQUENCE: 16

Ser Asp Val Leu Glu Met Tyr Lys Ala Ile
1               5                   10

<210> SEQ ID NO 17
<211> LENGTH: 10
<212> TYPE: PRT
<213> ORGANISM: Bacillus anthracis

<400> SEQUENCE: 17
```

Val Leu Glu Met Tyr Lys Ala Ile Gly Gly
1               5                   10

<210> SEQ ID NO 18
<211> LENGTH: 10
<212> TYPE: PRT
<213> ORGANISM: Bacillus anthracis

<400> SEQUENCE: 18

Glu Met Tyr Lys Ala Ile Gly Gly Lys Ile
1               5                   10

<210> SEQ ID NO 19
<211> LENGTH: 10
<212> TYPE: PRT
<213> ORGANISM: Bacillus anthracis

<400> SEQUENCE: 19

Ser Glu Asp Lys Lys Lys Ile Lys Asp Ile
1               5                   10

<210> SEQ ID NO 20
<211> LENGTH: 10
<212> TYPE: PRT
<213> ORGANISM: Bacillus anthracis

<400> SEQUENCE: 20

Asp Lys Lys Lys Ile Lys Asp Ile Tyr Gly
1               5                   10

<210> SEQ ID NO 21
<211> LENGTH: 10
<212> TYPE: PRT
<213> ORGANISM: Bacillus anthracis

<400> SEQUENCE: 21

Lys Lys Ile Lys Asp Ile Tyr Gly Lys Asp
1               5                   10

<210> SEQ ID NO 22
<211> LENGTH: 10
<212> TYPE: PRT
<213> ORGANISM: Bacillus anthracis

<400> SEQUENCE: 22

Ile Lys Asp Ile Tyr Gly Lys Asp Ala Leu
1               5                   10

<210> SEQ ID NO 23
<211> LENGTH: 10
<212> TYPE: PRT
<213> ORGANISM: Bacillus anthracis

<400> SEQUENCE: 23

Asp Ile Tyr Gly Lys Asp Ala Leu Leu His
1               5                   10

<210> SEQ ID NO 24
<211> LENGTH: 10
<212> TYPE: PRT
<213> ORGANISM: Bacillus anthracis

<400> SEQUENCE: 24

Tyr Gly Lys Asp Ala Leu Leu His Glu His

-continued

<210> SEQ ID NO 25
<211> LENGTH: 10
<212> TYPE: PRT
<213> ORGANISM: Bacillus anthracis

<400> SEQUENCE: 25

Leu His Glu His Tyr Val Tyr Ala Lys Glu
1               5                   10

<210> SEQ ID NO 26
<211> LENGTH: 10
<212> TYPE: PRT
<213> ORGANISM: Bacillus anthracis

<400> SEQUENCE: 26

Glu His Tyr Val Tyr Ala Lys Glu Gly Tyr
1               5                   10

<210> SEQ ID NO 27
<211> LENGTH: 10
<212> TYPE: PRT
<213> ORGANISM: Bacillus anthracis

<400> SEQUENCE: 27

Ser Asn Glu Val Gln Glu Val Phe Ala Lys
1               5                   10

<210> SEQ ID NO 28
<211> LENGTH: 10
<212> TYPE: PRT
<213> ORGANISM: Bacillus anthracis

<400> SEQUENCE: 28

Glu Val Gln Glu Val Phe Ala Lys Ala Phe
1               5                   10

<210> SEQ ID NO 29
<211> LENGTH: 10
<212> TYPE: PRT
<213> ORGANISM: Bacillus anthracis

<400> SEQUENCE: 29

Gln His Arg Asp Val Leu Gln Leu Tyr Ala
1               5                   10

<210> SEQ ID NO 30
<211> LENGTH: 10
<212> TYPE: PRT
<213> ORGANISM: Bacillus anthracis

<400> SEQUENCE: 30

Arg Asp Val Leu Gln Leu Tyr Ala Pro Glu
1               5                   10

<210> SEQ ID NO 31
<211> LENGTH: 10
<212> TYPE: PRT
<213> ORGANISM: Bacillus anthracis

<400> SEQUENCE: 31

Val Leu Gln Leu Tyr Ala Pro Glu Ala Phe
1               5                   10

<210> SEQ ID NO 32
<211> LENGTH: 10
<212> TYPE: PRT
<213> ORGANISM: Bacillus anthracis

<400> SEQUENCE: 32

Gln Leu Tyr Ala Pro Glu Ala Phe Asn Tyr
1               5                   10

<210> SEQ ID NO 33
<211> LENGTH: 10
<212> TYPE: PRT
<213> ORGANISM: Bacillus anthracis

<400> SEQUENCE: 33

Tyr Ala Pro Glu Ala Phe Asn Tyr Met Asp
1               5                   10

<210> SEQ ID NO 34
<211> LENGTH: 10
<212> TYPE: PRT
<213> ORGANISM: Bacillus anthracis

<400> SEQUENCE: 34

Pro Glu Ala Phe Asn Tyr Met Asp Lys Phe
1               5                   10

<210> SEQ ID NO 35
<211> LENGTH: 10
<212> TYPE: PRT
<213> ORGANISM: Bacillus anthracis

<400> SEQUENCE: 35

Ala Phe Asn Tyr Met Asp Lys Phe Asn Glu
1               5                   10

<210> SEQ ID NO 36
<211> LENGTH: 10
<212> TYPE: PRT
<213> ORGANISM: Bacillus anthracis

<400> SEQUENCE: 36

Asn Tyr Met Asp Lys Phe Asn Glu Gln Glu
1               5                   10

<210> SEQ ID NO 37
<211> LENGTH: 10
<212> TYPE: PRT
<213> ORGANISM: Bacillus anthracis

<400> SEQUENCE: 37

Met Asp Lys Phe Asn Glu Gln Glu Ile Asn
1               5                   10

<210> SEQ ID NO 38
<211> LENGTH: 10
<212> TYPE: PRT
<213> ORGANISM: Bacillus anthracis

<400> SEQUENCE: 38

Lys Phe Asn Glu Gln Glu Ile Asn Leu Ser
1               5                   10

<210> SEQ ID NO 39

```
<211> LENGTH: 10
<212> TYPE: PRT
<213> ORGANISM: Bacillus anthracis

<400> SEQUENCE: 39

Asn Glu Gln Glu Ile Asn Leu Ser Leu Glu
1               5                   10

<210> SEQ ID NO 40
<211> LENGTH: 10
<212> TYPE: PRT
<213> ORGANISM: Bacillus anthracis

<400> SEQUENCE: 40

Gln Glu Ile Asn Leu Ser Leu Glu Glu Leu
1               5                   10

<210> SEQ ID NO 41
<211> LENGTH: 10
<212> TYPE: PRT
<213> ORGANISM: Bacillus anthracis

<400> SEQUENCE: 41

Ile Asn Leu Ser Leu Glu Glu Leu Lys Asp
1               5                   10

<210> SEQ ID NO 42
<211> LENGTH: 10
<212> TYPE: PRT
<213> ORGANISM: Bacillus anthracis

<400> SEQUENCE: 42

Leu Glu Glu Leu Lys Asp Gln Arg Met Leu
1               5                   10

<210> SEQ ID NO 43
<211> LENGTH: 10
<212> TYPE: PRT
<213> ORGANISM: Bacillus anthracis

<400> SEQUENCE: 43

Glu Leu Lys Asp Gln Arg Met Leu Ala Arg
1               5                   10

<210> SEQ ID NO 44
<211> LENGTH: 10
<212> TYPE: PRT
<213> ORGANISM: Bacillus anthracis

<400> SEQUENCE: 44

Met Leu Ala Arg Tyr Glu Lys Trp Glu Lys
1               5                   10

<210> SEQ ID NO 45
<211> LENGTH: 10
<212> TYPE: PRT
<213> ORGANISM: Bacillus anthracis

<400> SEQUENCE: 45

Ala Arg Tyr Glu Lys Trp Glu Lys Ile Lys
1               5                   10

<210> SEQ ID NO 46
<211> LENGTH: 10
<212> TYPE: PRT
```

<213> ORGANISM: Bacillus anthracis

<400> SEQUENCE: 46

Tyr Glu Lys Trp Glu Lys Ile Lys Gln His
1               5                   10

<210> SEQ ID NO 47
<211> LENGTH: 10
<212> TYPE: PRT
<213> ORGANISM: Bacillus anthracis

<400> SEQUENCE: 47

Leu Leu Lys Lys Leu Gln Ile Pro Ile Glu
1               5                   10

<210> SEQ ID NO 48
<211> LENGTH: 10
<212> TYPE: PRT
<213> ORGANISM: Bacillus anthracis

<400> SEQUENCE: 48

Ser Leu Ser Gln Glu Glu Lys Glu Leu Leu
1               5                   10

<210> SEQ ID NO 49
<211> LENGTH: 10
<212> TYPE: PRT
<213> ORGANISM: Bacillus anthracis

<400> SEQUENCE: 49

Ser Gln Glu Glu Lys Glu Leu Leu Lys Arg
1               5                   10

<210> SEQ ID NO 50
<211> LENGTH: 10
<212> TYPE: PRT
<213> ORGANISM: Bacillus anthracis

<400> SEQUENCE: 50

Glu Glu Lys Glu Leu Leu Lys Arg Ile Gln
1               5                   10

<210> SEQ ID NO 51
<211> LENGTH: 10
<212> TYPE: PRT
<213> ORGANISM: Bacillus anthracis

<400> SEQUENCE: 51

Asp Phe Leu Ser Thr Glu Glu Lys Glu Phe
1               5                   10

<210> SEQ ID NO 52
<211> LENGTH: 10
<212> TYPE: PRT
<213> ORGANISM: Bacillus anthracis

<400> SEQUENCE: 52

Leu Ser Thr Glu Glu Lys Glu Phe Leu Lys
1               5                   10

<210> SEQ ID NO 53
<211> LENGTH: 10
<212> TYPE: PRT
<213> ORGANISM: Bacillus anthracis

<400> SEQUENCE: 53

Thr Glu Glu Lys Glu Phe Leu Lys Lys Leu
1               5                   10

<210> SEQ ID NO 54
<211> LENGTH: 10
<212> TYPE: PRT
<213> ORGANISM: Bacillus anthracis

<400> SEQUENCE: 54

Glu Lys Glu Phe Leu Lys Lys Leu Gln Ile
1               5                   10

<210> SEQ ID NO 55
<211> LENGTH: 10
<212> TYPE: PRT
<213> ORGANISM: Bacillus anthracis

<400> SEQUENCE: 55

Glu Phe Leu Lys Lys Leu Gln Ile Asp Ile
1               5                   10

<210> SEQ ID NO 56
<211> LENGTH: 10
<212> TYPE: PRT
<213> ORGANISM: Bacillus anthracis

<400> SEQUENCE: 56

Ser Leu Ser Glu Glu Lys Glu Leu Leu
1               5                   10

<210> SEQ ID NO 57
<211> LENGTH: 10
<212> TYPE: PRT
<213> ORGANISM: Bacillus anthracis

<400> SEQUENCE: 57

Ser Glu Glu Glu Lys Glu Leu Leu Asn Arg
1               5                   10

<210> SEQ ID NO 58
<211> LENGTH: 10
<212> TYPE: PRT
<213> ORGANISM: Bacillus anthracis

<400> SEQUENCE: 58

Glu Glu Lys Glu Leu Leu Asn Arg Ile Gln
1               5                   10

<210> SEQ ID NO 59
<211> LENGTH: 10
<212> TYPE: PRT
<213> ORGANISM: Bacillus anthracis

<400> SEQUENCE: 59

Leu Ser Glu Lys Glu Lys Glu Phe Leu Lys
1               5                   10

<210> SEQ ID NO 60
<211> LENGTH: 10
<212> TYPE: PRT
<213> ORGANISM: Bacillus anthracis

<400> SEQUENCE: 60

Glu Lys Glu Lys Glu Phe Leu Lys Lys Leu
1               5                   10

<210> SEQ ID NO 61
<211> LENGTH: 10
<212> TYPE: PRT
<213> ORGANISM: Bacillus anthracis

<400> SEQUENCE: 61

Glu Lys Glu Phe Leu Lys Lys Leu Lys Leu
1               5                   10

<210> SEQ ID NO 62
<211> LENGTH: 10
<212> TYPE: PRT
<213> ORGANISM: Bacillus anthracis

<400> SEQUENCE: 62

Glu Phe Leu Lys Lys Leu Lys Leu Asp Ile
1               5                   10

<210> SEQ ID NO 63
<211> LENGTH: 10
<212> TYPE: PRT
<213> ORGANISM: Bacillus anthracis

<400> SEQUENCE: 63

Gln Pro Tyr Asp Ile Asn Gln Arg Leu Gln
1               5                   10

<210> SEQ ID NO 64
<211> LENGTH: 10
<212> TYPE: PRT
<213> ORGANISM: Bacillus anthracis

<400> SEQUENCE: 64

Tyr Asp Ile Asn Gln Arg Leu Gln Asp Thr
1               5                   10

<210> SEQ ID NO 65
<211> LENGTH: 10
<212> TYPE: PRT
<213> ORGANISM: Bacillus anthracis

<400> SEQUENCE: 65

Leu Ile Asp Ser Pro Ser Ile Asn Leu Asp
1               5                   10

<210> SEQ ID NO 66
<211> LENGTH: 10
<212> TYPE: PRT
<213> ORGANISM: Bacillus anthracis

<400> SEQUENCE: 66

Asp Ser Pro Ser Ile Asn Leu Asp Val Arg
1               5                   10

<210> SEQ ID NO 67
<211> LENGTH: 10
<212> TYPE: PRT
<213> ORGANISM: Bacillus anthracis

<400> SEQUENCE: 67

Pro Ser Ile Asn Leu Asp Val Arg Lys Gln
1               5                   10

<210> SEQ ID NO 68
<211> LENGTH: 10
<212> TYPE: PRT
<213> ORGANISM: Bacillus anthracis

<400> SEQUENCE: 68

Asn Arg Gly Ile Phe Asn Glu Phe Lys Lys
1               5                   10

<210> SEQ ID NO 69
<211> LENGTH: 10
<212> TYPE: PRT
<213> ORGANISM: Bacillus anthracis

<400> SEQUENCE: 69

Lys Tyr Ser Ile Ser Ser Asn Tyr Met Ile
1               5                   10

<210> SEQ ID NO 70
<211> LENGTH: 10
<212> TYPE: PRT
<213> ORGANISM: Bacillus anthracis

<400> SEQUENCE: 70

Ser Ile Ser Ser Asn Tyr Met Ile Val Asp
1               5                   10

<210> SEQ ID NO 71
<211> LENGTH: 10
<212> TYPE: PRT
<213> ORGANISM: Bacillus anthracis

<400> SEQUENCE: 71

Leu Ile Lys Lys Val Thr Asn Tyr Leu Val
1               5                   10

<210> SEQ ID NO 72
<211> LENGTH: 10
<212> TYPE: PRT
<213> ORGANISM: Bacillus anthracis

<400> SEQUENCE: 72

Lys Lys Val Thr Asn Tyr Leu Val Asp Gly
1               5                   10

<210> SEQ ID NO 73
<211> LENGTH: 10
<212> TYPE: PRT
<213> ORGANISM: Bacillus anthracis

<400> SEQUENCE: 73

Leu Val Asp Gly Asn Gly Arg Phe Val Phe
1               5                   10

<210> SEQ ID NO 74
<211> LENGTH: 10
<212> TYPE: PRT
<213> ORGANISM: Bacillus anthracis

<400> SEQUENCE: 74

Asp Gly Asn Gly Arg Phe Val Phe Thr Asp
1               5                   10

```
<210> SEQ ID NO 75
<211> LENGTH: 10
<212> TYPE: PRT
<213> ORGANISM: Bacillus anthracis

<400> SEQUENCE: 75

Asn Gly Arg Phe Val Phe Thr Asp Ile Thr
1               5                   10

<210> SEQ ID NO 76
<211> LENGTH: 10
<212> TYPE: PRT
<213> ORGANISM: Bacillus anthracis

<400> SEQUENCE: 76

Arg Phe Val Phe Thr Asp Ile Thr Leu Pro
1               5                   10

<210> SEQ ID NO 77
<211> LENGTH: 10
<212> TYPE: PRT
<213> ORGANISM: Bacillus anthracis

<400> SEQUENCE: 77

Gln Tyr Thr His Gln Asp Glu Ile Tyr Glu
1               5                   10

<210> SEQ ID NO 78
<211> LENGTH: 10
<212> TYPE: PRT
<213> ORGANISM: Bacillus anthracis

<400> SEQUENCE: 78

Thr His Gln Asp Glu Ile Tyr Glu Gln Val
1               5                   10

<210> SEQ ID NO 79
<211> LENGTH: 10
<212> TYPE: PRT
<213> ORGANISM: Bacillus anthracis

<400> SEQUENCE: 79

Val Pro Glu Ser Arg Ser Ile Leu Leu His
1               5                   10

<210> SEQ ID NO 80
<211> LENGTH: 10
<212> TYPE: PRT
<213> ORGANISM: Bacillus anthracis

<400> SEQUENCE: 80

Glu Ser Arg Ser Ile Leu Leu His Gly Pro
1               5                   10

<210> SEQ ID NO 81
<211> LENGTH: 10
<212> TYPE: PRT
<213> ORGANISM: Bacillus anthracis

<400> SEQUENCE: 81

Asp Ser Glu Gly Phe Ile His Glu Phe Gly
1               5                   10

<210> SEQ ID NO 82
<211> LENGTH: 10
```

```
<212> TYPE: PRT
<213> ORGANISM: Bacillus anthracis

<400> SEQUENCE: 82

Glu Gly Phe Ile His Glu Phe Gly His Ala
1               5                   10

<210> SEQ ID NO 83
<211> LENGTH: 10
<212> TYPE: PRT
<213> ORGANISM: Bacillus anthracis

<400> SEQUENCE: 83

Phe Ile His Glu Phe Gly His Ala Val Asp
1               5                   10

<210> SEQ ID NO 84
<211> LENGTH: 10
<212> TYPE: PRT
<213> ORGANISM: Bacillus anthracis

<400> SEQUENCE: 84

Asn Ser Lys Lys Phe Ile Asp Ile Phe Lys
1               5                   10

<210> SEQ ID NO 85
<211> LENGTH: 10
<212> TYPE: PRT
<213> ORGANISM: Bacillus anthracis

<400> SEQUENCE: 85

Lys Lys Phe Ile Asp Ile Phe Lys Glu Glu
1               5                   10

<210> SEQ ID NO 86
<211> LENGTH: 10
<212> TYPE: PRT
<213> ORGANISM: Bacillus anthracis

<400> SEQUENCE: 86

Asp His Ala Glu Arg Leu Lys Val Gln Lys
1               5                   10

<210> SEQ ID NO 87
<211> LENGTH: 10
<212> TYPE: PRT
<213> ORGANISM: Bacillus anthracis

<400> SEQUENCE: 87

Ala Glu Arg Leu Lys Val Gln Lys Asn Ala
1               5                   10

<210> SEQ ID NO 88
<211> LENGTH: 10
<212> TYPE: PRT
<213> ORGANISM: Bacillus anthracis

<400> SEQUENCE: 88

Arg Leu Lys Val Gln Lys Asn Ala Pro Lys
1               5                   10

<210> SEQ ID NO 89
<211> LENGTH: 10
<212> TYPE: PRT
<213> ORGANISM: Bacillus anthracis
```

```
<400> SEQUENCE: 89

Lys Val Gln Lys Asn Ala Pro Lys Thr Phe
1               5                   10

<210> SEQ ID NO 90
<211> LENGTH: 10
<212> TYPE: PRT
<213> ORGANISM: Bacillus anthracis

<400> SEQUENCE: 90

Pro Lys Thr Phe Gln Phe Ile Asn Asp Gln
1               5                   10

<210> SEQ ID NO 91
<211> LENGTH: 10
<212> TYPE: PRT
<213> ORGANISM: Bacillus anthracis

<400> SEQUENCE: 91

Thr Phe Gln Phe Ile Asn Asp Gln Ile Lys
1               5                   10

<210> SEQ ID NO 92
<211> LENGTH: 16
<212> TYPE: PRT
<213> ORGANISM: Bacillus anthracis

<400> SEQUENCE: 92

Gly Ala Gly Gly His Gly Asp Val Gly Met His Val Lys Glu Lys Glu
1               5                   10                  15

<210> SEQ ID NO 93
<211> LENGTH: 12
<212> TYPE: PRT
<213> ORGANISM: Bacillus anthracis

<400> SEQUENCE: 93

Lys Glu Lys Asn Lys Asp Glu Asn Lys Arg Lys Asp
1               5                   10

<210> SEQ ID NO 94
<211> LENGTH: 16
<212> TYPE: PRT
<213> ORGANISM: Bacillus anthracis

<400> SEQUENCE: 94

Arg Asn Lys Thr Gln Glu Glu His Leu Lys Glu Ile Met Lys His Ile
1               5                   10                  15

<210> SEQ ID NO 95
<211> LENGTH: 18
<212> TYPE: PRT
<213> ORGANISM: Bacillus anthracis

<400> SEQUENCE: 95

Glu Lys Val Pro Ser Asp Val Leu Glu Met Tyr Lys Ala Ile Gly Gly
1               5                   10                  15

Lys Ile

<210> SEQ ID NO 96
<211> LENGTH: 20
<212> TYPE: PRT
<213> ORGANISM: Bacillus anthracis
```

-continued

```
<400> SEQUENCE: 96

Ser Glu Asp Lys Lys Ile Lys Asp Ile Tyr Gly Lys Asp Ala Leu
1               5                   10                  15

Leu His Glu His
            20

<210> SEQ ID NO 97
<211> LENGTH: 12
<212> TYPE: PRT
<213> ORGANISM: Bacillus anthracis

<400> SEQUENCE: 97

Leu His Glu His Tyr Val Tyr Ala Lys Glu Gly Tyr
1               5                   10

<210> SEQ ID NO 98
<211> LENGTH: 12
<212> TYPE: PRT
<213> ORGANISM: Bacillus anthracis

<400> SEQUENCE: 98

Ser Asn Glu Val Gln Glu Val Phe Ala Lys Ala Phe
1               5                   10

<210> SEQ ID NO 99
<211> LENGTH: 34
<212> TYPE: PRT
<213> ORGANISM: Bacillus anthracis

<400> SEQUENCE: 99

Gln His Arg Asp Val Leu Gln Leu Tyr Ala Pro Glu Ala Phe Asn Tyr
1               5                   10                  15

Met Asp Lys Phe Asn Glu Gln Glu Ile Asn Leu Ser Leu Glu Glu Leu
            20                  25                  30

Lys Asp

<210> SEQ ID NO 100
<211> LENGTH: 12
<212> TYPE: PRT
<213> ORGANISM: Bacillus anthracis

<400> SEQUENCE: 100

Leu Glu Glu Leu Lys Asp Gln Arg Met Leu Ala Arg
1               5                   10

<210> SEQ ID NO 101
<211> LENGTH: 14
<212> TYPE: PRT
<213> ORGANISM: Bacillus anthracis

<400> SEQUENCE: 101

Met Leu Ala Arg Tyr Glu Lys Trp Glu Lys Ile Lys Gln His
1               5                   10

<210> SEQ ID NO 102
<211> LENGTH: 14
<212> TYPE: PRT
<213> ORGANISM: Bacillus anthracis

<400> SEQUENCE: 102

Ser Leu Ser Gln Glu Glu Lys Glu Leu Leu Lys Arg Ile Gln
1               5                   10
```

<210> SEQ ID NO 103
<211> LENGTH: 18
<212> TYPE: PRT
<213> ORGANISM: Bacillus anthracis

<400> SEQUENCE: 103

Asp Phe Leu Ser Thr Glu Glu Lys Glu Phe Leu Lys Lys Leu Gln Ile
1               5                   10                  15

Asp Ile

<210> SEQ ID NO 104
<211> LENGTH: 14
<212> TYPE: PRT
<213> ORGANISM: Bacillus anthracis

<400> SEQUENCE: 104

Ser Leu Ser Glu Glu Glu Lys Glu Leu Leu Asn Arg Ile Gln
1               5                   10

<210> SEQ ID NO 105
<211> LENGTH: 16
<212> TYPE: PRT
<213> ORGANISM: Bacillus anthracis

<400> SEQUENCE: 105

Leu Ser Glu Lys Glu Lys Glu Phe Leu Lys Lys Leu Lys Leu Asp Ile
1               5                   10                  15

<210> SEQ ID NO 106
<211> LENGTH: 12
<212> TYPE: PRT
<213> ORGANISM: Bacillus anthracis

<400> SEQUENCE: 106

Gln Pro Tyr Asp Ile Asn Gln Arg Leu Gln Asp Thr
1               5                   10

<210> SEQ ID NO 107
<211> LENGTH: 14
<212> TYPE: PRT
<213> ORGANISM: Bacillus anthracis

<400> SEQUENCE: 107

Leu Ile Asp Ser Pro Ser Ile Asn Leu Asp Val Arg Lys Gln
1               5                   10

<210> SEQ ID NO 108
<211> LENGTH: 12
<212> TYPE: PRT
<213> ORGANISM: Bacillus anthracis

<400> SEQUENCE: 108

Lys Tyr Ser Ile Ser Ser Asn Tyr Met Ile Val Asp
1               5                   10

<210> SEQ ID NO 109
<211> LENGTH: 12
<212> TYPE: PRT
<213> ORGANISM: Bacillus anthracis

<400> SEQUENCE: 109

Leu Ile Lys Lys Val Thr Asn Tyr Leu Val Asp Gly
1               5                   10

<210> SEQ ID NO 110
<211> LENGTH: 16
<212> TYPE: PRT
<213> ORGANISM: Bacillus anthracis

<400> SEQUENCE: 110

Leu Val Asp Gly Asn Gly Arg Phe Val Phe Thr Asp Ile Thr Leu Pro
1               5                   10                  15

<210> SEQ ID NO 111
<211> LENGTH: 12
<212> TYPE: PRT
<213> ORGANISM: Bacillus anthracis

<400> SEQUENCE: 111

Gln Tyr Thr His Gln Asp Glu Ile Tyr Glu Gln Val
1               5                   10

<210> SEQ ID NO 112
<211> LENGTH: 12
<212> TYPE: PRT
<213> ORGANISM: Bacillus anthracis

<400> SEQUENCE: 112

Val Pro Glu Ser Arg Ser Ile Leu Leu His Gly Pro
1               5                   10

<210> SEQ ID NO 113
<211> LENGTH: 14
<212> TYPE: PRT
<213> ORGANISM: Bacillus anthracis

<400> SEQUENCE: 113

Asp Ser Glu Gly Phe Ile His Glu Phe Gly His Ala Val Asp
1               5                   10

<210> SEQ ID NO 114
<211> LENGTH: 12
<212> TYPE: PRT
<213> ORGANISM: Bacillus anthracis

<400> SEQUENCE: 114

Asn Ser Lys Lys Phe Ile Asp Ile Phe Lys Glu Glu
1               5                   10

<210> SEQ ID NO 115
<211> LENGTH: 16
<212> TYPE: PRT
<213> ORGANISM: Bacillus anthracis

<400> SEQUENCE: 115

Asp His Ala Glu Arg Leu Lys Val Gln Lys Asn Ala Pro Lys Thr Phe
1               5                   10                  15

<210> SEQ ID NO 116
<211> LENGTH: 12
<212> TYPE: PRT
<213> ORGANISM: Bacillus anthracis

<400> SEQUENCE: 116

Pro Lys Thr Phe Gln Phe Ile Asn Asp Gln Ile Lys
1               5                   10

<210> SEQ ID NO 117
<211> LENGTH: 10
<212> TYPE: PRT
<213> ORGANISM: Bacillus anthracis

<400> SEQUENCE: 117

Val Gln Gly Ala Gly Gly His Gly Asp Val
1               5                   10

<210> SEQ ID NO 118
<211> LENGTH: 10
<212> TYPE: PRT
<213> ORGANISM: Bacillus anthracis

<400> SEQUENCE: 118

Lys Glu Lys Glu Lys Asn Lys Asp Glu Asn
1               5                   10

<210> SEQ ID NO 119
<211> LENGTH: 10
<212> TYPE: PRT
<213> ORGANISM: Bacillus anthracis

<400> SEQUENCE: 119

Lys Arg Lys Asp Glu Glu Arg Asn Lys Thr
1               5                   10

<210> SEQ ID NO 120
<211> LENGTH: 10
<212> TYPE: PRT
<213> ORGANISM: Bacillus anthracis

<400> SEQUENCE: 120

Lys Asp Glu Glu Arg Asn Lys Thr Gln Glu
1               5                   10

<210> SEQ ID NO 121
<211> LENGTH: 10
<212> TYPE: PRT
<213> ORGANISM: Bacillus anthracis

<400> SEQUENCE: 121

Ile Ser Leu Glu Ala Leu Ser Glu Asp Lys
1               5                   10

<210> SEQ ID NO 122
<211> LENGTH: 10
<212> TYPE: PRT
<213> ORGANISM: Bacillus anthracis

<400> SEQUENCE: 122

Leu Glu Ala Leu Ser Glu Asp Lys Lys Lys
1               5                   10

<210> SEQ ID NO 123
<211> LENGTH: 10
<212> TYPE: PRT
<213> ORGANISM: Bacillus anthracis

<400> SEQUENCE: 123

Ala Leu Ser Glu Asp Lys Lys Lys Ile Lys
1               5                   10

<210> SEQ ID NO 124
<211> LENGTH: 10

```
<212> TYPE: PRT
<213> ORGANISM: Bacillus anthracis

<400> SEQUENCE: 124

Asp Phe Ser Val Glu Phe Leu Glu Gln Asn
1               5                   10

<210> SEQ ID NO 125
<211> LENGTH: 10
<212> TYPE: PRT
<213> ORGANISM: Bacillus anthracis

<400> SEQUENCE: 125

Lys Lys Leu Gln Ile Pro Ile Glu Pro Lys
1               5                   10

<210> SEQ ID NO 126
<211> LENGTH: 10
<212> TYPE: PRT
<213> ORGANISM: Bacillus anthracis

<400> SEQUENCE: 126

Leu Lys Lys Leu Lys Leu Asp Ile Gln Pro
1               5                   10

<210> SEQ ID NO 127
<211> LENGTH: 10
<212> TYPE: PRT
<213> ORGANISM: Bacillus anthracis

<400> SEQUENCE: 127

Asp Ile Gln Pro Tyr Asp Ile Asn Gln Arg
1               5                   10

<210> SEQ ID NO 128
<211> LENGTH: 10
<212> TYPE: PRT
<213> ORGANISM: Bacillus anthracis

<400> SEQUENCE: 128

Ile Asn Gln Arg Leu Gln Asp Thr Gly Gly
1               5                   10

<210> SEQ ID NO 129
<211> LENGTH: 10
<212> TYPE: PRT
<213> ORGANISM: Bacillus anthracis

<400> SEQUENCE: 129

Ile Asn Leu Asp Val Arg Lys Gln Tyr Lys
1               5                   10

<210> SEQ ID NO 130
<211> LENGTH: 10
<212> TYPE: PRT
<213> ORGANISM: Bacillus anthracis

<400> SEQUENCE: 130

Leu Asp Val Arg Lys Gln Tyr Lys Arg Asp
1               5                   10

<210> SEQ ID NO 131
<211> LENGTH: 10
<212> TYPE: PRT
<213> ORGANISM: Bacillus anthracis
```

```
<400> SEQUENCE: 131

Gly Ile Phe Asn Glu Phe Lys Lys Asn Phe
1               5                   10

<210> SEQ ID NO 132
<211> LENGTH: 10
<212> TYPE: PRT
<213> ORGANISM: Bacillus anthracis

<400> SEQUENCE: 132

Asn Ile Ala Glu Gln Tyr Thr His Gln Asp
1               5                   10

<210> SEQ ID NO 133
<211> LENGTH: 10
<212> TYPE: PRT
<213> ORGANISM: Bacillus anthracis

<400> SEQUENCE: 133

Gln Asp Glu Ile Tyr Glu Gln Val His Ser
1               5                   10

<210> SEQ ID NO 134
<211> LENGTH: 10
<212> TYPE: PRT
<213> ORGANISM: Bacillus anthracis

<400> SEQUENCE: 134

Glu Ile Tyr Glu Gln Val His Ser Lys Gly
1               5                   10

<210> SEQ ID NO 135
<211> LENGTH: 10
<212> TYPE: PRT
<213> ORGANISM: Bacillus anthracis

<400> SEQUENCE: 135

Arg Ser Ile Leu Leu His Gly Pro Ser Lys
1               5                   10

<210> SEQ ID NO 136
<211> LENGTH: 10
<212> TYPE: PRT
<213> ORGANISM: Bacillus anthracis

<400> SEQUENCE: 136

Ile Leu Leu His Gly Pro Ser Lys Gly Val
1               5                   10

<210> SEQ ID NO 137
<211> LENGTH: 10
<212> TYPE: PRT
<213> ORGANISM: Bacillus anthracis

<400> SEQUENCE: 137

Gln Lys Asn Ala Pro Lys Thr Phe Gln Phe
1               5                   10

<210> SEQ ID NO 138
<211> LENGTH: 10
<212> TYPE: PRT
<213> ORGANISM: Bacillus anthracis

<400> SEQUENCE: 138
```

```
Gln Phe Ile Asn Asp Gln Ile Lys Phe Ile
1               5                   10
```

<210> SEQ ID NO 139
<211> LENGTH: 18
<212> TYPE: PRT
<213> ORGANISM: Bacillus anthracis

<400> SEQUENCE: 139

```
Val Gln Gly Ala Gly Gly His Gly Asp Val Gly Met His Val Lys Glu
1               5                   10                  15

Lys Glu
```

<210> SEQ ID NO 140
<211> LENGTH: 14
<212> TYPE: PRT
<213> ORGANISM: Bacillus anthracis

<400> SEQUENCE: 140

```
Lys Glu Lys Glu Lys Asn Lys Asp Glu Asn Lys Arg Lys Asp
1               5                   10
```

<210> SEQ ID NO 141
<211> LENGTH: 12
<212> TYPE: PRT
<213> ORGANISM: Bacillus anthracis

<400> SEQUENCE: 141

```
Lys Arg Lys Asp Glu Glu Arg Asn Lys Thr Gln Glu
1               5                   10
```

<210> SEQ ID NO 142
<211> LENGTH: 26
<212> TYPE: PRT
<213> ORGANISM: Bacillus anthracis

<400> SEQUENCE: 142

```
Ile Ser Leu Glu Ala Leu Ser Glu Asp Lys Lys Ile Lys Asp Ile
1               5                   10                  15

Tyr Gly Lys Asp Ala Leu Leu His Glu His
            20                  25
```

<210> SEQ ID NO 143
<211> LENGTH: 18
<212> TYPE: PRT
<213> ORGANISM: Bacillus anthracis

<400> SEQUENCE: 143

```
Leu Ser Glu Lys Glu Lys Glu Phe Leu Lys Lys Leu Lys Leu Asp Ile
1               5                   10                  15

Gln Pro
```

<210> SEQ ID NO 144
<211> LENGTH: 12
<212> TYPE: PRT
<213> ORGANISM: Bacillus anthracis

<400> SEQUENCE: 144

```
Leu Leu Lys Lys Leu Gln Ile Pro Ile Glu Pro Lys
1               5                   10
```

<210> SEQ ID NO 145

```
<211> LENGTH: 16
<212> TYPE: PRT
<213> ORGANISM: Bacillus anthracis

<400> SEQUENCE: 145

Asp Ile Gln Pro Tyr Asp Ile Asn Gln Arg Leu Gln Asp Thr Gly Gly
1               5                   10                  15

<210> SEQ ID NO 146
<211> LENGTH: 18
<212> TYPE: PRT
<213> ORGANISM: Bacillus anthracis

<400> SEQUENCE: 146

Leu Ile Asp Ser Pro Ser Ile Asn Leu Asp Val Arg Lys Gln Tyr Lys
1               5                   10                  15

Arg Asp

<210> SEQ ID NO 147
<211> LENGTH: 12
<212> TYPE: PRT
<213> ORGANISM: Bacillus anthracis

<400> SEQUENCE: 147

Asn Arg Gly Ile Phe Asn Glu Phe Lys Lys Asn Phe
1               5                   10

<210> SEQ ID NO 148
<211> LENGTH: 16
<212> TYPE: PRT
<213> ORGANISM: Bacillus anthracis

<400> SEQUENCE: 148

Gln Tyr Thr His Gln Asp Glu Ile Tyr Glu Gln Val His Ser Lys Gly
1               5                   10                  15

<210> SEQ ID NO 149
<211> LENGTH: 16
<212> TYPE: PRT
<213> ORGANISM: Bacillus anthracis

<400> SEQUENCE: 149

Val Pro Glu Ser Arg Ser Ile Leu Leu His Gly Pro Ser Lys Gly Val
1               5                   10                  15

<210> SEQ ID NO 150
<211> LENGTH: 18
<212> TYPE: PRT
<213> ORGANISM: Bacillus anthracis

<400> SEQUENCE: 150

Asp His Ala Glu Arg Leu Lys Val Gln Lys Asn Ala Pro Lys Thr Phe
1               5                   10                  15

Gln Phe

<210> SEQ ID NO 151
<211> LENGTH: 14
<212> TYPE: PRT
<213> ORGANISM: Bacillus anthracis

<400> SEQUENCE: 151

Pro Lys Thr Phe Gln Phe Ile Asn Asp Gln Ile Lys Phe Ile
1               5                   10
```

<210> SEQ ID NO 152
<211> LENGTH: 16
<212> TYPE: PRT
<213> ORGANISM: Bacillus anthracis

<400> SEQUENCE: 152

Phe Ser Asp Leu Asn Phe Gln Ala Pro Met Val Val Thr Ser Ser Thr
1               5                   10                  15

<210> SEQ ID NO 153
<211> LENGTH: 20
<212> TYPE: PRT
<213> ORGANISM: Bacillus anthracis

<400> SEQUENCE: 153

Ser Thr Thr Gly Asp Leu Ser Ile Pro Ser Ser Glu Leu Glu Asn Ile
1               5                   10                  15

Pro Ser Glu Asn
            20

<210> SEQ ID NO 154
<211> LENGTH: 14
<212> TYPE: PRT
<213> ORGANISM: Bacillus anthracis

<400> SEQUENCE: 154

Tyr Gln Arg Glu Asn Pro Thr Glu Lys Gly Leu Asp Phe Lys
1               5                   10

<210> SEQ ID NO 155
<211> LENGTH: 16
<212> TYPE: PRT
<213> ORGANISM: Bacillus anthracis

<400> SEQUENCE: 155

Leu Tyr Trp Thr Asp Ser Gln Asn Lys Lys Glu Val Ile Ser Ser Asp
1               5                   10                  15

<210> SEQ ID NO 156
<211> LENGTH: 22
<212> TYPE: PRT
<213> ORGANISM: Bacillus anthracis

<400> SEQUENCE: 156

Leu Lys Gln Lys Ser Ser Asn Ser Arg Lys Lys Arg Ser Thr Ser Ala
1               5                   10                  15

Gly Pro Thr Val Pro Asp
            20

<210> SEQ ID NO 157
<211> LENGTH: 12
<212> TYPE: PRT
<213> ORGANISM: Bacillus anthracis

<400> SEQUENCE: 157

Gly Pro Thr Val Pro Asp Arg Asp Asn Asp Gly Ile
1               5                   10

<210> SEQ ID NO 158
<211> LENGTH: 12
<212> TYPE: PRT
<213> ORGANISM: Bacillus anthracis

<400> SEQUENCE: 158

Glu Gly Tyr Thr Val Asp Val Lys Asn Lys Arg Thr
1               5                   10

<210> SEQ ID NO 159
<211> LENGTH: 20
<212> TYPE: PRT
<213> ORGANISM: Bacillus anthracis

<400> SEQUENCE: 159

Ser Asn Ile His Glu Lys Lys Gly Leu Thr Lys Tyr Lys Ser Ser Pro
1               5                   10                  15

Glu Lys Trp Ser
            20

<210> SEQ ID NO 160
<211> LENGTH: 22
<212> TYPE: PRT
<213> ORGANISM: Bacillus anthracis

<400> SEQUENCE: 160

Thr Ala Ser Asp Pro Tyr Ser Asp Phe Glu Lys Val Thr Gly Arg Ile
1               5                   10                  15

Asp Lys Asn Val Ser Pro
            20

<210> SEQ ID NO 161
<211> LENGTH: 10
<212> TYPE: PRT
<213> ORGANISM: Bacillus anthracis

<400> SEQUENCE: 161

Ser Pro Glu Ala Arg His Pro Leu Val Ala
1               5                   10

<210> SEQ ID NO 162
<211> LENGTH: 12
<212> TYPE: PRT
<213> ORGANISM: Bacillus anthracis

<400> SEQUENCE: 162

Val Ala Ala Tyr Pro Ile Val His Val Asp Met Glu
1               5                   10

<210> SEQ ID NO 163
<211> LENGTH: 18
<212> TYPE: PRT
<213> ORGANISM: Bacillus anthracis

<400> SEQUENCE: 163

Val Asp Met Glu Asn Ile Ile Leu Ser Lys Asn Glu Asp Gln Ser Thr
1               5                   10                  15

Gln Asn

<210> SEQ ID NO 164
<211> LENGTH: 18
<212> TYPE: PRT
<213> ORGANISM: Bacillus anthracis

<400> SEQUENCE: 164

Asn Ala Glu Val His Ala Ser Phe Phe Asp Ile Gly Gly Ser Val Ser
1               5                   10                  15

Ala Gly

<210> SEQ ID NO 165
<211> LENGTH: 10
<212> TYPE: PRT
<213> ORGANISM: Bacillus anthracis

<400> SEQUENCE: 165

Asn Thr Gly Thr Ala Pro Ile Tyr Asn Val
1               5                   10

<210> SEQ ID NO 166
<211> LENGTH: 14
<212> TYPE: PRT
<213> ORGANISM: Bacillus anthracis

<400> SEQUENCE: 166

Ala Lys Glu Asn Gln Leu Ser Gln Ile Leu Ala Pro Asn Asn
1               5                   10

<210> SEQ ID NO 167
<211> LENGTH: 10
<212> TYPE: PRT
<213> ORGANISM: Bacillus anthracis

<400> SEQUENCE: 167

Thr Leu Lys Glu Ala Leu Lys Ile Ala Phe
1               5                   10

<210> SEQ ID NO 168
<211> LENGTH: 16
<212> TYPE: PRT
<213> ORGANISM: Bacillus anthracis

<400> SEQUENCE: 168

Gly Lys Asp Ile Thr Glu Phe Asp Phe Asn Phe Asp Gln Gln Thr Ser
1               5                   10                  15

<210> SEQ ID NO 169
<211> LENGTH: 10
<212> TYPE: PRT
<213> ORGANISM: Bacillus anthracis

<400> SEQUENCE: 169

Gln Asn Ile Lys Asn Gln Leu Ala Glu Leu
1               5                   10

<210> SEQ ID NO 170
<211> LENGTH: 12
<212> TYPE: PRT
<213> ORGANISM: Bacillus anthracis

<400> SEQUENCE: 170

Leu Asp Lys Ile Lys Leu Asn Ala Lys Met Asn Ile
1               5                   10

<210> SEQ ID NO 171
<211> LENGTH: 14
<212> TYPE: PRT
<213> ORGANISM: Bacillus anthracis

<400> SEQUENCE: 171

Lys Arg Phe His Tyr Asp Arg Asn Asn Ile Ala Val Gly Ala
1               5                   10

<210> SEQ ID NO 172
<211> LENGTH: 22
<212> TYPE: PRT
<213> ORGANISM: Bacillus anthracis

<400> SEQUENCE: 172

Ala Val Gly Ala Asp Glu Ser Val Val Lys Glu Ala His Arg Glu Val
1               5                   10                  15

Ile Asn Ser Ser Thr Glu
            20

<210> SEQ ID NO 173
<211> LENGTH: 10
<212> TYPE: PRT
<213> ORGANISM: Bacillus anthracis

<400> SEQUENCE: 173

Thr Glu Gly Leu Leu Leu Asn Ile Asp Lys
1               5                   10

<210> SEQ ID NO 174
<211> LENGTH: 14
<212> TYPE: PRT
<213> ORGANISM: Bacillus anthracis

<400> SEQUENCE: 174

Leu Leu Asn Ile Asp Lys Asp Ile Arg Lys Ile Leu Ser Gly
1               5                   10

<210> SEQ ID NO 175
<211> LENGTH: 14
<212> TYPE: PRT
<213> ORGANISM: Bacillus anthracis

<400> SEQUENCE: 175

Lys Leu Pro Leu Tyr Ile Ser Asn Pro Asn Tyr Lys Val Asn
1               5                   10

<210> SEQ ID NO 176
<211> LENGTH: 12
<212> TYPE: PRT
<213> ORGANISM: Bacillus anthracis

<400> SEQUENCE: 176

Thr Lys Glu Asn Thr Ile Ile Asn Pro Ser Glu Asn
1               5                   10

<210> SEQ ID NO 177
<211> LENGTH: 16
<212> TYPE: PRT
<213> ORGANISM: Bacillus anthracis

<400> SEQUENCE: 177

Lys Glu Phe Ile Lys Val Ile Ser Met Ser Cys Leu Val Thr Ala Ile
1               5                   10                  15

<210> SEQ ID NO 178
<211> LENGTH: 12
<212> TYPE: PRT
<213> ORGANISM: Bacillus anthracis

<400> SEQUENCE: 178

Pro Val Phe Ile Pro Leu Val Gln Gly Ala Gly Gly
1               5                   10

```
<210> SEQ ID NO 179
<211> LENGTH: 14
<212> TYPE: PRT
<213> ORGANISM: Bacillus anthracis

<400> SEQUENCE: 179

Ser Glu Asp Lys Lys Ile Lys Asp Ile Tyr Gly Lys Asp
1               5                   10

<210> SEQ ID NO 180
<211> LENGTH: 12
<212> TYPE: PRT
<213> ORGANISM: Bacillus anthracis

<400> SEQUENCE: 180

Glu Leu Lys Asp Gln Arg Met Leu Ala Arg Tyr Glu
1               5                   10

<210> SEQ ID NO 181
<211> LENGTH: 14
<212> TYPE: PRT
<213> ORGANISM: Bacillus anthracis

<400> SEQUENCE: 181

Lys Ile Asp Thr Lys Ile Gln Glu Ala Gln Leu Asn Ile Asn
1               5                   10

<210> SEQ ID NO 182
<211> LENGTH: 14
<212> TYPE: PRT
<213> ORGANISM: Bacillus anthracis

<400> SEQUENCE: 182

Ala Gln Leu Asn Ile Asn Gln Glu Trp Asn Lys Ala Leu Gly
1               5                   10

<210> SEQ ID NO 183
<211> LENGTH: 14
<212> TYPE: PRT
<213> ORGANISM: Bacillus anthracis

<400> SEQUENCE: 183

Asn Val His Asn Arg Tyr Ala Ser Asn Ile Val Glu Ser Ala
1               5                   10

<210> SEQ ID NO 184
<211> LENGTH: 12
<212> TYPE: PRT
<213> ORGANISM: Bacillus anthracis

<400> SEQUENCE: 184

Thr Asp Ile Thr Leu Pro Asn Ile Ala Glu Gln Tyr
1               5                   10

<210> SEQ ID NO 185
<211> LENGTH: 18
<212> TYPE: PRT
<213> ORGANISM: Bacillus anthracis

<400> SEQUENCE: 185

Thr His Gln Asp Glu Ile Tyr Glu Gln Val His Ser Lys Gly Leu Tyr
1               5                   10                  15

Val Pro
```

-continued

```
<210> SEQ ID NO 186
<211> LENGTH: 18
<212> TYPE: PRT
<213> ORGANISM: Bacillus anthracis

<400> SEQUENCE: 186

Met His Ser Thr Asp His Ala Glu Arg Leu Lys Val Gln Lys Asn Ala
1               5                   10                  15

Pro Lys

<210> SEQ ID NO 187
<211> LENGTH: 14
<212> TYPE: PRT
<213> ORGANISM: Bacillus anthracis

<400> SEQUENCE: 187

Ile Gln Ala Glu Val Lys Gln Glu Asn Arg Leu Leu Asn Glu
1               5                   10

<210> SEQ ID NO 188
<211> LENGTH: 12
<212> TYPE: PRT
<213> ORGANISM: Bacillus anthracis

<400> SEQUENCE: 188

Glu Asn Gln Thr Phe Gln Ser Ala Ile Trp Ser Gly
1               5                   10

<210> SEQ ID NO 189
<211> LENGTH: 12
<212> TYPE: PRT
<213> ORGANISM: Bacillus anthracis

<400> SEQUENCE: 189

Phe Ile Lys Val Lys Lys Ser Asp Glu Tyr Thr Phe
1               5                   10

<210> SEQ ID NO 190
<211> LENGTH: 12
<212> TYPE: PRT
<213> ORGANISM: Bacillus anthracis

<400> SEQUENCE: 190

Asn Lys Ala Ser Asn Lys Ile Arg Leu Glu Lys Gly
1               5                   10

<210> SEQ ID NO 191
<211> LENGTH: 12
<212> TYPE: PRT
<213> ORGANISM: Bacillus anthracis

<400> SEQUENCE: 191

Asn Pro Thr Glu Lys Gly Leu Asp Phe Lys Leu Tyr
1               5                   10

<210> SEQ ID NO 192
<211> LENGTH: 10
<212> TYPE: PRT
<213> ORGANISM: Bacillus anthracis

<400> SEQUENCE: 192

Tyr Thr Val Asp Val Lys Asn Lys Arg Thr
1               5                   10
```

```
<210> SEQ ID NO 193
<211> LENGTH: 12
<212> TYPE: PRT
<213> ORGANISM: Bacillus anthracis

<400> SEQUENCE: 193

Ser Asp Phe Glu Lys Val Thr Gly Arg Ile Asp Lys
1               5                   10

<210> SEQ ID NO 194
<211> LENGTH: 12
<212> TYPE: PRT
<213> ORGANISM: Bacillus anthracis

<400> SEQUENCE: 194

Ser Thr Val Ala Ile Asp His Ser Leu Ser Leu Ala
1               5                   10

<210> SEQ ID NO 195
<211> LENGTH: 12
<212> TYPE: PRT
<213> ORGANISM: Bacillus anthracis

<400> SEQUENCE: 195

Ala Pro Asn Asn Tyr Tyr Pro Ser Lys Asn Leu Ala
1               5                   10

<210> SEQ ID NO 196
<211> LENGTH: 12
<212> TYPE: PRT
<213> ORGANISM: Bacillus anthracis

<400> SEQUENCE: 196

Ser Gly Phe Ile Lys Val Lys Lys Ser Asp Glu Tyr
1               5                   10

<210> SEQ ID NO 197
<211> LENGTH: 14
<212> TYPE: PRT
<213> ORGANISM: Bacillus anthracis

<400> SEQUENCE: 197

Asn Ser Asn Lys Ile Arg Leu Glu Lys Gly Arg Leu Tyr Gln
1               5                   10

<210> SEQ ID NO 198
<211> LENGTH: 20
<212> TYPE: PRT
<213> ORGANISM: Bacillus anthracis

<400> SEQUENCE: 198

Asn Pro Thr Glu Lys Gly Leu Asp Phe Lys Leu Tyr Trp Thr Asp Ser
1               5                   10                  15

Gln Asn Lys Lys
            20

<210> SEQ ID NO 199
<211> LENGTH: 20
<212> TYPE: PRT
<213> ORGANISM: Bacillus anthracis

<400> SEQUENCE: 199

Gln Leu Pro Glu Leu Lys Gln Lys Ser Ser Asn Ser Arg Lys Lys Arg
1               5                   10                  15
```

Ser Thr Ser Ala
            20

<210> SEQ ID NO 200
<211> LENGTH: 14
<212> TYPE: PRT
<213> ORGANISM: Bacillus anthracis

<400> SEQUENCE: 200

Tyr Thr Val Asp Val Lys Asn Lys Arg Thr Phe Leu Ser Pro
1               5                   10

<210> SEQ ID NO 201
<211> LENGTH: 16
<212> TYPE: PRT
<213> ORGANISM: Bacillus anthracis

<400> SEQUENCE: 201

Pro Tyr Ser Asp Phe Glu Lys Val Thr Gly Arg Ile Asp Lys Asn Val
1               5                   10                  15

<210> SEQ ID NO 202
<211> LENGTH: 14
<212> TYPE: PRT
<213> ORGANISM: Bacillus anthracis

<400> SEQUENCE: 202

Ser Glu Thr Arg Thr Ile Ser Lys Asn Thr Ser Thr Ser Arg
1               5                   10

<210> SEQ ID NO 203
<211> LENGTH: 18
<212> TYPE: PRT
<213> ORGANISM: Bacillus anthracis

<400> SEQUENCE: 203

Ile Gly Gly Ser Val Ser Ala Gly Phe Ser Asn Ser Asn Ser Ser Thr
1               5                   10                  15

Val Ala

<210> SEQ ID NO 204
<211> LENGTH: 10
<212> TYPE: PRT
<213> ORGANISM: Bacillus anthracis

<400> SEQUENCE: 204

Leu Asn Ala Asn Ile Arg Tyr Val Asn Thr
1               5                   10

<210> SEQ ID NO 205
<211> LENGTH: 14
<212> TYPE: PRT
<213> ORGANISM: Bacillus anthracis

<400> SEQUENCE: 205

Ala Pro Asn Asn Tyr Tyr Pro Ser Lys Asn Leu Ala Pro Ile
1               5                   10

<210> SEQ ID NO 206
<211> LENGTH: 12
<212> TYPE: PRT
<213> ORGANISM: Bacillus anthracis

<400> SEQUENCE: 206

```
Gln Gln Thr Ser Gln Asn Ile Lys Asn Gln Leu Ala
1               5                   10
```

<210> SEQ ID NO 207
<211> LENGTH: 10
<212> TYPE: PRT
<213> ORGANISM: Bacillus anthracis

<400> SEQUENCE: 207

```
Leu Leu Asn Ile Asp Lys Asp Ile Arg Lys
1               5                   10
```

<210> SEQ ID NO 208
<211> LENGTH: 10
<212> TYPE: PRT
<213> ORGANISM: Bacillus anthracis

<400> SEQUENCE: 208

```
Ile Leu Ile Phe Ser Lys Lys Gly Tyr Glu
1               5                   10
```

<210> SEQ ID NO 209
<211> LENGTH: 12
<212> TYPE: PRT
<213> ORGANISM: Bacillus anthracis

<400> SEQUENCE: 209

```
Lys Phe Ile Pro Asn Lys Phe Ser Ile Ile Ser Phe
1               5                   10
```

<210> SEQ ID NO 210
<211> LENGTH: 12
<212> TYPE: PRT
<213> ORGANISM: Bacillus anthracis

<400> SEQUENCE: 210

```
Ser Arg Phe Val Phe Glu Lys Lys Arg Glu Thr Pro
1               5                   10
```

<210> SEQ ID NO 211
<211> LENGTH: 12
<212> TYPE: PRT
<213> ORGANISM: Bacillus anthracis

<400> SEQUENCE: 211

```
Gly Asn Leu Glu Asn Lys Lys Ser Ile Thr Glu His
1               5                   10
```

<210> SEQ ID NO 212
<211> LENGTH: 12
<212> TYPE: PRT
<213> ORGANISM: Bacillus anthracis

<400> SEQUENCE: 212

```
Gly Lys Ile Pro Leu Lys Leu Asp His Leu Arg Ile
1               5                   10
```

<210> SEQ ID NO 213
<211> LENGTH: 11
<212> TYPE: PRT
<213> ORGANISM: Bacillus anthracis

<400> SEQUENCE: 213

```
Glu Asn Gly Ile Ile Lys Gly Lys Lys Glu Ile
```

-continued

```
<210> SEQ ID NO 214
<211> LENGTH: 18
<212> TYPE: PRT
<213> ORGANISM: Bacillus anthracis

<400> SEQUENCE: 214

Val Leu Gly Glu Lys Phe Asn Trp Arg Asn Ile Glu Val Met Ala Lys
1               5                   10                  15

Asn Val

<210> SEQ ID NO 215
<211> LENGTH: 18
<212> TYPE: PRT
<213> ORGANISM: Bacillus anthracis

<400> SEQUENCE: 215

Val Met Ala Lys Asn Val Glu Gly Val Leu Lys Pro Leu Thr Ala Asp
1               5                   10                  15

Tyr Asp

<210> SEQ ID NO 216
<211> LENGTH: 16
<212> TYPE: PRT
<213> ORGANISM: Bacillus anthracis

<400> SEQUENCE: 216

Thr Glu Ile Lys Lys Gln Ile Pro Thr Lys Arg Met Asp Lys Val Val
1               5                   10                  15

<210> SEQ ID NO 217
<211> LENGTH: 16
<212> TYPE: PRT
<213> ORGANISM: Bacillus anthracis

<400> SEQUENCE: 217

Pro Asn Ser Leu Glu Lys Gln Lys Gly Val Thr Asn Leu Leu Ile Lys
1               5                   10                  15

<210> SEQ ID NO 218
<211> LENGTH: 12
<212> TYPE: PRT
<213> ORGANISM: Bacillus anthracis

<400> SEQUENCE: 218

Thr Asn Leu Leu Ile Lys Tyr Gly Ile Glu Arg Lys
1               5                   10

<210> SEQ ID NO 219
<211> LENGTH: 21
<212> TYPE: PRT
<213> ORGANISM: Bacillus anthracis

<400> SEQUENCE: 219

Lys Thr Leu Ser Asn Trp Gln Lys Gln Met Leu Asp Arg Leu Asn Glu
1               5                   10                  15

Ala Val Lys Tyr Thr
                20

<210> SEQ ID NO 220
<211> LENGTH: 14
<212> TYPE: PRT
```

<213> ORGANISM: Bacillus anthracis

<400> SEQUENCE: 220

Phe Ile Lys Asn Leu Ser Ser Ile Arg Arg Ser Ser Asn Val
1               5                   10

<210> SEQ ID NO 221
<211> LENGTH: 10
<212> TYPE: PRT
<213> ORGANISM: Bacillus anthracis

<400> SEQUENCE: 221

Phe Ser Gln Glu Lys Lys Arg Lys Ile Ser
1               5                   10

<210> SEQ ID NO 222
<211> LENGTH: 16
<212> TYPE: PRT
<213> ORGANISM: Bacillus anthracis

<400> SEQUENCE: 222

Ala Pro Glu Tyr Lys Asn Tyr Phe Gln Tyr Leu Lys Glu Arg Ile Thr
1               5                   10                  15

<210> SEQ ID NO 223
<211> LENGTH: 13
<212> TYPE: PRT
<213> ORGANISM: Bacillus anthracis

<400> SEQUENCE: 223

Asn Gln Val Gln Leu Leu Thr His Gln Lys Ser Asn Ile
1               5                   10

<210> SEQ ID NO 224
<211> LENGTH: 12
<212> TYPE: PRT
<213> ORGANISM: Bacillus anthracis

<400> SEQUENCE: 224

His Gln Lys Ser Asn Ile Glu Phe Lys Leu Leu Tyr
1               5                   10

<210> SEQ ID NO 225
<211> LENGTH: 12
<212> TYPE: PRT
<213> ORGANISM: Bacillus anthracis

<400> SEQUENCE: 225

Glu Asn Glu Thr Asp Asn Phe Glu Val Phe Gln Lys
1               5                   10

<210> SEQ ID NO 226
<211> LENGTH: 10
<212> TYPE: PRT
<213> ORGANISM: Bacillus anthracis

<400> SEQUENCE: 226

Lys Asn Ser Met Asn Ser Arg Gly Glu Lys
1               5                   10

<210> SEQ ID NO 227
<211> LENGTH: 10
<212> TYPE: PRT
<213> ORGANISM: Bacillus anthracis

```
<400> SEQUENCE: 227

Ser Met Asn Ser Arg Gly Glu Lys Val Pro
1               5                   10

<210> SEQ ID NO 228
<211> LENGTH: 10
<212> TYPE: PRT
<213> ORGANISM: Bacillus anthracis

<400> SEQUENCE: 228

Asn Ser Arg Gly Glu Lys Val Pro Phe Ala
1               5                   10

<210> SEQ ID NO 229
<211> LENGTH: 10
<212> TYPE: PRT
<213> ORGANISM: Bacillus anthracis

<400> SEQUENCE: 229

Arg Gly Glu Lys Val Pro Phe Ala Ser Arg
1               5                   10

<210> SEQ ID NO 230
<211> LENGTH: 10
<212> TYPE: PRT
<213> ORGANISM: Bacillus anthracis

<400> SEQUENCE: 230

Glu Lys Val Pro Phe Ala Ser Arg Phe Val
1               5                   10

<210> SEQ ID NO 231
<211> LENGTH: 10
<212> TYPE: PRT
<213> ORGANISM: Bacillus anthracis

<400> SEQUENCE: 231

Tyr Ala Ile Asn Ser Glu Gln Ser Lys Glu
1               5                   10

<210> SEQ ID NO 232
<211> LENGTH: 10
<212> TYPE: PRT
<213> ORGANISM: Bacillus anthracis

<400> SEQUENCE: 232

Ile Asn Ser Glu Gln Ser Lys Glu Val Tyr
1               5                   10

<210> SEQ ID NO 233
<211> LENGTH: 10
<212> TYPE: PRT
<213> ORGANISM: Bacillus anthracis

<400> SEQUENCE: 233

Ser Ser Asp Leu Leu Phe Ser Gln Lys Phe
1               5                   10

<210> SEQ ID NO 234
<211> LENGTH: 10
<212> TYPE: PRT
<213> ORGANISM: Bacillus anthracis

<400> SEQUENCE: 234
```

```
Asp Leu Leu Phe Ser Gln Lys Phe Lys Glu
1               5                   10

<210> SEQ ID NO 235
<211> LENGTH: 10
<212> TYPE: PRT
<213> ORGANISM: Bacillus anthracis

<400> SEQUENCE: 235

Leu Glu Leu Tyr Ala Pro Asp Met Phe Glu
1               5                   10

<210> SEQ ID NO 236
<211> LENGTH: 10
<212> TYPE: PRT
<213> ORGANISM: Bacillus anthracis

<400> SEQUENCE: 236

Leu Tyr Ala Pro Asp Met Phe Glu Tyr Met
1               5                   10

<210> SEQ ID NO 237
<211> LENGTH: 10
<212> TYPE: PRT
<213> ORGANISM: Bacillus anthracis

<400> SEQUENCE: 237

Glu Gly Glu Ile Gly Lys Ile Pro Leu Lys
1               5                   10

<210> SEQ ID NO 238
<211> LENGTH: 10
<212> TYPE: PRT
<213> ORGANISM: Bacillus anthracis

<400> SEQUENCE: 238

Glu Ile Gly Lys Ile Pro Leu Lys Leu Asp
1               5                   10

<210> SEQ ID NO 239
<211> LENGTH: 10
<212> TYPE: PRT
<213> ORGANISM: Bacillus anthracis

<400> SEQUENCE: 239

Asp Tyr Asp Leu Phe Ala Leu Ala Pro Ser
1               5                   10

<210> SEQ ID NO 240
<211> LENGTH: 10
<212> TYPE: PRT
<213> ORGANISM: Bacillus anthracis

<400> SEQUENCE: 240

Asp Leu Phe Ala Leu Ala Pro Ser Leu Thr
1               5                   10

<210> SEQ ID NO 241
<211> LENGTH: 10
<212> TYPE: PRT
<213> ORGANISM: Bacillus anthracis

<400> SEQUENCE: 241

Asn Trp Gln Lys Gln Met Leu Asp Arg Leu
1               5                   10
```

-continued

<210> SEQ ID NO 242
<211> LENGTH: 10
<212> TYPE: PRT
<213> ORGANISM: Bacillus anthracis

<400> SEQUENCE: 242

Gln Lys Gln Met Leu Asp Arg Leu Asn Glu
1               5                   10

<210> SEQ ID NO 243
<211> LENGTH: 10
<212> TYPE: PRT
<213> ORGANISM: Bacillus anthracis

<400> SEQUENCE: 243

Gln Met Leu Asp Arg Leu Asn Glu Ala Val
1               5                   10

<210> SEQ ID NO 244
<211> LENGTH: 10
<212> TYPE: PRT
<213> ORGANISM: Bacillus anthracis

<400> SEQUENCE: 244

Asn Glu Ala Val Lys Tyr Thr Gly Tyr Thr
1               5                   10

<210> SEQ ID NO 245
<211> LENGTH: 10
<212> TYPE: PRT
<213> ORGANISM: Bacillus anthracis

<400> SEQUENCE: 245

Ala Val Lys Tyr Thr Gly Tyr Thr Gly Gly
1               5                   10

<210> SEQ ID NO 246
<211> LENGTH: 10
<212> TYPE: PRT
<213> ORGANISM: Bacillus anthracis

<400> SEQUENCE: 246

Gln Asp Asn Glu Glu Phe Pro Glu Lys Asp
1               5                   10

<210> SEQ ID NO 247
<211> LENGTH: 10
<212> TYPE: PRT
<213> ORGANISM: Bacillus anthracis

<400> SEQUENCE: 247

Asn Glu Glu Phe Pro Glu Lys Asp Asn Glu
1               5                   10

<210> SEQ ID NO 248
<211> LENGTH: 10
<212> TYPE: PRT
<213> ORGANISM: Bacillus anthracis

<400> SEQUENCE: 248

Glu Phe Pro Glu Lys Asp Asn Glu Ile Phe
1               5                   10

<210> SEQ ID NO 249
<211> LENGTH: 18
<212> TYPE: PRT
<213> ORGANISM: Bacillus anthracis

<400> SEQUENCE: 249

Lys Asn Ser Met Asn Ser Arg Gly Glu Lys Val Pro Phe Ala Ser Arg
1               5                   10                  15

Phe Val

<210> SEQ ID NO 250
<211> LENGTH: 12
<212> TYPE: PRT
<213> ORGANISM: Bacillus anthracis

<400> SEQUENCE: 250

Tyr Ala Ile Asn Ser Glu Gln Ser Lys Glu Val Tyr
1               5                   10

<210> SEQ ID NO 251
<211> LENGTH: 12
<212> TYPE: PRT
<213> ORGANISM: Bacillus anthracis

<400> SEQUENCE: 251

Ser Ser Asp Leu Leu Phe Ser Gln Lys Phe Lys Glu
1               5                   10

<210> SEQ ID NO 252
<211> LENGTH: 12
<212> TYPE: PRT
<213> ORGANISM: Bacillus anthracis

<400> SEQUENCE: 252

Leu Glu Leu Tyr Ala Pro Asp Met Phe Glu Tyr Met
1               5                   10

<210> SEQ ID NO 253
<211> LENGTH: 12
<212> TYPE: PRT
<213> ORGANISM: Bacillus anthracis

<400> SEQUENCE: 253

Glu Gly Glu Ile Gly Lys Ile Pro Leu Lys Leu Asp
1               5                   10

<210> SEQ ID NO 254
<211> LENGTH: 12
<212> TYPE: PRT
<213> ORGANISM: Bacillus anthracis

<400> SEQUENCE: 254

Asp Tyr Asp Leu Phe Ala Leu Ala Pro Ser Leu Thr
1               5                   10

<210> SEQ ID NO 255
<211> LENGTH: 14
<212> TYPE: PRT
<213> ORGANISM: Bacillus anthracis

<400> SEQUENCE: 255

Asn Trp Gln Lys Gln Met Leu Asp Arg Leu Asn Glu Ala Val
1               5                   10

```
<210> SEQ ID NO 256
<211> LENGTH: 12
<212> TYPE: PRT
<213> ORGANISM: Bacillus anthracis

<400> SEQUENCE: 256

Asn Glu Ala Val Lys Tyr Thr Gly Tyr Thr Gly Gly
1               5                   10

<210> SEQ ID NO 257
<211> LENGTH: 14
<212> TYPE: PRT
<213> ORGANISM: Bacillus anthracis

<400> SEQUENCE: 257

Gln Asp Asn Glu Glu Phe Pro Glu Lys Asp Asn Glu Ile Phe
1               5                   10

<210> SEQ ID NO 258
<211> LENGTH: 34
<212> TYPE: PRT
<213> ORGANISM: Bacillus anthracis

<400> SEQUENCE: 258

Gln His Arg Asp Val Leu Gln Leu Tyr Ala Pro Glu Ala Phe Asn Tyr
1               5                   10                  15

Met Asp Lys Phe Asn Glu Gly Glu Ile Asn Leu Ser Leu Glu Leu
            20                  25                  30

Lys Asp

<210> SEQ ID NO 259
<211> LENGTH: 20
<212> TYPE: PRT
<213> ORGANISM: Bacillus anthracis

<400> SEQUENCE: 259

Asp Phe Leu Ser Thr Glu Glu Lys Glu Phe Leu Lys Lys Leu Gln Ile
1               5                   10                  15

Asp Ile Arg Asp
            20

<210> SEQ ID NO 260
<211> LENGTH: 12
<212> TYPE: PRT
<213> ORGANISM: Bacillus anthracis

<400> SEQUENCE: 260

Gly Pro Tyr Asp Ile Asn Gly Arg Leu Gln Asp Thr
1               5                   10

<210> SEQ ID NO 261
<211> LENGTH: 12
<212> TYPE: PRT
<213> ORGANISM: Bacillus anthracis

<400> SEQUENCE: 261

Gly Tyr Thr His Gln Asp Glu Ile Tyr Glu Gly Val
1               5                   10

<210> SEQ ID NO 262
<211> LENGTH: 20
<212> TYPE: PRT
<213> ORGANISM: Bacillus anthracis
```

-continued

```
<400> SEQUENCE: 262

Ser Thr Thr Gly Asp Leu Ser Ile Pro Ser Ser Glu Leu Glu Asn Ile
1               5                   10                  15

Asp Ser Glu Asn
            20

<210> SEQ ID NO 263
<211> LENGTH: 18
<212> TYPE: PRT
<213> ORGANISM: Bacillus anthracis

<400> SEQUENCE: 263

Asn Ala Glu Val His Ala Ser Phe Glu Asp Ile Gly Gly Ser Val Ser
1               5                   10                  15

Ala Gly

<210> SEQ ID NO 264
<211> LENGTH: 14
<212> TYPE: PRT
<213> ORGANISM: Bacillus anthracis

<400> SEQUENCE: 264

Arg Lys Lys Arg Ser Thr Ser Ala Gly Pro Thr Val Pro Asp
1               5                   10

<210> SEQ ID NO 265
<211> LENGTH: 16
<212> TYPE: PRT
<213> ORGANISM: Bacillus anthracis

<400> SEQUENCE: 265

Ser Asp Pro Tyr Ser Asp Phe Glu Lys Val Thr Gly Arg Ile Asp Lys
1               5                   10                  15

<210> SEQ ID NO 266
<211> LENGTH: 16
<212> TYPE: PRT
<213> ORGANISM: Bacillus anthracis

<400> SEQUENCE: 266

Val Leu Gln Leu Tyr Ala Pro Glu Ala Phe Asn Tyr Met Asp Lys Phe
1               5                   10                  15

<210> SEQ ID NO 267
<211> LENGTH: 10
<212> TYPE: PRT
<213> ORGANISM: Bacillus anthracis

<400> SEQUENCE: 267

Ser Glu Glu Gly Arg Gly Leu Leu Lys Lys
1               5                   10
```